US011199976B2

(12) United States Patent
O'Hare et al.

(10) Patent No.: US 11,199,976 B2
(45) Date of Patent: *Dec. 14, 2021

(54) GATEWAY FOR CLOUD-BASED SECURE STORAGE

(71) Applicant: Security First Corp., Rancho Santa Margarita, CA (US)

(72) Inventors: Mark S. O'Hare, Coto De Caza, CA (US); Rick L. Orsini, Flower Mound, TX (US)

(73) Assignee: SECURITY FIRST CORP., Rancho Santa Margarita, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/042,643

(22) Filed: Jul. 23, 2018

(65) Prior Publication Data

US 2018/0349047 A1 Dec. 6, 2018

Related U.S. Application Data

(63) Continuation of application No. 14/949,370, filed on Nov. 23, 2015, now Pat. No. 10,031,679.

(Continued)

(51) Int. Cl.
*H04L 9/32* (2006.01)
*G06F 3/06* (2006.01)
(Continued)

(52) U.S. Cl.
CPC ............ *G06F 3/0619* (2013.01); *G06F 3/067* (2013.01); *G06F 3/0665* (2013.01);
(Continued)

(58) Field of Classification Search
CPC ...... G06F 3/0665; G06F 3/062; G06F 3/0622; G06F 3/0623; G06F 17/30091; G06F 17/30312; G06F 3/067; G06F 3/0683; G06F 17/30194; G06F 21/6218; G06F 12/1408; G06F 3/064; G06F 3/0619; G06F 16/128; G06F 16/182; G06F 3/0689; G06F 12/0868; G06F 2201/835; G06F 2201/815; G06F 11/1446; G06F 11/2005; G06F 2201/84; G06F 2212/1052; G06F 2212/224; H04L 67/1097; H04L 63/0428; H04L 67/2842; H04L 9/3297; H04L 63/061
See application file for complete search history.

(56) References Cited

U.S. PATENT DOCUMENTS 6,745,311 B2 * 6/2004 Fabrizio .................. G01K 7/01
374/E7.035
8,601,134 B1 * 12/2013 Sorenson, III ...... H04L 67/1097
709/227

(Continued)

*Primary Examiner* — Trong H Nguyen

(57) ABSTRACT

The systems and methods disclosed herein transparently provide an improved scalable cloud-based dynamically adjustable or configurable storage volume. In one aspect, a gateway provides a dynamically or configurably adjustable storage volume, including a local cache. The storage volume may be transparently adjusted for the amount of data that needs to be stored using available local or cloud-based storage. The gateway may use caching techniques and block clustering to provide gains in access latency compared to existing gateway systems, while providing scalable off-premises storage.

20 Claims, 30 Drawing Sheets

Related U.S. Application Data

(60) Provisional application No. 62/083,116, filed on Nov. 21, 2014.

(51) Int. Cl.

| | | |
|---|---|---|
| *G06F 16/11* | (2019.01) | |
| *G06F 16/182* | (2019.01) | |
| *G06F 21/62* | (2013.01) | |
| *G16H 10/60* | (2018.01) | |
| *G06F 12/0868* | (2016.01) | |
| *G06F 12/14* | (2006.01) | |
| *H04L 29/06* | (2006.01) | |
| *H04L 29/08* | (2006.01) | |
| *G06F 11/14* | (2006.01) | |
| *G06F 11/20* | (2006.01) | |

(52) U.S. Cl.
CPC ........ *G06F 3/0689* (2013.01); *G06F 11/1469* (2013.01); *G06F 12/0868* (2013.01); *G06F 12/1408* (2013.01); *G06F 16/128* (2019.01); *G06F 16/182* (2019.01); *G06F 21/6218* (2013.01); *G16H 10/60* (2018.01); *H04L 9/3297* (2013.01); *H04L 63/0428* (2013.01); *H04L 63/061* (2013.01); *H04L 67/1097* (2013.01); *H04L 67/2842* (2013.01); *G06F 3/064* (2013.01); *G06F 11/1446* (2013.01); *G06F 11/2005* (2013.01); *G06F 2201/815* (2013.01); *G06F 2201/835* (2013.01); *G06F 2201/84* (2013.01); *G06F 2212/1052* (2013.01); *G06F 2212/224* (2013.01)

(56) References Cited

U.S. PATENT DOCUMENTS

| | | | |
|---|---|---|---|
| 8,788,803 | B2 | 7/2014 | Irvine |
| 8,874,680 | B1* | 10/2014 | Das .................... G06F 12/0833 709/212 |
| 9,268,651 | B1* | 2/2016 | Salyers ............... G06F 11/1464 |
| 2005/0111657 | A1 | 5/2005 | Lee |
| 2007/0160198 | A1* | 7/2007 | Orsini .................... H04L 9/085 380/28 |
| 2012/0042162 | A1* | 2/2012 | Anglin ................ G06F 21/6218 713/165 |
| 2012/0047339 | A1* | 2/2012 | Decasper ............ G06F 11/1076 711/162 |
| 2012/0191912 | A1* | 7/2012 | Kadatch ............. G06F 11/1044 711/119 |
| 2012/0233293 | A1* | 9/2012 | Barton ................ G06F 11/1004 709/219 |

* cited by examiner

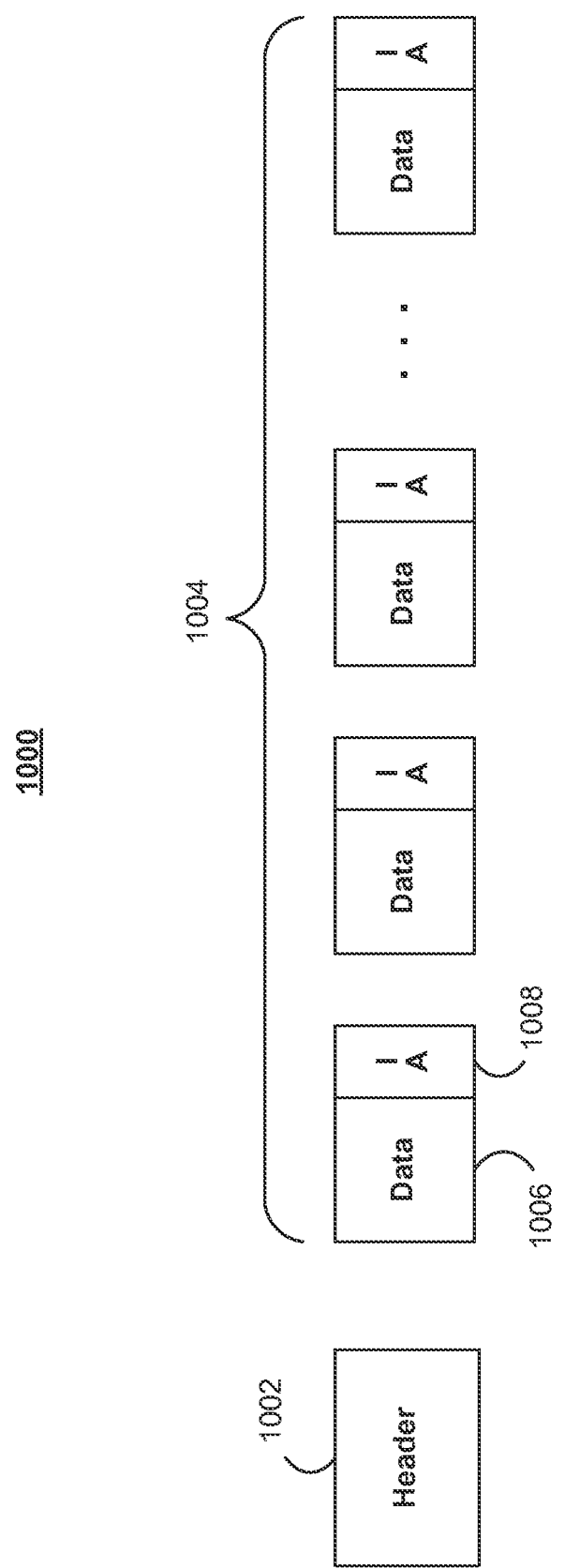

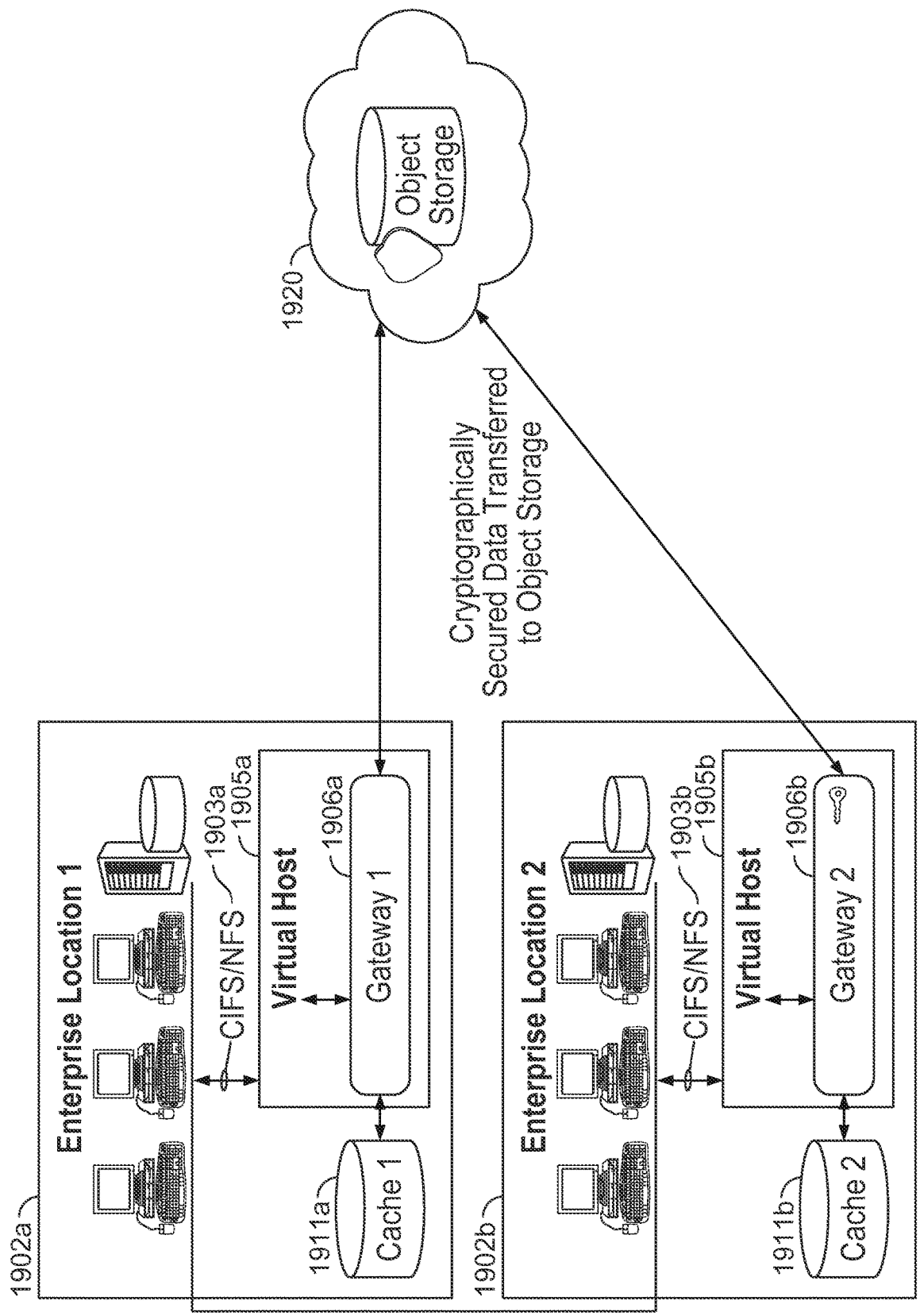

GATEWAY FOR CLOUD-BASED SECURE STORAGE

CROSS-REFERENCE TO RELATED APPLICATIONS

This application is a continuation application of U.S. patent application Ser. No. 14/949,370, filed Nov. 23, 2015, which claims priority to U.S. Provisional Application No. 62/083,116, filed Nov. 21, 2014, the content of which is hereby incorporated by reference herein in its entirety. This is related to International Patent Application No. PCT/US15/62188 and U.S. patent application Ser. No. 14/949,519, both filed Nov. 23, 2015, each of which is hereby incorporated by reference herein in its entirety.

BACKGROUND

Data storage on a computer system includes hardware such as memory, components, devices and/or other storage media that may retain digital computer data. Typical data storage space provided by a computing device ranges from a few gigabytes (GBs) to several terabytes (TBs). Today's computer systems and networks, for example, for an enterprise network, may need to store large numbers of data files in the billions, and thus demand a high data storage capacity. With an ever-increasing need to expand storage capacity, local hardware storage needs to be scaled to meet the data storage demand. However, large-scale hardware storage facilities usually take up significant physical space, which may be impractical within an enterprise infrastructure.

One approach to expand the storage capacity is to provide remote storage at a remote server such as a file transfer protocol (FTP) site. A local computer system may send data files to the remote server for storage. When a user needs to retrieve a data file, the user usually needs to determine a remote location where the data file is located, and sends a request to the respective remote server, which may in turn return the requested file to a local device for the user to retrieve. This remote storage solution may help to alleviate the burden to expand local hardware storage. However, additional operation overhead on the user side may be incurred as the user may often need to send file retrieval requests and download files from a remote location. In addition, data security and latency for sending or downloading data files from a remote location may impair the performance of the remote data storage system.

SUMMARY

Systems and methods described herein provide a gateway for managing cloud-based secure storage (e.g., by incorporating a local cache memory and/or one or more cloud-based storage servers into a virtual disk for presentation to a client device). In this way, an improved scalable virtual storage system that has a dynamically adjustable or configurable storage volume may be created for a client computer system.

According to one aspect, a method for providing improved scalable cloud-based storage to a client computer system is provided. The method includes receiving, using a programmed hardware processor, a data storage request associated with a data file, wherein the data storage request is generated by an application running on the client computer system. A storage volume is provisioned for the client computer system. The provisioned storage volume includes a local cache memory communicatively coupled to the client computer system and a cloud library comprising one or more remote storage devices in one or more clouds. In some implementations, the local cache memory comprises non-volatile memory located within the client computer system or in a gateway server within a local network of the client computer system. The provisioned storage volume may be dynamically or configurably adjustable (e.g., by transparently including or excluding a subset of the one or more remote storage devices and one or more local storage devices). As used herein, "dynamically adjusting", "dynamically adjustable," and similar terms when applied to the local cache memory or the storage volume refer to setting or changing the total size of a local cache memory or remote (cloud-based) storage (as may be applicable) allocated to one or more enterprise user devices in response to detecting that additional storage space may be needed or may be desirable in the storage volume. Detecting that additional storage space may be needed or may be desirable in the storage volume or the local cache memory may include, for example, detecting that available storage in the allocated local cache memory and/or the allocated remote (cloud-based) storage is less than or equal to an applicable threshold value. Alternatively or additionally, detecting that additional storage space may be needed or may be desirable in the storage volume may include, for example, detecting that a data size associated with a data storage request or a data access request exceeds available storage in the allocated local cache memory and/or the allocated remote (cloud-based) storage. As used herein, "configurably adjusting", "configurably adjustable," and similar terms when applied to the local cache memory or the storage volume refer to setting or changing the total size of a local cache memory or remote (cloud-based) storage (as may be applicable) allocated to one or more enterprise user devices based on an applicable user- or system-specified parameter. The parameter may specify a maximum limit, a minimum limit, or both for the allocated storage space, and a gateway associated with the virtual storage system may manage the allocated storage space subject to such maximum and/or minimum limit. It is understood that the storage system described herein may be both dynamically and configurably adjustable. For example, the gateway may increase or decrease allocated storage space in response to detecting that additional storage space may be needed or may be desirable in the storage volume or the local cache memory, and such decreases or increases may be subject to an upper or lower limit on total cache size determined by a configuration parameter.

The data file associated with the storage request is included in one or more "cluster blocks." A cluster block includes a group of data blocks that are written or transmitted together to (or retrieved or received together from) the cloud storage simultaneously. The larger unit size resulting from the use of cluster blocks may be desirable in the context of reading or writing operations for remote storage devices because it reduces the burden of frequent remote data operation to or from the cloud. Several data blocks, each of which may be associated with a sequential identifier, may thus be combined to form a cluster block. For example, data blocks may be sequentially (or otherwise deterministically) grouped based on the respective sequential identifiers. Alternatively, data blocks may be randomly grouped based on, for example, relevance, correlation between data blocks, type of the data, a date when the data was created, etc. A cluster block may include data blocks belonging to a single data file (in whole or in part), data blocks from more than one data file, or any combination thereof. It will be understood that while a cluster block may be transmitted to or received from the cloud as part of the same transaction, the cluster block need not be stored as a unit within the cloud storage. For example, for security reasons, a single cluster block may be broken up and the portions may be stored in separate data shares at the same or different locations within the cloud. The ability to flexibly select or modify the cluster block size provides several advantages, including ensuring an efficient use of network resources while reducing access latency. Conventional cloud-based gateways treat the data file as a unit when reading or writing to the cloud. Because writing/reading to the cloud may be expensive (due to the access latency as well as access fees charged per access), small files may result in high overhead costs since each trip to the cloud fetches too little data. However, if the cluster block is too big, the gateway might tie up memory and network resources fetching excess data that is unlikely to be needed.

In some implementations, including the data file in one or more cluster blocks comprises generating, using a device mapper module, one or more sequential identifiers for a subset of data blocks generated from the data file, and updating a block map for the one or more cluster blocks to associate the sequential identifiers with the data file. Each cluster block may have a predetermined size determined based on one or more criteria including cloud-access latency, a total size of the data file, a file type of the data file, and a total capacity of the local cache memory. Moreover, each cluster block may include data blocks obtained from multiple separate data files or from a single data file. The method further includes causing the one or more cluster blocks to be stored in the local cache memory, and causing the one or more cluster blocks to be transparently stored to the one or more remote storage devices.

In some implementations, in response to detecting a change in a respective one of the one or more cluster blocks, an upload status indicator associated with the respective cluster block is updated (e.g., to set the upload status flag, and thereby mark the cluster block as having been changed and added to a set of cluster blocks to be uploaded to the cloud library). Similarly, the upload status indicator may be updated (e.g., by clearing the upload status flag) associated with the respective one of the one or more cluster blocks in response to detecting that the respective cluster block is stored to the cloud library. The one or more remote storage devices may be geographically separated, or in some cases, they may be in the same location. In some implementations, the method further includes removing the respective cluster block from the local cache memory in response to detecting that the respective cluster block is stored to the cloud library. In some implementations, in order to maintain the available space in the local cache at or above a threshold, one or more selected (e.g., previously uploaded) cluster blocks may be removed from the local cache memory in response to detecting that an available storage space of the local cache memory is less than or equal to a predetermined threshold. The selected cluster block(s) for removal may correspond to the least recently used cluster block in the local cache memory or the least frequently used cluster block in the local cache memory. The method may also include transparently increasing a total capacity of the local cache memory in response to detecting that a file size of the data file exceeds an available storage capacity of the local cache. Alternatively or additionally, the method may include controlling a data transfer rate to the local cache memory in response to detecting that a file size of the data file exceeds an available storage capacity of the local cache, thereby avoiding storage overflow of the local cache memory.

The gateway may include cryptographic operations for securing the data. For example, causing the one or more cluster blocks to be stored in the local cache memory may include applying a first cryptographic operation to the one or more cluster blocks. The first cryptographic operation may include encrypting the one or more cluster blocks using a first encryption key. Furthermore, causing the one or more cluster blocks to be transparently stored to the one or more remote storage devices may include applying a second cryptographic operation to the one or more cluster blocks. The second cryptographic operation may include encrypting the one or more cluster blocks using a second encryption key different from the first encryption key. The first encryption key, the second encryption key, or both may be stored in a separate storage location from the respective cluster blocks that they secure. In some implementations, causing the one or more cluster blocks to be transparently stored to the one or more remote storage devices includes causing the one or more cluster blocks to be distributed in data shares located in the one or more remote storage devices, each share including a portion of each cluster block in a subset of the cluster blocks. For example, each cluster block may be shuffled into a single data share (e.g., by interleaving the cluster block into the data share, or by reordering an original order of data units in the cluster block). In some implementations, causing each share to be distributed in data shares includes splitting each cluster block into secondary data units and causing each secondary data unit to be placed into one of the data shares, so that each cluster block is restorable by recombining a subset less than all of the secondary data units from the data shares. For example, the secondary data units may be placed into the data shares using on a key generated based on a random or pseudo-random number.

According to one aspect, a method for providing improved scalable cloud-based storage to a client computer system including providing access to data files transparently stored by a cloud-based storage system. The method includes presenting to the client computer system a virtual disk associated with a provisioned storage volume that stores one or more data files of the client computer system. The provisioned storage volume includes a local cache memory communicatively coupled to the client computer system and a cloud library comprising one or more remote storage devices in one or more clouds. In some implementations, the local cache memory comprises non-volatile memory located within the client computer system or in a gateway server within a local network of the client computer system. The provisioned storage volume may be dynamically or configurably adjustable by transparently including or excluding a subset of the one or more remote storage devices and one or more local storage devices. The method includes receiving, from the client computer system, a request to access a selected data file from the one or more data files stored by the volume. One or more cluster blocks associated with the selected data file are identified (e.g., using the device mapper) based at least in part on a cluster block map that relates information associated with the selected data file to information maintained by the cluster block map for the cluster blocks. The method includes transparently retrieving the selected data file from the one or more cluster blocks in response to determining that the one or more cluster blocks are stored in the local cache memory. If any of the cluster blocks is missing from the local cache memory, the missing cluster block(s) may be transparently retrieved from a storage location in the cloud library, the storage location being hidden from the client computer system. The selected data file is then retrieved or re-composed from data blocks in the cluster block(s) and provided to the client computer system. The retrieved cluster blocks may also be stored in the local cache memory for future requests.

The method may further include updating a usage counter associated with the one or more cluster blocks. In some implementations, retrieving the at least one cluster block from the cloud library includes recombining a threshold number of secondary data units of the at least cluster block, the threshold number being less than all of the secondary data units of the cluster block. The secondary data units of the at least one cluster block may be stored ion data shares located at geographically separated locations. In some implementations, the at least one cluster block comprises encrypted data and the recombining is performed without decrypting the encrypted data.

According to another aspect (which may be combined with any of the methods and processes described herein), a method for transparently providing data recovery to a client computer system using cloud-based storage is provided. The method includes detecting a request to capture a snapshot of a local file system of the client computer system at a first timestamp, where one or more data files associated with the client computer system are transparently stored to a provisioned storage volume. The provisioned volume may be similar to any of the volumes described herein, and may include, for example, a local cache memory communicatively coupled to the client computer system and a cloud library comprising one or more remote storage devices. In response to detecting the request, a snapshot capture indicator including the first timestamp is sent to a gateway manager associated with the storage volume. Using the gateway manager, a first capture of a state of the local cache memory at the first timestamp is generated, and a second capture of a state of one or more cluster blocks (that include the one or more data files) stored by the one or more remote storage devices at the first timestamp is requested or generated by the gateway. The method further includes generating a capture version number for the first and second capture based on the snapshot capture indicator, and causing the storage volume to store the first capture, the second capture and the capture version number. The method may include causing the storage volume to store the second capture associated with the first timestamp without overwriting a prior capture associated with an earlier timestamp. The method may also include presenting, to the client computer system, the second capture in synchronization with the first capture in response to a second request from the client computer system to restore the state of the file system associated with the first timestamp. For example, the method may include receiving a data access request to recover a version of the one or more data files associated with the first timestamp, transparently accessing the second capture of the storage volume based on the first timestamp, and transparently retrieving the version of the one or more data files from the second capture.

In some implementations, causing the storage volume to store the first and/or second capture includes cryptographically securing the first and/or the second capture. For example, by applying, at the local cache memory, a first cryptographic operation to the first or the second capture based on a first encryption key, and applying, at a cloud interface, a second cryptographic operation based on a second encryption key to the first or the second capture that is already encrypted with the first encryption key. The method may also include storing the first encryption key, the second encryption key, or both in a separate storage location from the first or the second capture. In some implementations, causing the storage volume to store the first or the second capture includes causing the first or the second capture to be distributed in data shares located in the one or more remote storage devices. For example, one or more cluster blocks may be generated from the first and/or the second capture. The cluster blocks may be split into secondary data units, and each secondary data unit may be placed into one of the data shares. The cluster blocks may be split and distributed such that ach cluster block is restorable by recombining a subset less than all of the secondary data units from the data shares, as discussed herein. In some implementations, causing the storage volume to store the first or the second capture includes causing the first capture and/or the second capture associated with the first timestamp and the version number to be stored in a data recovery folder.

Systems, computer-readable media, and other apparatuses may also be provided in accordance with one or more of the methods described above.

BRIEF DESCRIPTION OF THE DRAWINGS

The present disclosure is described in more detail below in connection with the attached drawings, which are meant to illustrate and not to limit the disclosure, and in which:

FIG. 10 is a simplified block diagram of an illustrative share format, that may be used in any suitable combination, with any suitable additions, deletions, or modifications in accordance with one implementation.

FIGS. 19A-C provide schematic diagrams illustrating example infrastructures of multiple client devices and/or multiple enterprise locations within a collaborated cloud-based storage environment, in accordance with an implementation.

DETAILED DESCRIPTION OF THE ILLUSTRATIVE EMBODIMENTS

Figure 1:
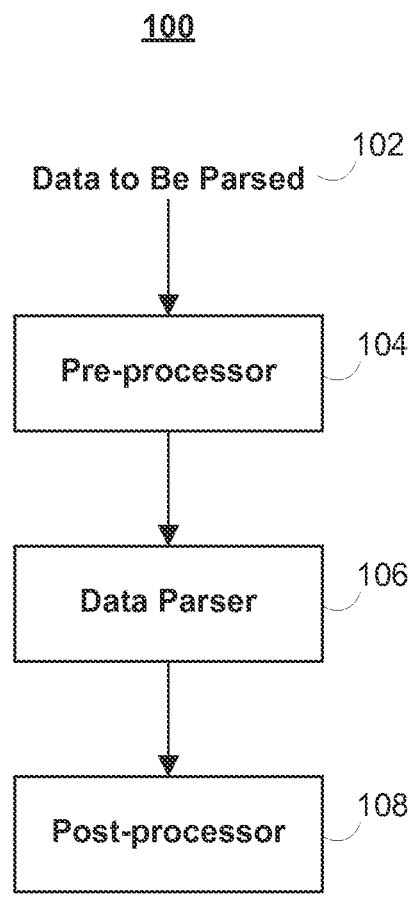
FIG. 1 illustrates a process for securing data including illustrative features that may be used in combination with any of the processes discussed herein, in accordance with an implementation.

Systems and methods described herein provide a gateway for managing cloud-based secure storage (e.g., by dynamically incorporating a local cache memory and one or more cloud-based storage servers into a storage volume for presentation to a client device). The volume may be presented to the client device as a virtual disk such that the locations that comprise the volume are hidden from the client device or an application running on the client device. The gateway may provision a storage volume demand for a client device (e.g., based on empirical file size associated with the client device). Based on the provisioned storage volume, the gateway generates a dynamically adjustable virtual disk incorporating cloud-based storage devices to virtually expand the storage capacity of the client device. In this way, the storage capacity of the virtual disk may be expanded dynamically when more storage space is needed, by incorporating additional cloud-based storage devices into the virtual disk. A user of the client device may store, read and write to data files in the virtual disk from the client device in a similar manner as working with a local memory, without the need to know an exact storage location of a specific data file.

According to one aspect, a cryptographic system is described herein where one or more secure servers store cryptographic keys and user authentication data. The cryptographic system may include a secure data parser either alone or in combination with other system components. As used herein, a secure data parser includes software and/or hardware configured to perform various functions relating to one or more of the parsing, securing, and storing of data. For example, the functions of the secure data parser may include any combination of encrypting data, parsing data into one or more shares, encrypting shares, dispersing shares, securely storing shares in multiple locations, retrieving data shares, decrypting data shares, reassembling data, decrypting data, or any other functions described herein. Parsing includes generating one or more distinct shares from an original data set where each of the shares includes at least a portion of the original data set. Parsing may be implemented by any of a number of techniques. For example, parsing may involve distributing data units from the original data set into one or more shares randomly, pseudo-randomly, deterministically, or using some suitable combination of random, pseudo-random, and deterministic techniques. A parsing operation may act on any size of data, including a single bit, a group of bits, a group of bytes, a group of kilobytes, a group of megabytes, or larger groups of data, as well as any pattern or combination of data unit sizes. Thus, the original data may be viewed as a sequence of these data units. In some implementations, the parsing operation is based on parsing information generated by the secure data parser or by another component in the cryptographic system. The parsing information may be in any suitable form (e.g., one or more keys including a predetermined, deterministic, pseudo-random or random key). The parsing information may determine one or more aspects of the parsing operation, including any combination of the number of shares, the size of one or more shares, the size of the data units, the order of the data units within the shares, and the order of the data from the original data set in the shares. In some embodiments, the parsing information may also indicate or may be used (among other factors) to determine how one or more data shares will be encrypted. While certain parsing techniques may render the data more secure (e.g., in some implementations, the size of the data units themselves may render the resulting data shares more secure, or the parsing may involve rearranging data data), this is not necessarily the case with every parsing technique. The resulting shares may be of any size of data, and two or more resulting shares may contain different amounts of the original data set.

In some implementations, parsing may include performing a cryptographic operation on the original data set before, during, or after generating the one or more shares. For example, parsing may involve shuffling the order of the data units in the share, e.g., by rearranging the units of data into the resulting share or shares. In some implementations, parsing may involve shuffling the order bits within each data unit, e.g., by rearranging sub-units within one or more data units that are distributed into the resulting share or shares, where a sub-unit includes at least a distinct portion of a data unit Where parsing involves shuffling data in the original data set, the shuffling operation may be performed on any size of the original data set, including the entire original data set, the one or more shares, the data units, a single bit, a group of bits, a group of bytes, a group of kilobytes, a group of megabytes, or larger groups of data, as well as any pattern or combination of data unit sizes. Shuffling data may involve distributing the original data into one or more shares in a way that shuffles the data, distributing the original data into one or more shares and then shuffling the data in the resulting share(s), shuffling the original data and then distributing the shuffled data into one or more shares, or any combination thereof.

Thus, the resulting shares may include a substantially random distribution of the original data set. As used herein, a substantially random distribution of data refers to generating one or more distinct shares from an original data set where at least one of the shares is generated using one or more random or pseudo-random techniques, random or pseudo-random information (e.g., a random or pseudo-random key), or any combination thereof. It will be understood that because generating a truly random number in a computer may not be practical, the use of a substantially random number will be sufficient. References to randomization herein is understood to include substantial randomization as when, for example, implemented using a computing device having limitations with regard to generating true randomization. As one example of data parsing that results in substantially random distribution of the original data into shares, consider an original data set 23 bytes in size, with the data unit size chosen to be one byte, and with the number of shares selected to be 4. Each byte would be distributed into one of the 4 shares. Assuming a substantially random distribution, a key would be obtained to create a sequence of 23 random numbers ($r_1$, $r_2$, $r_3$ through $r_{23}$), each with a value between 1 and 4 corresponding to the four shares. Each of the units of data (in this example, 23 individual bytes of data) is associated with one of the 23 random numbers corresponding to one of the four shares. The distribution of the bytes of data into the four shares would occur by placing the first byte of the data into share number $r_1$, byte two into share $r_2$, byte three into share $r_3$, through the $23^{rd}$ byte of data into share $r_{23}$. A wide variety of other possible steps or combination or sequence of steps, including adjusting the size of the data units, may be used in the parsing process. To recreate the original data, the reverse operation would be performed.

A parsing operation may add fault tolerance to the generated shares so that fewer than all of the shares are needed to restore the original data. For example, the parsing operation may provide sufficient redundancy in the shares such that only a subset of the shares is needed to reassemble or restore the data to its original or useable form. For example, the parsing may be done as a "3 of 4" parse, such that only three of the four shares are necessary to reassemble or restore the data to its original or useable form. This is also referred to as a "M of N parse" wherein N is the total number of shares, and M is at least one less than N.

FIG. 1 shows an illustrative secure data parsing system (also referred to herein as a secure data parser) 100. The secure data parsing system 100 may be implemented using hardware and/or software such as a parser program or software suite. The secure data parser may further include or interface with one or more data storage facilities and other hardware or software modules from which data may be received or transmitted and which may perform various functions on the data. The system 100 may include one or more of pre-processors 104, one or more data parsers 106, and one or more post-processors 108. All of features described with respect to the system 100 are optional and the operations performed by pre-processor 104, data parser 106, and post-processor 108 may be performed in any possible combination or order. The secure data parser 100 receives data to be secured 102 and passes the data to a pre-processor 104 that may perform any combination of pre-processing operations on the received data 102, such as encrypting the data, adding integrity information (e.g., a hash) to the data, and adding authentication information to the data. The pre-processing may alternatively or additionally involve accessing and/or generating one or more keys or other information used by the secure data parser 100. The one or more keys may be any suitable key(s) for generating distinct portions of data from an original data set and/or any suitable key for other operations described herein that are performed by the secure data parser 100. The key(s) may be generated randomly, pseudo-randomly, or deterministically. These and other pre-processing operations are described further herein.

After any desired pre-processing, the (optionally transformed) data 102 and any additional information, such as any suitable keys, are passed to a data parser 106. Data parser 106 may parse the received data to generate one or more shares from the data 102 using any of the parsing techniques described herein. The data parser 106 may use any suitable key for data parsing.

In some implementations, data parser 106 involves parsing one or more keys used in the encryption or parsing of the data. Any of the above-described parsing techniques may be used parse any key. In some embodiments, parsing a key causes the key to be stored in one or more shares, of the parsed data 102. In other embodiments, the key shares resulting from a key parsing operation are stored separately from the data shares resulting from the data parsing operation. These and other features and functions that may be performed by data parser 106 are described further herein.

After parsing the data and/or any keys, the parsed data and keys may be post-processed by one or more post-processors 108. The post-processor 108 may perform any one or more operations on the individual received data shares, such as encrypting one or more data shares, adding integrity information (e.g., a hash) to one or more shares, and adding authentication information to one or more shares. Post-processor 108 may also perform any one or more operations on the received keys or key shares, such as encrypting one or more keys or key shares, adding integrity information (e.g., a hash) to one or more keys or key shares, and adding authentication information to one or more keys or key shares. Post-process may also direct the data shares, keys, and/or key shares to be transmitted or stored. These and other features and functions that may be performed by post-processor 108 are described further herein.

The combination and order of processes used by the secure data parser 100 may depend on the particular application or use, the level of security desired, whether optional pre-encryption, post-encryption, or both, are desired, the redundancy desired, the capabilities or performance of an underlying or integrated system, or any other suitable factor or combination of factors.

In one implementation, the data parser 106 parses the data to generate four or more shares of data or keys, and the post-processor 108 encrypts all of the shares, then stores these encrypted shares in different locations in the database from which they were received. Alternatively or additionally, the post-processor 108 may relocate the encrypted shares to any of one or more suitable storage devices, which may be fixed or removable, depending on the requestor's need for privacy and security. In particular, the encrypted shares may be stored virtually anywhere, including, but not limited to, a single server or data storage device, or among separate data storage facilities or devices. Management of any keys used by the secure data parser 100 may be handled by the secure data parser 100, or may be integrated into an existing infrastructure or any other desired location. The retrieval, recombining, reassembly or reconstituting of the encrypted data shares may also utilize any number of authentication techniques, including, but not limited to, biometrics, such as fingerprint recognition, facial scan, hand scan, iris scan, retinal scan, ear scan, vascular pattern recognition or DNA analysis.

Traditional encryption technologies rely on one or more keys used to encrypt the data and render it unusable without the one or more keys. The data, however, remains whole and intact and subject to attack. In some embodiments, the secure data parser addresses this problem by parsing the encrypted file into two or more shares, adding another layer of encryption to each share of the data, and then storing the shares in different physical and/or logical locations. When one or more data shares are physically removed from the system, either by using a removable device, such as a data storage device, or by placing the share under another party's control, any possibility of compromise of secured data is effectively removed. In some embodiments, the encrypted file is parsed into four or more portions or shares.

Figure 2:
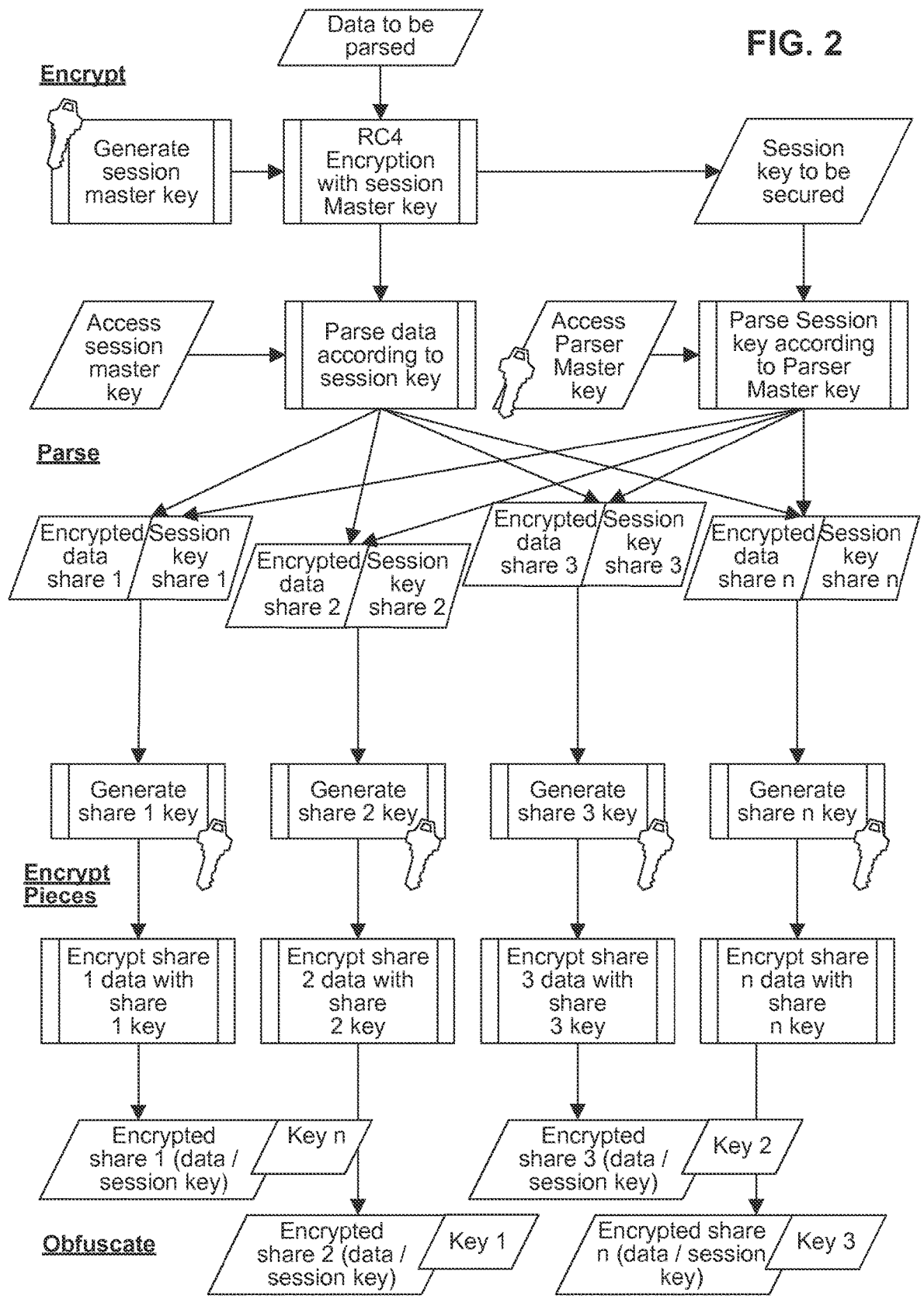
FIG. 2 illustrates a process for parsing data with encryption and storage of the encryption master key with the data in accordance with an implementation.

One example of a secure data parser is shown in FIG. 2, which shows the following steps of a process performed by the secure data parser on the data to be parsed, resulting in storing a session master key with the parsed data:

1. Generating a session master key and encrypting the data using, for example, the RS1 or the RC4 stream cipher.

2. Parsing the resulting encrypted data into four data shares according to the pattern of the session master key.

3. Parsing the session master key according to the pattern of a Parser Master Key and appending the resulting key shares to the data shares. The resulting four shares of data will contain portions of the encrypted original data and portions of the session master key. In other embodiments, the session master key is not stored with the data shares (see, e.g., FIG. 3 and accompanying discussions).

4. Generating a stream cipher key for each of the four shares.

5. Encrypting each share with its respective stream cipher key, then storing the encryption keys in different locations from the encrypted shares. As shown in FIG. 2, Share 1 is stored with Key 4, Share 2 is stored with Key 1, Share 3 is stored with Key 2, and Share 4 is stored with Key 3. However, any other pairing of keys with shares may be used, including, for example, arrangements in which more than one key is stored with a particular share, or in which the same key is parsed and stored across multiple shares.

To restore the original data format, the above steps are reversed. For example, to restore the original data in the example of FIG. 2, a sufficient number of the shares are retrieved. In implementations where the parsing operation includes redundancy, the original data may be restored from a minimum number of the total number of shares, which is less than the total number of shares. Thus, the original data may be restored from any suitable number of shares which, in this example, may range from one to four, depending on the parsing operation used. The cipher keys for each of the retrieved shares are also received. Each share may be decrypted with the stream cipher key that was used to encrypt the respective share. The session master key may be retrieved, or key shares of the parsed session master key are also retrieved from the shares. As with the data shares, the session master key may be restored from a minimum number (that may be less than or equal to all) of the total key shares, depending on key parsing operation used. The session master is restored from the key shares by reversing the key parsing operation. The data shares retrieved from the shares may also be restored by reversing the data parsing operation, which may involve the use of the retrieved or restored session master key. If the data restored by reversing the parse operation had been encrypted before parsing, the original data may be revealed by decrypting the restored data. Further processing may be performed on the data as needed.

In the above example, the secure data parser may be implemented with external session key management or secure internal storage of session keys. Upon implementation, the Parser Master Key for securing the application and for encryption purposes is generated. The incorporation of the Parser Master key in the resulting shares allows for a flexibility of sharing of secured data by individuals within a workgroup, enterprise or extended audience.

Figure 3:
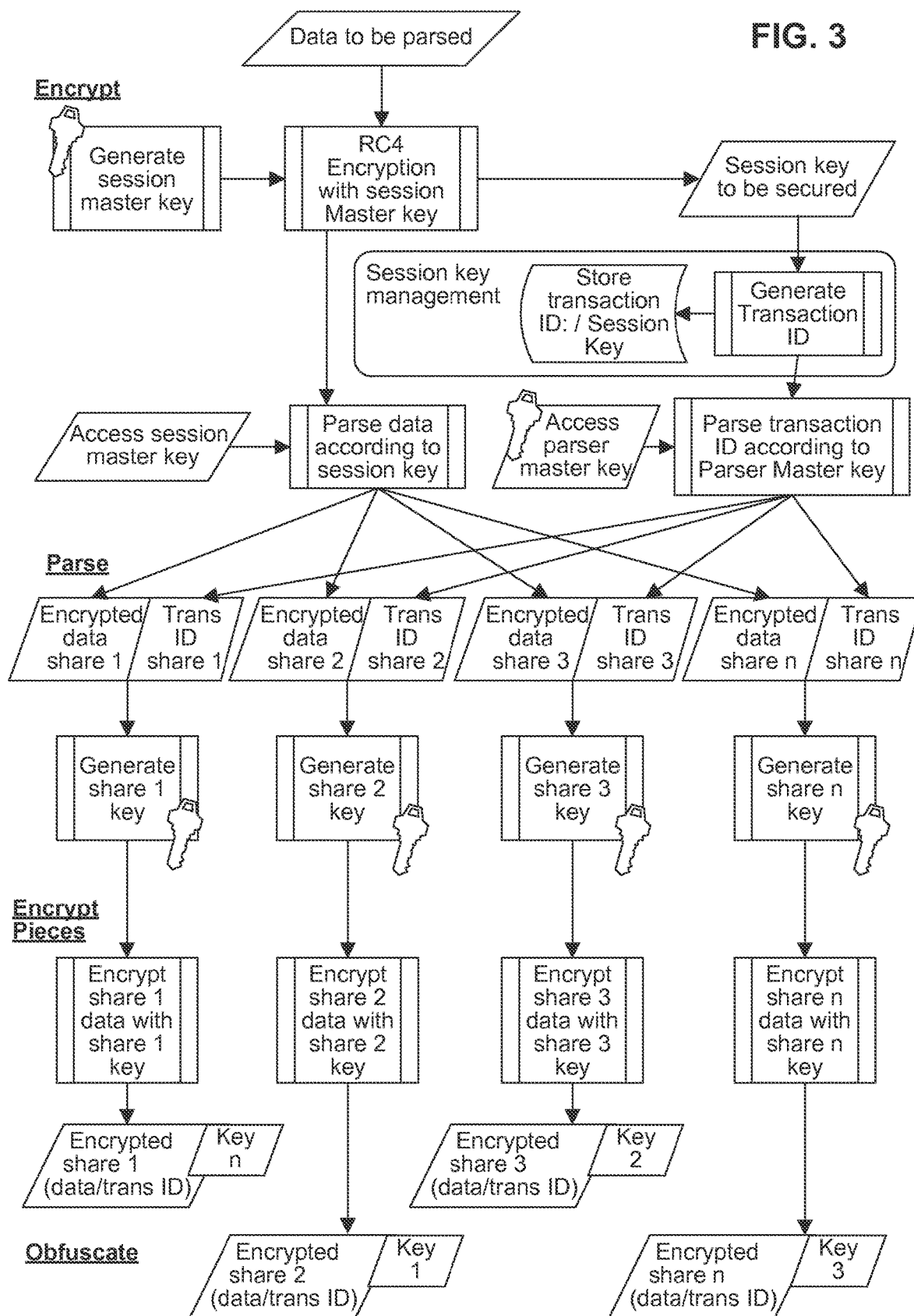
FIG. 3 illustrates a process for parsing data with encryption and storing the encryption master key separately from the data in accordance with an implementation.

FIG. 3 depicts another example of the secure data parser, including another process that may be performed by the secure data parser, resulting in storing the session master key data in one or more separate key management tables. The steps of generating a session master key, encrypting the data to be parsed with the session master key, and parsing the resulting encrypted data into four shares or portions of parsed data according to the pattern of the session master key are similar to the corresponding steps described above in relation to FIG. 2.

In this example, the session master key will be stored in a separate key management table in a data depository. A unique transaction ID is generated for this transaction. The transaction ID and session master key are stored in the separate key management table. The transaction ID is parsed according to the pattern of the Parser Master Key, and shares of the transaction ID are appended to the encrypted parsed data. The resulting four shares will contain encrypted portions of the original data and portions of the transaction ID.

As in FIG. 2, a stream cipher key is generated for each of the four data shares, each share is encrypted with its respective stream cipher key, and the encryption keys used to encrypt the data shares are stored separately from the data shares (e.g., in different locations from the encrypted data shares). To restore the original data, the steps are reversed.

Figure 4:
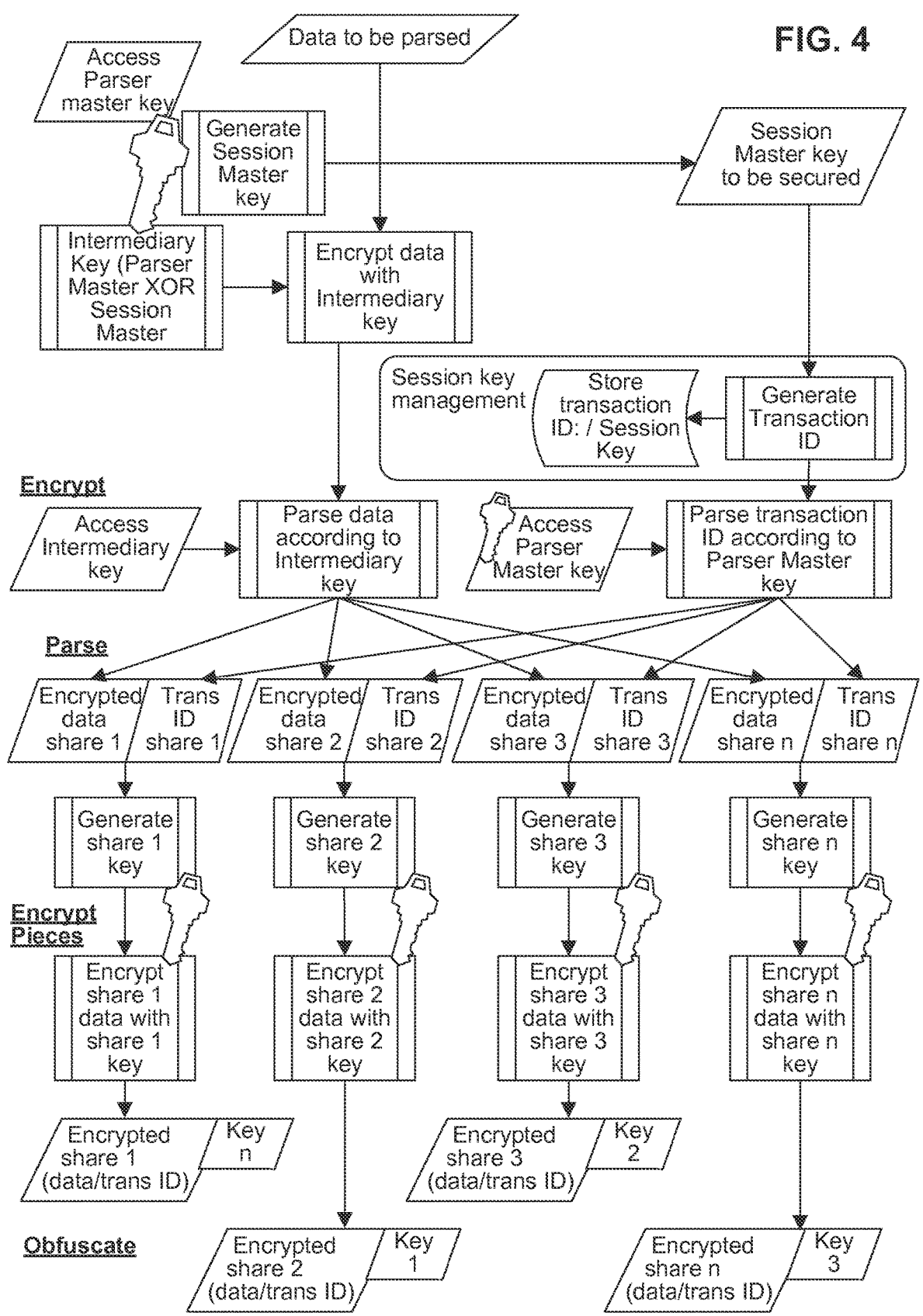
FIG. 4 illustrates the intermediary key process for parsing data with encryption and storage of the encryption master key with the data in accordance with an implementation.

FIG. 4 depicts another example of the secure data parser, including another process that may be performed by a secure data parser on the data to be parsed. This example involves use of an intermediary key. The process includes the following steps:

1. Accessing a Parser Master Key associated with the authenticated user.

2. Generating a unique Session Master key.

3. Deriving an Intermediary Key, for example, using an exclusive OR (XOR) function of the Parser Master Key and Session Master key.

4. Optionally encrypting the data using an encryption algorithm keyed with the Intermediary Key.

5. Parsing the optionally encrypted data into four shares of parsed data according to the pattern of the Intermediary Key.

6. Generating a unique transaction ID and storing the transaction ID and session master key in a separate key management table.

7. Parsing the transaction ID according to the pattern of the Parser Master Key.

8. Appending shares of the transaction ID to the shares of parsed data. The resulting combined shares will contain optionally encrypted portions of the original data and portions of the session master key.

9. Optionally generating an encryption key for each of the four data shares.

10. Optionally encrypting each share with an existing or new encryption algorithm, and then storing the encryption keys in different locations from the combined shares. As shown in FIG. 4, Share 1 is stored with Key 4, Share 2 is stored with Key 1, Share 3 is stored with Key 2, and Share 4 is stored with Key 3.

To restore the original data format, the steps are reversed.

In some embodiments, the above steps 6-8 above may be replaced by the following steps:

6. Storing the Session Master Key along with the secured data shares in a data depository.

7. Parsing the session master key according to the pattern of the Parser Master Key.

8. Appending the key data to the optionally encrypted shares.

Certain steps of the methods described herein (e.g., the steps described for any of the methods depicted in FIGS. 2-4) may be performed in different order, or repeated multiple times, as desired. It is also readily apparent to those skilled in the art that the portions of the data may be handled differently from one another. For example, multiple parsing steps may be performed on only one portion of the parsed data. Each portion of parsed data may be uniquely secured in any desirable way provided only that the data may be reassembled, reconstituted, reformed, decrypted or restored to its original or other usable form. It is understood that one or more of these methods may be combined in the same implementation without departing from the scope of the disclosure.

The data secured according to the methods described herein is readily retrievable and restored, reconstituted, reassembled, decrypted, or otherwise returned into its original or other suitable form for use. In order to restore the original data, the following items may be utilized:

1. Some or all shares or portions of the data set.
2. Knowledge of and ability to reproduce the process flow of the method used to secure the data.
3. Access to the session master key.
4. Access to the Parser Master Key.

In some embodiments, not all of these items may be required to retrieve and restore, reconstitute, reassemble, decrypt, or otherwise return into the original or other suitable form for use, every unit of data secured according to one or more of the above-described methods. In some embodiments, additional items not expressly listed above may be required to restore a particular unit of data. For example, in some implementations, the above-described methods use three types of keys for encryption. Each type of key may have individual key storage, retrieval, security and recovery options, based on the installation. The keys that may be used include, but are not limited to:

1. The Parser Master Key may be an individual key associated with the installation of the secure data parser. It is installed on the server on which the secure data parser has been deployed. There are a variety of options suitable for storing this key including, but not limited to, a smart card, separate hardware key store, standard key stores, custom key stores or within a secured database table, for example.

2. The Session Master Key may be generated each time data is parsed. The Session Master Key is used to encrypt the data prior to the parsing operations. It may also be used (if the Session Master Key is not integrated into the parsed data) for parsing the encrypted data. The Session Master Key may be stored in a variety of manners, including, but not limited to, a standard key store, custom key store, separate database table, or secured within the encrypted shares, for example.

3. The Share Encryption Keys: For each share or portions of a data set that is created, an individual Share Encryption Key may be generated to further encrypt the shares. The Share Encryption Keys may be stored in different shares than the share that was encrypted.

As shown in FIG. 4, an Intermediary Key may also be utilized. The Intermediary Key may be generated each time data is parsed. The Intermediary Key is used to encrypt the data prior to the parsing operations. It may also be incorporated as a means of parsing the encrypted data.

Figure 5:
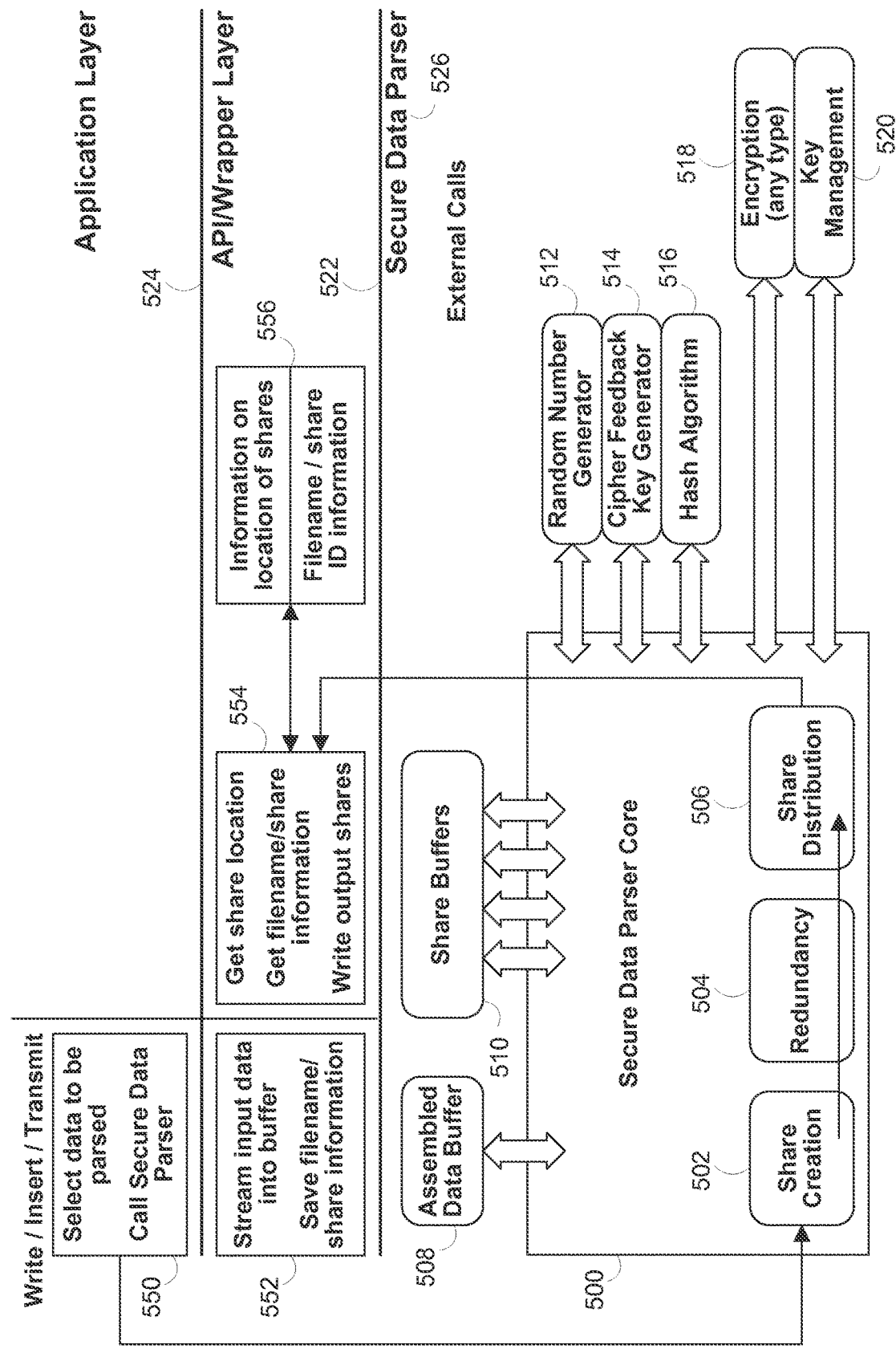
FIGS. 5 and 6 are block diagrams of an illustrative system having the secure data parser integrated in accordance with an implementation.

FIG. 5 shows an illustrative implementation of the secure data parser as secure data parser 500. Secure data parser 500 may include built-in capabilities for parsing data into shares using module 502. Secure data parser 500 may also include built in capabilities in module 504 for performing redundancy in order to be able to implement, for example, the M of N parse described above. Secure data parser 500 may also include share distribution capabilities using module 506 for placing the shares into buffers from which they are sent for communication to a remote location, for storage, etc. It will be understood that any other suitable capabilities may be built into secure data parser 500.

Assembled data buffer 508 may be any suitable memory used to store the original data (although not necessarily in its original form) that will be parsed by secure data parser 500. In a parsing operation, assembled data buffer 508 provides input to secure data parser 500. In a restore operation, assembled data buffer 508 may be used to store the output of secure data parser 500.

Share buffers 510 may be one or more memory modules that may be used to store the multiple shares of data that resulted from the parsing of original data. In a parsing operation, share buffers 510 hold the output of the secure data parser. In a restore operation, share buffers hold the input to secure data parser 500.

It will be understood that any other suitable arrangement of capabilities may be built-in for secure data parser 500. Any additional features may be built-in and any of the features illustrated may be removed, made more robust, made less robust, or may otherwise be modified in any suitable way. Buffers 508 and 510 are likewise merely illustrative and may be modified, removed, or added to in any suitable way.

Any suitable modules implemented in software, hardware or both may be called by or may call to secure data parser 500. As illustrated, some external modules include random number generator 512, cipher feedback key generator 514, hash algorithm 516, any one or more types of encryption 518, and key management 520. It will be understood that these are merely illustrative external modules. Any other suitable modules may be used in addition to or in place of those illustrated. If desired, one or more external modules may replace capabilities that are built into secure data parser 500.

Cipher feedback key generator 514 may generate, for each secure data parser operation, a unique key, or random number (using, for example, random number generator 512), to be used as a seed value for an operation that extends an original session key size (e.g., a value of 128, 256, 512, or 1024 bits) into a value equal to the length of the data to be parsed. Any suitable algorithm may be used for the cipher feedback key generation, such as the AES cipher feedback key generation algorithm.

In order to facilitate integration of secure data parser 500 and its external modules (i.e., secure data parser layer 526) into an application layer 524 (e.g., an email application or database application), a wrapping layer that may use, for example, API function calls may be used. Any other suitable arrangement for integrating secure data parser layer 526 into application layer 524 may be used.

FIG. 5 also shows how the secure data parser 500 and external modules may be used when a write (e.g., to a storage device), insert (e.g., in a database field), or transmit (e.g., across a network) command is issued in application layer 524. At step 550 data to be parsed is identified and a call is made to the secure data parser. The call is passed through wrapper layer 522 where at step 552, wrapper layer 522 streams the input data identified at step 550 into assembled data buffer 508. Also at step 552, any suitable share information, filenames, any other suitable information, or any combination thereof may be stored (e.g., as information 556 at wrapper layer 522). Secure data processor 500 then parses the data it takes as input from assembled data buffer 508. It outputs the data shares into share buffers 510. At step 554, wrapper layer 522 obtains from stored information 556 any suitable share information (i.e., stored by wrapper 522 at step 552) and share location(s) (e.g., from one or more configuration files). Wrapper layer 522 then writes the output shares (obtained from share buffers 510) appropriately (e.g., written to one or more storage devices, communicated onto a network, etc.).

Figure 6:
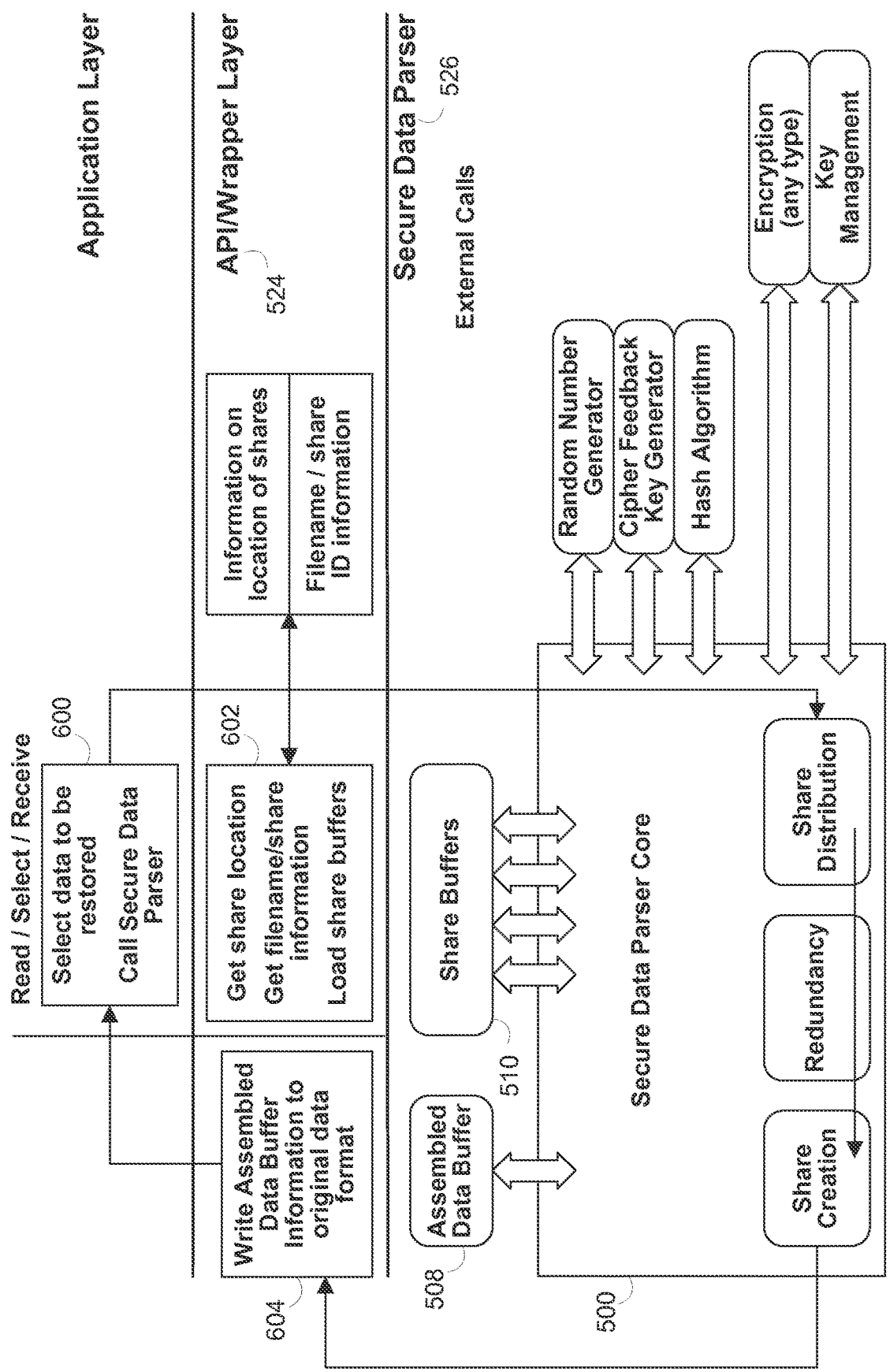

FIG. 6 shows how the secure data parser 500 and external modules may be used when a read (e.g., from a storage device), select (e.g., from a database field), or receive (e.g., from a network) occurs. At step 600, data to be restored is identified and a call to secure data parser 500 is made from application layer 524. At step 602, from wrapper layer 522, any suitable share information is obtained and share location is determined. Wrapper layer 522 loads the portions of data identified at step 600 into share buffers 510. Secure data parser 500 then processes these shares as described herein (e.g., if only three of four shares are available, then the redundancy capabilities of secure data parser 500 may be used to restore the original data using only the three shares). The restored data is then stored in assembled data buffer 508. At step 504, application layer 522 converts the data stored in assembled data buffer 508 into its original data format (if necessary) and provides the original data in its original format to application layer 524.

Figure 7:
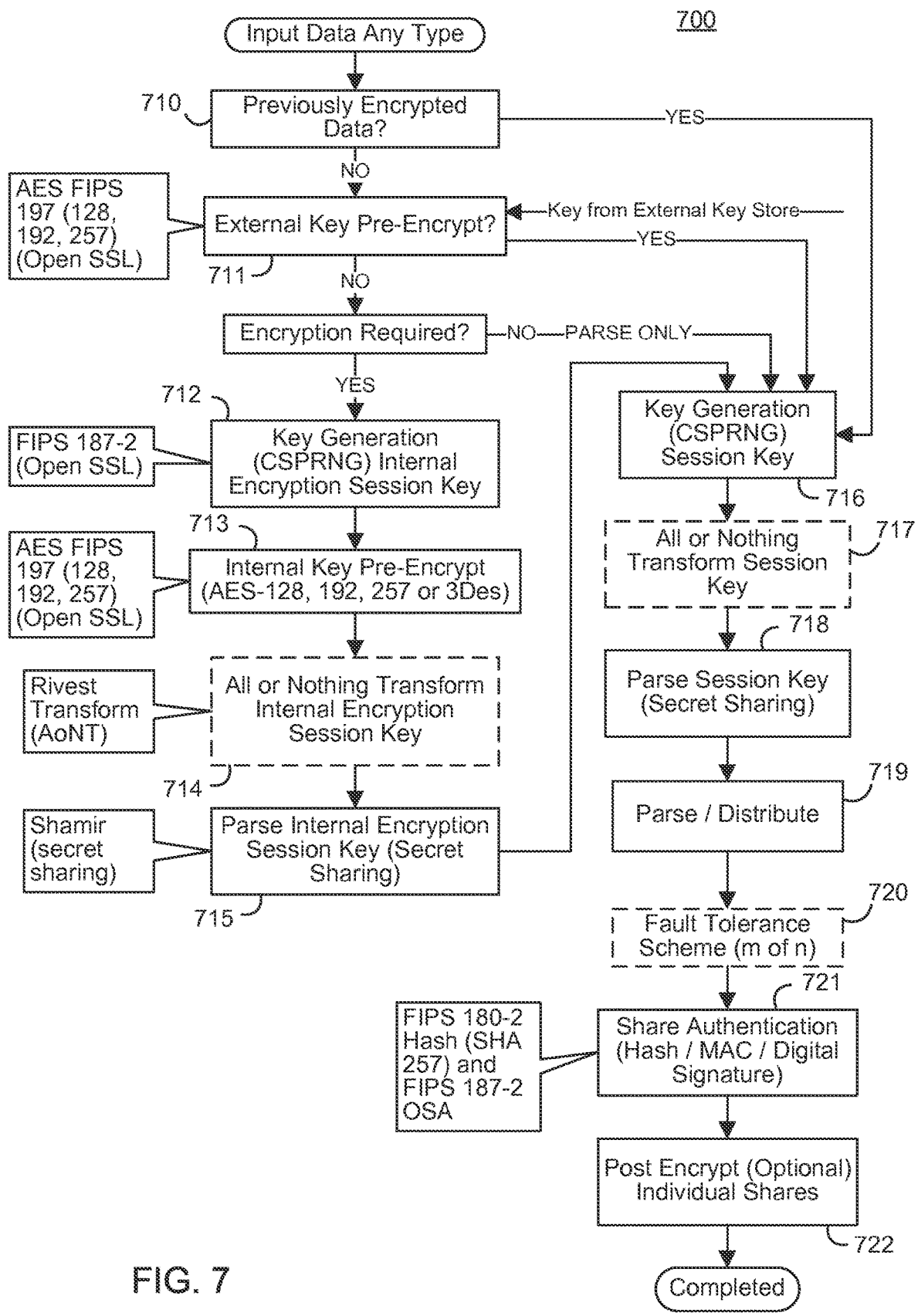
FIG. 7 is a process flow diagram of illustrative steps and features that may be used in any suitable combination, with any suitable additions, deletions, or modifications in accordance with an implementation.

FIG. 7 depicts example options 700 for using the components of the secure data parser. Several exemplary combinations of options are outlined below in reference to FIG. 7. As described in relation to FIGS. 5 and 6, the secure data parser may be modular in nature, allowing for any known algorithm to be used within each of the function blocks shown in FIG. 7. The labels shown in the example of FIG. 7 merely depict one possible combination of algorithms. Any suitable algorithm or combination of algorithms may be used in place of the labeled algorithms. For example, other key parsing (e.g., secret sharing) algorithms such as Blakely may be used in place of Shamir, or the AES encryption could be replaced by other known encryption algorithms such as Triple DES.

1) 710, 716, 717, 718, 719, 720, 721, 722

If previously encrypted data is received at step 710, the data may be parsed into a predefined number of shares. If the parse algorithm requires a key, a session key may be generated at step 716 using a cryptographically secure pseudo-random number generator. The session key may optionally be transformed using an All or Nothing Transform (AoNT) into a transform session key at step 717 before being parsed into the predefined number of shares with fault tolerance at step 718. The data may then be parsed into the predefined number of shares at step 719. A fault tolerant scheme may be used at step 720 to allow for regeneration of the data from less than the total number of shares. Once the shares are created, authentication/integrity information may be embedded into the shares at step 721. Each share may be optionally post-encrypted at step 722.

2) 711, 716, 717, 718, 719, 720, 721, 722

In some embodiments, the input data may first be encrypted using a pre-encryption key provided by a user or an external system before the data is parsed. An external pre-encryption key is provided at step 711. For example, the key may be provided from an external key store. If the parse algorithm requires a key, the session key may be generated using a cryptographically secure pseudo-random number generator at step 716. The session key may optionally be transformed using an All or Nothing Transform (AoNT) into a transform session key at step 717 before being parsed into the predefined number of shares with fault tolerance at step 718. The data is then parsed to a predefined number of shares at step 719. A fault tolerant scheme may be used at step 720 to allow for regeneration of the data from less than the total number of shares. Once the shares are created, authentication/integrity information may be embedded into the shares at step 721. Each share may be optionally post-encrypted at step 722.

3) 712, 713, 714, 715, 716, 717, 718, 719, 720, 721, 722

In some embodiments, encryption is required but an external key for the pre-encryption is not used. In such embodiments, an encryption key may be generated using a cryptographically secure pseudo-random number generator at step 712 to transform the data. Encryption of the data using the generated encryption key may occur at step 713. The encryption key may optionally be transformed using an All or Nothing Transform (AoNT) into a transform encryption key at step 714. The transform encryption key and/or generated encryption key may then be parsed into the predefined number of shares with fault tolerance at step 715. If the parse algorithm requires a key, generation of the session key using a cryptographically secure pseudo-random number generator may occur at step 716. The session key may optionally be transformed using an All or Nothing Transform (AoNT) into a transform session key at step 717 before being parsed into the predefined number of shares with fault tolerance at step 718. The data may then be parsed into a predefined number of shares at step 719. A fault tolerant scheme may be used at step 720 to allow for regeneration of the data from less than the total number of shares. Once the shares are created, authentication/integrity information will be embedded into the shares at step 721. Each share may then be optionally post-encrypted at step 722.

The secure data parser may offer flexible data protection by facilitating physical separation. Data may be first encrypted, then parsed into shares with "m of n" fault tolerance. This allows for regeneration of the original information when less than the total number of shares is available. For example, some shares may be lost or corrupted in transmission. The lost or corrupted shares may be recreated from fault tolerance or integrity information appended to the shares, as discussed in more detail below.

In order to create the shares, a number of keys are optionally utilized by the secure data parser described above. These keys may include one or more of the following:

Pre-encryption key: When pre-encryption of the shares is selected, an external encryption key may be passed to the secure data parser. This key may be generated and stored externally in a key store (or other location) and may be used to optionally encrypt data prior to parsing the data.

Internal encryption key: This key may be generated internally and used by the secure data parser to encrypt the data prior to parsing. This key may then be stored securely within the shares using a key parsing algorithm.

Session key: This key is not used with an encryption algorithm; rather, it may be used to key the data partitioning algorithms when random parsing is selected. When a random parse is used, a session key may be generated internally and used by the secure data parser to partition the data into shares. This key may be stored securely within the shares using a key parsing algorithm.

Post encryption key: When post encryption of the shares is selected, an external key may be passed to the secure data parser and used to post encrypt the individual shares. This key may be generated and stored externally in a key store or other suitable location.

In some embodiments, when data is secured using the secure data parser in this way, the information may only be reassembled provided that all of the required shares and external encryption keys are present.

In addition to the individual protection of information assets, there is sometimes a requirement to share information among different groups of users or communities of interest. It may then be necessary to either control access to the individual shares within that group of users or to share credentials among those users that would only allow members of the group to reassemble the shares. To this end, a workgroup key may be deployed to group members. The workgroup key should be protected and kept confidential, as compromise of the workgroup key may potentially allow those outside the group to access information. The workgroup key concept allows for enhanced protection of information assets by encrypting key information stored within the shares. Once this operation is performed, even if all required shares and other external keys are discovered, an attacker has no hope of recreating the information without access to the workgroup key.

Figure 8:
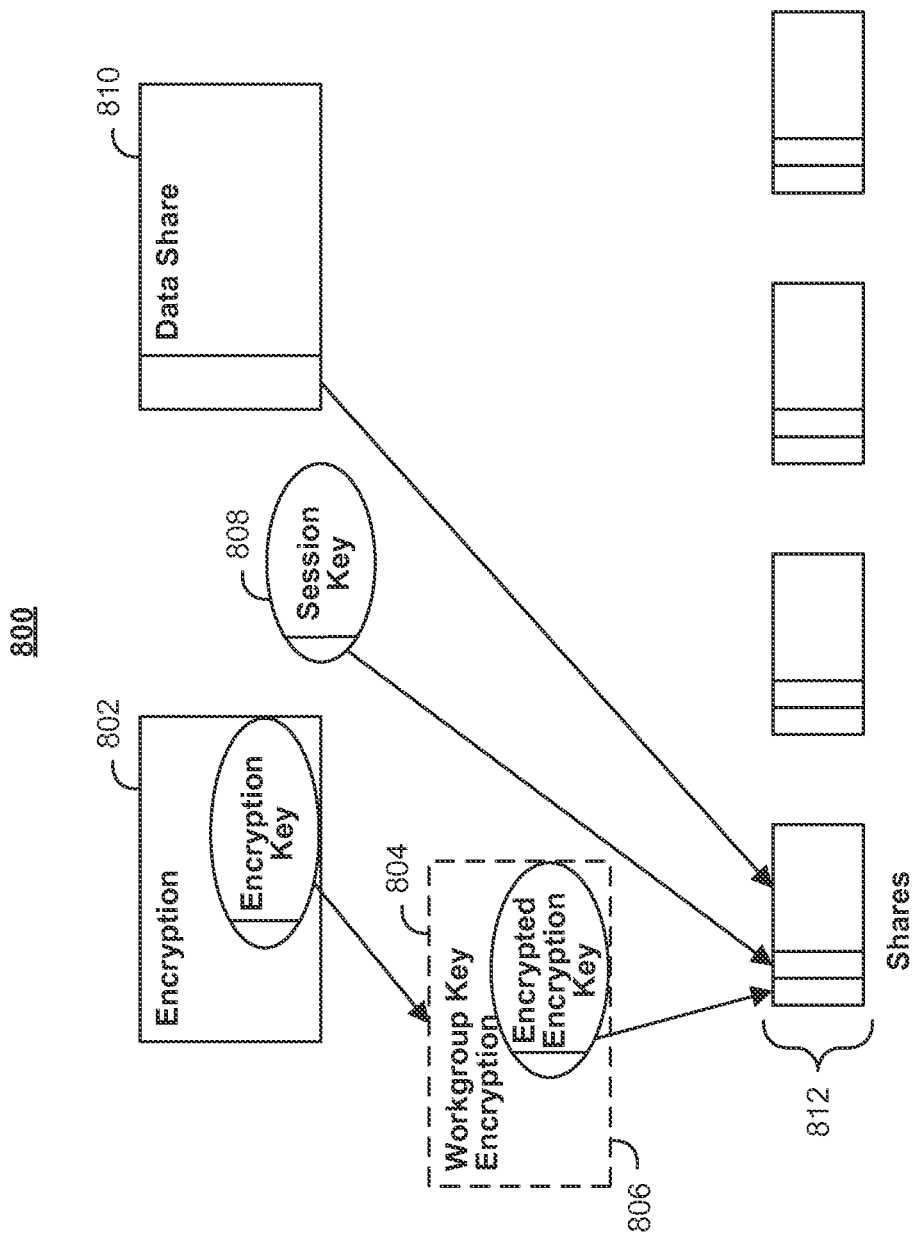
FIG. 8 is a simplified block diagram of the storage of key and data components within shares, optionally using a workgroup key, that may be used in any suitable combination, with any suitable additions, deletions, or modifications in accordance with one implementation.

FIG. 8 shows illustrative block diagram 800 for storing key and data components within the shares. In the example of diagram 800, the optional pre-encrypt and post-encrypt steps are omitted, although these steps may be included in other embodiments.

The simplified process to parse the data includes first encrypting the data using an encryption key at encryption stage 802. The encryption key may then optionally be encrypted with a workgroup key at stage 804. The encryption key, optionally encrypted by the workgroup key, may then be parsed into shares and stored within data shares 812. Session key 808 may also be parsed and stored within shares 812. Using the session key, encrypted data 810 is parsed and stored in shares 812.

In order to restore the data, the session key portions may be retrieved from the shares 812 and restored. The parsing operation of the data may then be reversed to restore the encrypted data. The shares of the encryption key (which was encrypted with the workgroup key) may be retrieved and the encrypted encryption key restored. The encrypted encryption key may then be decrypted using the workgroup key. Finally, the encrypted data may then be decrypted using the encryption key to reveal the original data.

There are several secure methods for deploying and protecting workgroup keys. The selection of which method to use for a particular application depends on a number of factors. These factors may include security level required, cost, convenience, and the number of users in the workgroup. Exemplary techniques include hardware-based key storage and software-based key storage.

Hardware-based solutions generally provide the strongest guarantees for the security of encryption/decryption keys in an encryption system. Examples of hardware-based storage solutions include tamper-resistant key token devices that store keys in a portable device (e.g., smartcard/dongle), or non-portable key storage peripherals. These devices are designed to prevent easy duplication of key material by unauthorized parties. Keys may be generated by a trusted authority and distributed to users, or generated within the hardware. Additionally, key storage systems may provide multi-factor authentication, where use of the keys requires access both a physical object (token) and a passphrase or biometric. While dedicated hardware-based storage may be desirable for high-security deployments or applications, other deployments may elect to store keys directly on local hardware (e.g., disks, RAM or non-volatile RAM stores such as USB drives). This provides a lower level of protection against insider attacks, or in instances where an attacker is able to directly access the encryption machine.

To secure keys on disk, software-based key management often protects keys by storing them in encrypted form under a key derived from a combination of other authentication metrics, including: passwords and passphrases, presence of other keys (e.g., from a hardware-based solution), biometrics, or any suitable combination. The level of security provided by such techniques may range from the relatively weak key protection mechanisms provided by some operating systems (e.g., MS Windows and Linux) to more robust solutions implemented using multi-factor authentication.

The secure data parser described herein may be advantageously used in a number of applications and technologies. For example, email system, RAID systems, video broadcasting systems, database systems, tape backup systems, or any other suitable system may have the secure data parser integrated at any suitable level. As previously discussed, it will be understand that the secure data parser may also be integrated for protection and fault tolerance of any type of data in motion through any transport medium, including, for example, wired, wireless, or physical transport mediums. As one example, voice over Internet protocol (VoIP) applications may make use of the secure data parser to solve problems relating to echoes and delays that are commonly found in VoIP. The need for network retry on dropped packets may be eliminated by using fault tolerance, which guarantees packet delivery even with the loss of a predetermined number of shares. Packets of data (e.g., network packets) may also be efficiently parsed and restored "on-the-fly" with minimal delay and buffering, resulting in a comprehensive solution for various types of data in motion. The secure data parser may act on network data packets, network voice packets, file system data blocks, or any other suitable unit of information. In addition to being integrated with a VoIP application, the secure data parser may be integrated with a file-sharing application (e.g., a peer-to-peer file-sharing application), a video broadcasting application, an electronic voting or polling application (which may implement an electronic voting protocol and blind signatures, such as the Sensus protocol), an email application, or any other network application that may require or desire secure communication.

Figure 9B:
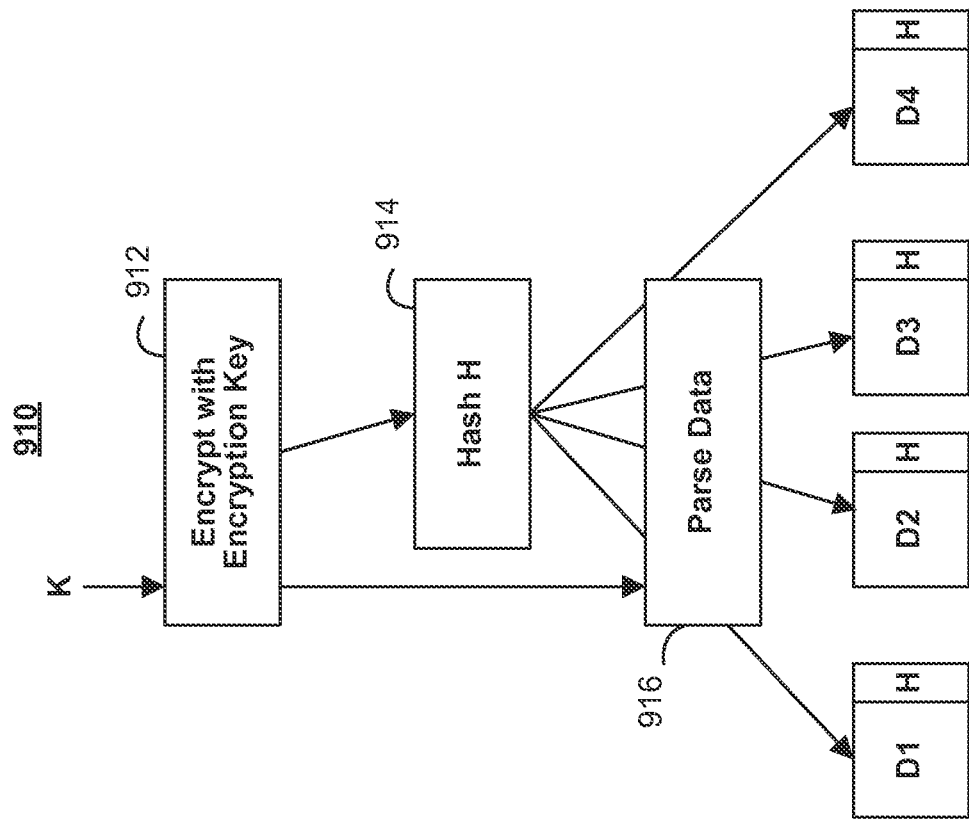
FIGS. 9A and 9B are simplified and illustrative process flow diagrams for header generation and data splitting for data in motion that may be used in any suitable combination, with any suitable additions, deletions, or modifications in accordance with one implementation.
Figure 9A:
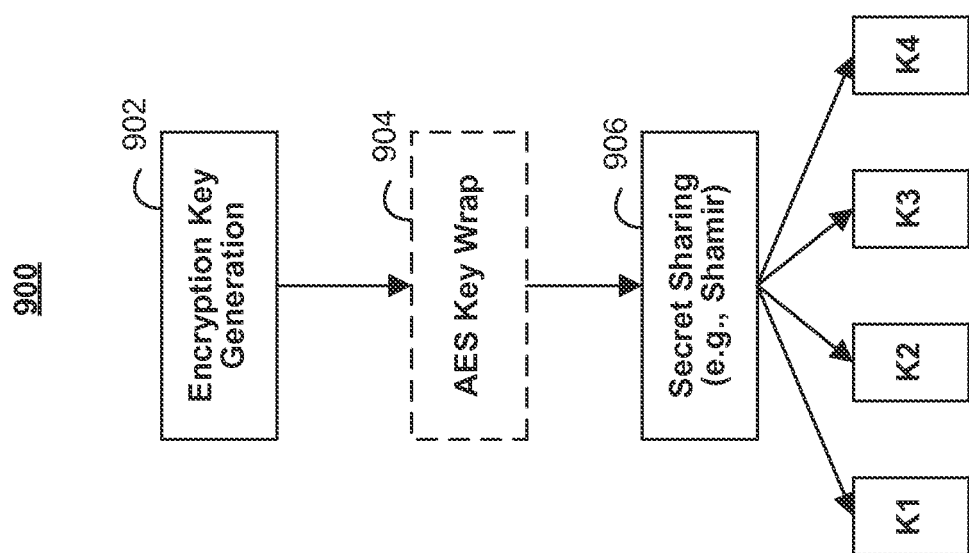

In some embodiments, support for network data in motion may be provided by the secure data parser in two distinct phases—a header generation phase and a data parsing phase. Simplified header generation process 900 and simplified data parsing process 910 are shown in FIGS. 9A and 9B, respectively. One or both of these processes may be performed on network packets, file system blocks, or any other suitable information.

In some embodiments, header generation process 900 may be performed once at the initiation of a network packet stream. At step 902, a random (or pseudo-random) encryption key, K, may be generated. The encryption key, K, may then be optionally encrypted (e.g., using the workgroup key described above) at AES key wrap step 904. Although an AES key wrap may be used in some embodiments, any suitable key encryption or key wrap algorithm may be used in other embodiments. AES key wrap step 904 may operate on the entire encryption key, K, or the encryption key may be parsed into several blocks (e.g., 64-bit blocks). AES key wrap step 904 may then operate on blocks of the encryption key, if desired.

At step 906, a secret sharing algorithm (e.g., Shamir) may be used to parse the encryption key, K, into key shares. Each key share may then be embedded into one of the output shares (e.g., in the share headers). Finally, a share integrity block and (optionally) a post-authentication tag (e.g., MAC) may be appended to the header block of each share. Each header block may be designed to fit within a single data packet.

After header generation is complete (e.g., using simplified header generation process 900), the secure data parser may enter the data partitioning phase using simplified data parsing process 910. Each incoming data packet or data block in the stream is encrypted using the encryption key, K, at step 912. At step 914, share integrity information (e.g., a hash H) may be computed on the resulting ciphertext from step 912. For example, a SHA-256 hash may be computed. At step 916, the data packet or data block may then be partitioned into two or more data shares using one of the data parsing algorithms described above. In some embodiments, the data packet or data block may be parsed so that each data share contains a substantially random distribution of the encrypted data packet or data block. The integrity information (e.g., hash H) may then be appended to each data share. An optional post-authentication tag (e.g., MAC) may also be computed and appended to each data share in some embodiments.

Each data share may include metadata, which may be necessary to permit correct reconstruction of the data blocks or data packets. This information may be included in the share header. The metadata may include such information as cryptographic key shares, key identities, share nonces, signatures/MAC values, and integrity blocks. In order to maximize bandwidth efficiency, the metadata may be stored in a compact binary format.

For example, in some embodiments, the share header includes a cleartext header chunk, which is not encrypted and may include such elements as the Shamir key share, per-session nonce, per-share nonce, key identifiers (e.g., a workgroup key identifier and a post-authentication key identifier). The share header may also include an encrypted header chunk, which is encrypted with the encryption key. An integrity header chunk, which may include integrity checks for any number of the previous blocks (e.g., the previous two blocks), may also be included in the header. Any other suitable values or information may also be included in the share header.

As shown in illustrative share format 1000 of FIG. 10, header block 1002 may be associated with two or more output blocks 1004. Each header block, such as header block 1002, may be designed to fit within a single network data packet. In some embodiments, after header block 1002 is transmitted from a first location to a second location, the output blocks may then be transmitted. Alternatively, header block 1002 and output blocks 1004 may be transmitted at the same time in parallel. The transmission may occur over one or more similar or dissimilar communications paths.

Each output block may include data portion 1006 and integrity/authenticity portion 1008. As described above, each data share may be secured using a share integrity portion including share integrity information (e.g., a SHA-256 hash) of the encrypted, pre-partitioned data. To verify the integrity of the outputs blocks at recovery time, the secure data parser may compare the share integrity blocks of each share and then invert the parse algorithm. The hash of the recovered data may then be verified against the share hash.

In some embodiments, a keyed secret sharing routine may be employed using keyed information dispersal (e.g., through the use of a keyed information dispersal algorithm or "IDA"). The key for the keyed IDA may also be protected by one or more external workgroup keys, one or more shared keys, or any combination of workgroup keys and shared keys. In this way, a multi-factor secret sharing scheme may be employed. To reconstruct the data, at least "M" shares plus the workgroup key(s) (and/or shared key(s)) may be required in some embodiments. The IDA (or the key for the IDA) may also be driven into the encryption process. For example, the transform may be driven into the clear text (e.g., during the pre-processing layer before encrypting) and may further protect the clear text before it is encrypted.

In some embodiments, the session key may be encrypted using a shared key (e.g., a workgroup key) before being parsed to generate one session key shares. Two or more user shares may then be formed by combining at least one encrypted data set share and at least one session key share. In forming a user share, in some embodiments, the at least one session key share may be interleaved into an encrypted data set share. In other embodiments, the at least one session key share may be inserted into an encrypted data set share at a location based at least in part on the shared workgroup key. For example, keyed information dispersal may be used to distribute each session key share into a unique encrypted data set share to form a user share. Interleaving or inserting a session key share into an encrypted data set share at a location based at least in part on the shared workgroup may provide increased security in the face of cryptographic attacks. In other embodiments, one or more session key shares may be appended to the beginning or end of an encrypted data set share to form a user share. The collection of user shares may then be stored separately on at least one data depository. The data depository or depositories may be located in the same physical location (for example, on the same magnetic or tape storage device) or geographically separated (for example, on physically separated servers in different geographic locations). To reconstruct the original data set, an authorized set of user shares and the shared workgroup key may be required.

The secure data parser may be used to implement a cloud computing data security solution. Cloud computing is network-based computing, storage, or both where computing and storage resources may be provided to computer systems and other devices over a network. Cloud computing resources are generally accessed over the Internet, but cloud computing may be performed over any suitable public or private network. Cloud computing may provide a level of abstraction between computing resources and their underlying hardware components (e.g., servers, storage devices, networks), enabling remote access to a pool of computing resources. These cloud computing resources may be collectively referred to as the "cloud." Cloud computing may be used to provide dynamically scalable and often virtualized resources as a service over the Internet or any other suitable network or combination of networks.

Figure 11:
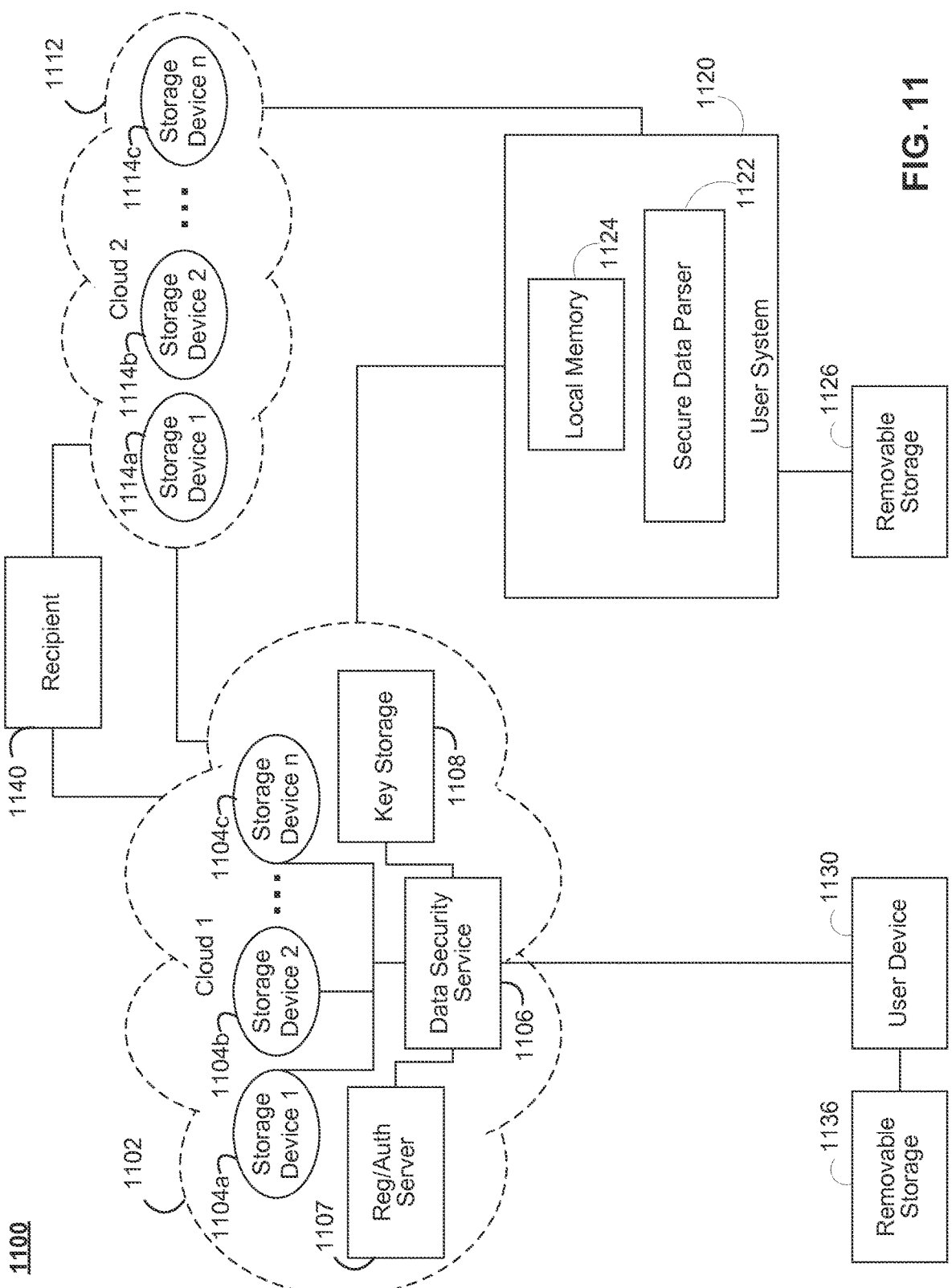
FIG. 11 is a block diagram showing several exemplary arrangements for implementing a cloud computing data security solution in accordance with an implementation.

A network 1100 showing several arrangements for using a secure data parser for implementing a cloud computing data security solution is shown in FIG. 11. The network 1100 includes two clouds, 1102 and 1112, for data and key processing and/or storage, a user system 1120 that has a local secure data parser 1122, a user device 1130 that does not have a local secure data parser, and a data recipient 1140.

User systems 1120 and 1130 are coupled to cloud 1102 which includes a number of cloud resources for storing data shares, among other functions. User systems 1120 and 1130 may include any suitable hardware, such as a computer terminal, personal computer, handheld device (e.g., PDA, Blackberry, smart phone, tablet device), cellular telephone, computer network, any other suitable hardware, or any combination thereof. User system 1120 may be configured to run a secure data parser 1122 which may be similar to the various embodiments of secure data parsers described above. The secure data parser 1122 may be integrated at any suitable level of the user system 1120. For example, secure data parser 1122 may be integrated into the hardware and/or software of user system 1120 at a sufficiently back-end level such that the presence of secure data parser 1122 may be substantially transparent to an end user of user system 1120. A recipient 1140 may be similarly coupled to cloud 1102 to access data stored by another user.

In some embodiments a user system, such as user device 1130, may not be configured to run a secure data parser, such as data parser 1122, but instead may access an external data parser that may reside on a network, for example, in data security service 1106 in cloud 1102. Cloud 1102 may include multiple illustrative cloud resources, such as data security service 1106, registration/authentication server 1107, and key storage 1108. The data security service 1106 may be used to perform operations on received data such as parsing, encrypting, and storing data, and may interface with other cloud resources. Registration/authentication server 1107 may be used to register and authenticate users of a secure storage system. Various functions of the reg/auth server 1107 are described in further detail below. Key storage 1108 may comprise one or more servers or other storage devices used to store keys such as shared keys or workgroup keys external to user system and in a different physical location from where the data is stored. A user device or user system may access these keys by communicating directly with the key storage 1108 or through the data security service 1106. Cloud 1102 also has n networked storage devices 1104a through 1104n. The cloud resources may be provided by a plurality of cloud resource providers, e.g., Amazon, Google, or Dropbox. These cloud computing resources are merely illustrative, and any suitable number and type of cloud computing resources may be accessible from user systems 1120 and 1130.

Registration/authentication server 1107 may include one or more processors configured to register users of a secure storage system such as user of secure data parser 1122, users of data security service 1106, and recipient users 1140 (which may also be users of data security service 1106). The users may include individual users, user devices, and groups of users or devices. The reg/auth server 1107 may be further configured to store user credentials such as e-mail addresses or usernames, authenticate users (e.g., based on the stored credentials), look up users by their e-mail address or other credentials, transmit a public key to a cryptographic sharing client, de-authorize one or more users from accessing the registration/authentication server 1107. The registration/authentication server 1107 may also direct users or user devices to one or more of the storage locations 1104 for writing data or for retrieving data. In particular, if data that a user device requests to retrieve has been parsed in accordance with an M of N technique (one in which M shares of N shares are needed to reassemble or restore a data set to its original or useable form, with M less than N), the registration/authentication server 1107 may identify and return to the user device information about M recommended storage locations from among the storage locations 1104a-1104n. The user device may then use this information to selectively access storage locations to retrieve the desired data.

Cloud 1102 and one or more user devices or systems, such as user system 1120, may be in communication with a second cloud 1112. Cloud 1112 includes a plurality of storage devices 1114a-1114n and may include any other cloud resources, such as the cloud resources described in relation to cloud 1102. In some embodiments, Cloud 1102 may be a public cloud (such as Amazon, Google, or Dropbox), and cloud 1112 may be a private cloud, or vice versa. In other embodiments, cloud 1102 and cloud 1112 may be different public clouds (e.g., Cloud 1102 may be provided by Amazon and Cloud 1112 may be provided by Google). Storing data shares and/or key shares across different clouds may provide enhanced data security. In addition to storing data in the cloud, one or more data shares, key shares, or keys may be stored on local storage, such as local memory 1124 of user system 1120 or a local memory of user device 1130, and one or more data shares, key shares, or keys may be stored on removable storage (e.g., a USB memory), such as removable storage 1126 or removable storage 1136 which may be for example. Any suitable number of clouds may be used. For example, in some embodiments, Cloud 1102 and cloud 1112 may form a single cloud, or only one of clouds 1102 and 1112 may be used. In some embodiments, three or more clouds may be used.

The removable storage 1126 or 1136 may be, for example, a compact USB flash drive, a floppy disk, an optical disk, or a smart card. In some embodiments, removable storage 1126 or 1136 may be used to authenticate the identity of a remote user who wishes to view, encrypt, or decrypt data that is managed by data security service 1106. In some embodiments, removable storage 1126 or 1136 may be required to initiate the encryption, decryption, or parsing of data by data security service 1106. In such embodiments, the removable storage 1126 or 1136 may be considered a physical token. An authorized recipient 1140 may also access removable storage configured to authenticate the recipient user so that the recipient 1140 may retrieve and decrypt data which it is authorized to access.

One advantage of cloud computing is that a user (e.g., a user of user device 1130 or user system 1120) may be able to access multiple cloud computing resources without having to invest in dedicated storage hardware. The user may have the ability to dynamically control the number and type of cloud computing resources accessible to it. For example, user device 1130 or user system 1120 may be provided with on-demand storage resources in the cloud having capacities that are dynamically adjustable based on current needs. In some embodiments, one or more software applications, such as secure data parser 1122 executed on user system 1120 or an Internet web browser on user device 1130, may couple a user to cloud resources 1102. The coupling of cloud resources 1102 to user device 1130 or user system 1120 may be transparent to users such that cloud resources 1102 appear to users as local hardware resources and/or dedicated hardware resources.

Figure 12:
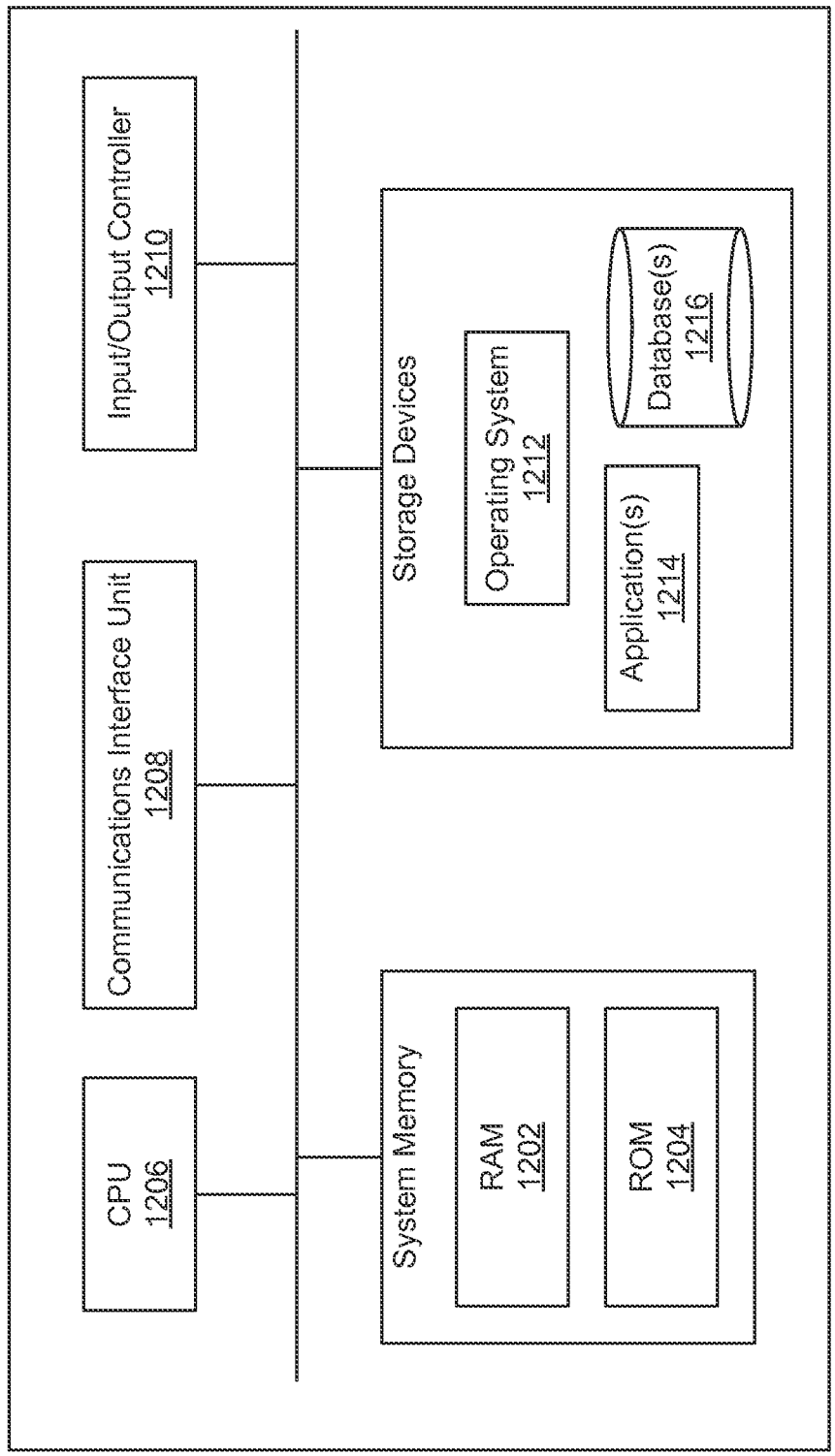
FIG. 12 is a block diagram of a computing device for performing any of the processes described herein.

FIG. 12 is a block diagram of a computing device for performing any of the processes described herein. Each of the components of these systems may be implemented on one or more computing devices 1200. In certain aspects, a plurality of the components of these systems may be included within one computing device 1200. In certain implementations, a component and a storage device may be implemented across several computing devices 1200.

The computing device 1200 comprises at least one communications interface unit, an input/output controller 1210, system memory, and one or more data storage devices. The system memory includes at least one random access memory (RAM 1202) and at least one read-only memory (ROM 1204). All of these elements are in communication with a central processing unit (CPU 1206) to facilitate the operation of the computing device 1200. The computing device 1200 may be configured in many different ways. For example, the computing device 1200 may be a conventional standalone computer or alternatively, the functions of computing device 1200 may be distributed across multiple computer systems and architectures. In FIG. 12, the computing device 1200 is linked, via network or local network, to other servers or systems.

The computing device 1200 may be configured in a distributed architecture, wherein databases and processors are housed in separate units or locations. Some units perform primary processing functions and contain at a minimum a general controller or a processor and a system memory. In distributed architecture implementations, each of these units may be attached via the communications interface unit 1208 to a communications hub or port (not shown) that serves as a primary communication link with other servers, client or user computers and other related devices. The communications hub or port may have minimal processing capability itself, serving primarily as a communications router. A variety of communications protocols may be part of the system, including, but not limited to: Ethernet, SAP, SAS™, ATP, BLUETOOTH™, GSM and TCP/IP.

The CPU 1206 comprises a processor, such as one or more conventional microprocessors and one or more supplementary co-processors such as math co-processors for offloading workload from the CPU 1206. The CPU 1206 is in communication with the communications interface unit 1208 and the input/output controller 1210, through which the CPU 1206 communicates with other devices such as other servers, user terminals, or devices. The communications interface unit 1208 and the input/output controller 1210 may include multiple communication channels for simultaneous communication with, for example, other processors, servers or client terminals. The processors may include any combination of hardware and software processors. Hardware processors include processing circuitry, which may include any combination of digital circuits, integrated circuits, ASICs, microchips, and the like. The processors are in communication with one or more non-transient computer-readable memory units, which may be local or remote to the processors.

The CPU 1206 is also in communication with the data storage device. The data storage device may comprise an appropriate combination of magnetic, optical or semiconductor memory, and may include, for example, RAM 1202, ROM 1204, flash drive, an optical disc such as a compact disc or a hard disk or drive. The CPU 1206 and the data storage device each may be, for example, located entirely within a single computer or other computing device; or coupled to each other by a communication medium, such as a USB port, serial port cable, a coaxial cable, an Ethernet cable, a telephone line, a radio frequency transceiver or other similar wireless or wired medium or combination of the foregoing. For example, the CPU 1206 may be coupled to the data storage device via the communications interface unit 1208. The CPU 1206 may be configured to perform one or more particular processing functions.

The data storage device may store, for example, (i) an operating system 1212 for the computing device 1200; (ii) one or more applications 1214 (e.g., computer program code or a computer program product) adapted to direct the CPU 1206 in accordance with the systems and methods described here, and particularly in accordance with the processes described in detail with regard to the CPU 1206; or (iii) database(s) 1216 adapted to store information that may be utilized to store information required by the program.

The operating system 1212 and applications 1214 may be stored, for example, in a compressed, an uncompiled and an encrypted format, and may include computer program code. The instructions of the program may be read into a main memory of the processor from a computer-readable medium other than the data storage device, such as from the ROM 1204 or from the RAM 1202. While execution of sequences of instructions in the program causes the CPU 1206 to perform the process steps described herein, hard-wired circuitry may be used in place of, or in combination with, software instructions for implementation of the processes of the present disclosure. Thus, the systems and methods described are not limited to any specific combination of hardware and software.

Suitable computer program code may be provided for performing one or more functions in relation to vehicle routing and motion planning as described herein. The program also may include program elements such as an operating system 1212, a database management system and "device drivers" that allow the processor to interface with computer peripheral devices (e.g., a video display, a keyboard, a computer mouse, etc.) via the input/output controller 1210.

The term "computer-readable medium" as used herein refers to any non-transitory medium that provides or participates in providing instructions to the processor of the computing device 1200 (or any other processor of a device described herein) for execution. Such a medium may take many forms, including but not limited to, non-volatile media and volatile media. Non-volatile media include, for example, optical, magnetic, or opto-magnetic disks, or integrated circuit memory, such as flash memory. Volatile media include dynamic random access memory (DRAM), which typically constitutes the main memory. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM or EEPROM (electronically erasable programmable read-only memory), a FLASH-EEPROM, any other memory chip or cartridge, or any other non-transitory medium from which a computer may read.

Various forms of computer readable media may be involved in carrying one or more sequences of one or more instructions to the CPU 1206 (or any other processor of a device described herein) for execution. For example, the instructions may initially be borne on a magnetic disk of a remote computer (not shown). The remote computer may load the instructions into its dynamic memory and send the instructions over an Ethernet connection, cable line, or even telephone line using a modem. A communications device local to a computing device 1200 (e.g., a server) may receive the data on the respective communications line and place the data on a system bus for the processor. The system bus carries the data to main memory, from which the processor retrieves and executes the instructions. The instructions received by main memory may optionally be stored in memory either before or after execution by the processor. In addition, instructions may be received via a communication port as electrical, electromagnetic or optical signals, which are exemplary forms of wireless communications or data streams that carry various types of information.

The secure data parsing techniques described herein may be applied to data access using virtual machines, and in particular, to communication between a virtual machine and one or more servers or end users. Systems and methods for providing additional security features within virtual machine computing environments that integrate virtual machine and host machine security operations are described in detail in U.S. patent application Ser. No. 13/212,360, filed Aug. 18, 2011, which is hereby incorporated herein by reference in its entirety.

The secure data parsing techniques described herein may also be implemented using a cryptographic file system layer that intercepts data to be stored on a file system and modifies at least some of the intercepted data, e.g., by securing data being stored in the file system, or by restoring secured data retrieved from the file system. According to one aspect, the cryptographic file system layer intercepts data passing between the application layer and the file system and modifies only data that is located in one or more designated directories. If a file is in a designated directory, it is modified before being stored, which provides increased security for that file; if the file is not in a designated directory, it is not modified. Retrieved files in a designated directory are also modified in order to reverse the modification that the cryptographic file system layer performed before the file was stored. Systems and methods for providing additional security features through a cryptographic file system layer are described in detail in U.S. patent application Ser. No. 14/180,151, filed Feb. 13, 2014, which is hereby incorporated herein by reference in its entirety.

Any of the above-described methods and systems may be implemented in connection with a gateway for providing cloud-based secure storage. In one aspect, the gateway provides a dynamically and/or configurably adjustable storage volume, including a dynamically and/or configurably adjustable cache. The cache and/or the storage volume may be dynamically or configurably adjusted for the amount of data that needs to be stored using available local or cloud-based storage. Certain caching techniques (e.g., local caching of frequently used data) provide gains in access latency compared to existing cloud-based gateway systems. Several advantages result from the dynamic provisioning of a cache and remote storage. For example, updates to the cloud may be performed asynchronously as a background process and are transparent to the users. Clustering of blocks stored to the cloud also reduce the latency impact of storing to the cloud. Additionally, secure features may be seamlessly integrated into the gateway at both the local cache and the cloud levels. By so doing, in one aspect, the gateway provides secure, efficient and cost-effective remote storage that may scale with the user's data needs.

Figure 13:
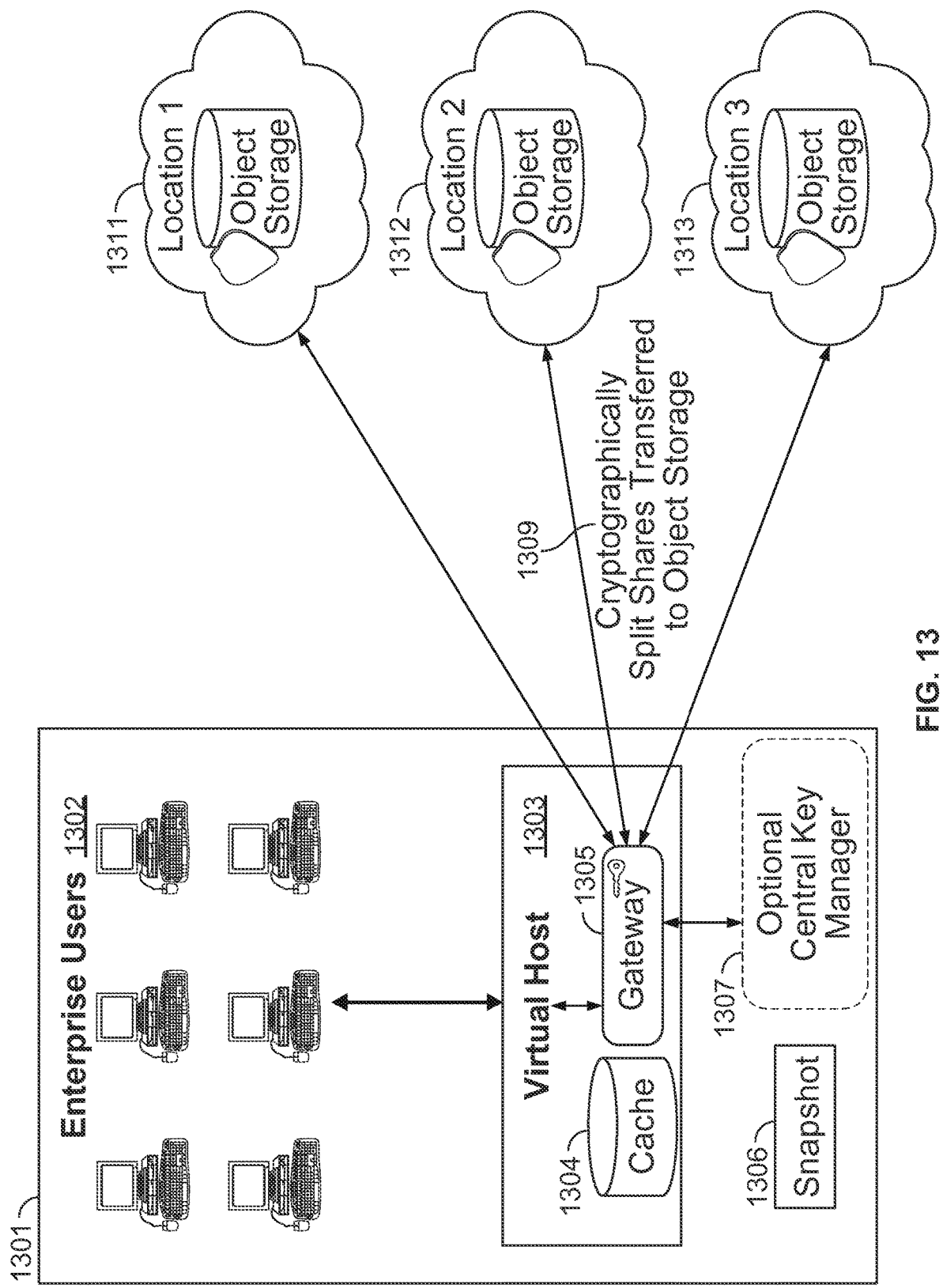
FIG. 13 provides a schematic diagram illustrating an example infrastructure of an enterprise network employing a scalable virtual storage including multiple target cloud-based storage devices, in accordance with an implementation.

FIG. 13 provides a schematic diagram illustrating an example infrastructure of an enterprise network employing a scalable virtual storage including multiple target cloud-based storage devices, in accordance with an implementation. Secure cloud-integrated enterprise data storage devices 1311-1313 may be coupled to an enterprise network 1301 as extended storage such that the enterprise storage system may adapt to rapid data growth required by the enterprise. Any one (or any portion) of the cloud-integrated enterprise data storage devices 1311-1313 may be dynamically coupled or decoupled from the enterprise network 1301 based on the demand for storage, which reduces the need to scale on-premises file storage infrastructure. The enterprise user devices 1302 may access a virtual host 1303 within an on-premises enterprise local network, which hosts a local cache 1304 and a server-side gateway 1305, as discussed below in connection with FIG. 14. The local cache 1304 may save a local copy of frequently-used data files, providing low-latency access to frequently-accessed data to the enterprise user devices 1302 (e.g., as discussed below in connection with FIG. 15B). The server-side gateway 1305 may cryptographically send data 1309 to an object cloud storage library using any of the communication channels, tunnels, and protocols discussed herein. The data sent to the cloud storage library may include previously secured (e.g., encrypted or cryptographically parsed) data. The secure data may be generated using any of the cryptographic processes discussed above in connection with the secure parser. However, in some implementations, the data is not previously secured. A snapshot module 1306 (e.g., as further discussed in connection with 1413 in FIG. 14) that is configured to generate snapshots of the storage volume, and a key manager 1307 (e.g., as further discussed in connection with logical volume manager 1411 in FIG. 14) that is configured to store encryption keys, may also be hosted on-premises within the enterprise local network. The snapshot module 1306 may provide integrated fault tolerance and data recovery to the enterprise network, including recovery of data stored in the extended storage. The key manager 1307 may be hosted in the enterprise network 1301 (as shown) or in an external network, and may be used to manage various types of keys (including session keys, splitting keys, encryption keys, authentication tokens/keys, etc.) used to manage or secure the enterprise data.

FIG. 13 shows three target cloud-based storage devices 1311-1313 located at three locations. However, any number (e.g., one, two, five, ten, up to 100, etc.) of cloud-based storage devices may be used. Moreover, the cloud-based storage devices may be located at the same location or they may be geographically separated. The gateway 1305 may incorporate the local cache 1304 and the cloud-based storage devices 1311-1313 into a virtual disk and present the virtual disk to the client computer systems. Thus, the enterprise user devices 1302 may access and operate with the virtual disk via the client computer system as if the virtual disk is "local" to the client computer system. In this way, the enterprise network 1301 may dynamically expand the storage volume by including storage space in the off-premises cloud environment in a manner that is transparent to the client and does not interfere with processes on the client.

Figure 14:
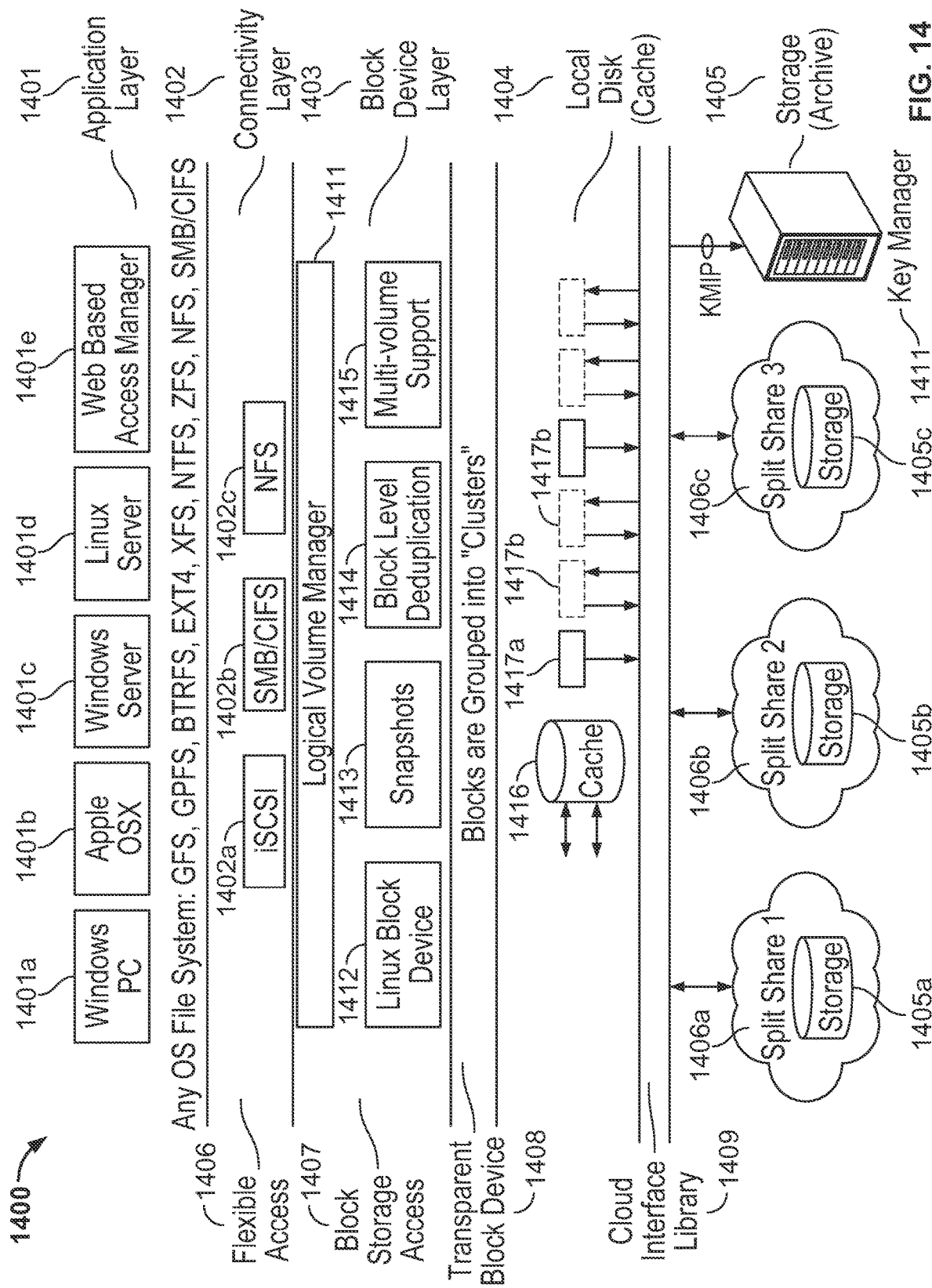
FIG. 14 is a schematic diagram showing an illustrative architecture of a server side caching gateway in accordance with an implementation.

FIG. 14 is a schematic diagram showing an illustrative architecture of a server side caching gateway according to one implementation. The server side caching gateway 1400 is housed on-premises (e.g., within an enterprise network). At the application layer 1401, the gateway 1400 receives and processes data storage requests from a variety of devices running with different operating systems (OS) and/or file systems. Example devices/protocols may include a Windows® Personal Computer (PC) 1401a operated under a Server Message Block/Common Internet File System (SMB/CIFS) or Internet Small Computer System Interface (iSCSI) initiator, an Apple® OSX 1401b operated under Network File System (NFS) or iSCSI initiator, a Windows® server 1401c operated under SMB/CFIS or iSCSI initiator, a Linux® server 1401d operated under NFS or iSCSI initiator, a web-based access manager 1401e, and/or the like. Additional OS file systems supported by the application layer 1401 include, but are not limited to, Global File System (GFS), Global Parallel File System (GPFS), B-Tree File System (BTRFS), Fourth Extended File System (EXT4), XFS, New Technology File System (NTFS), Z File System (ZFS), and/or the like. The gateway 1400 includes the features and functionalities of the mounted file system (e.g., file locking, workgroups, authentication, deduplication, clustering, past versions, redundancy, failover, performance, etc.) at the application layer 1401.

For example, the gateway caching system 1400 may use an extensible Linux storage volume mounted as an XFS file system. Through a flexible access process 1406, the gateway storage (e.g., the storage volume that includes a local cache memory 1416 and multiple remote storage devices 1405a-c) may be presented to the application layer 1401 as a standard Linux® device through the connectivity layer 1402 and the block device layer 1403. In this way, a client computer system 1401a-e may view and operate with the gateway storage as an integral storage device. For example, if the gateway cache 1416 has a size of 4 TB, and the multiple cloud-based storage devices 1405a-c provide up to 16 TB additional storage space, a file system at the client computer system 1401a-e may be presented a 20 TB gateway storage that appears to the client as local storage, even though the client computer system may have much less than of physical local storage. An application running on the client computer system 1401a-e may access, read or write data in the gateway storage via the connectivity layer 1402, which supports a variety of file system protocols.

A data file may be stored, written to or read from the local cache memory 1416 of the gateway 1400 in data units referred to herein as a data block when the gateway is interfacing with the client computer system. A data block size is typically determined in relation to the unit size of data that is written to or read by the physical local drives of the client computer. Generally, a data block has a size of 4 KB, however, other sizes (e.g., 2 KB, 8 KB, 12 KB, etc.) may be suitable in some instances. As discussed below, it is important to note that while the gateway 1400 may operate at the block level (through the block device layer 1403) when it transparently interfaces with the client computer device, the gateway 1400 may operate in cluster blocks when it interfaces with the cloud-based storage. Through block storage access 1407, the block device layer 1403 in the gateway may manage data storage requests and processes at a block level. The block device layer 1403 may include a logical volume manager 1411 that may provision and dynamically manage the required volume for data caching and archiving. For example, for the device Windows PC 1401a, the logical volume manager 1411 may provision an estimated storage volume of 14 GB based on empirical data, and for the device Linux server 1401d, the logic volume manager 1411 may provision a required storage volume of 14 TB, as the server may require more storage space.

Based on the provisioned storage volume, the gateway may link a local disk, part of the local disk, or multiple local disks 1404 into a local cache memory 1416 associated with one or more cloud-based storage devices 1405a-c that may act as a remote archive or backup storage to expand the storage space available to the enterprise devices. For example, when the local disk has a volume of 2 TB, but a client device (e.g., the Windows server 1401c or the Linux server 1401d, etc.) may demand a storage volume of 14 TB, a storage volume (e.g., a virtual disk) incorporating the local cache 1416 and one or more of the cloud-based storage devices 1405a-c may be provisioned to provide a total storage space of 14 TB. The virtual disk is presented to the client device as an integral storage disk such that a user of the client device may view and operate on the virtual disk as though the virtual disk were local. For example, an application of the client computer system does not need to send an explicit remote access request at a storage location of a remote storage device in order to read or write data from that remote storage device. The exact storage location of a data block, a cluster block or a data file in the cloud or the provisioned storage volume may be hidden from a client device. For example, a user of the client device may see a memory disk of 14 TB available on the client device, and may store, read and write to data files in the 14 TB memory disk in a similar manner as working with a local memory, without knowing an exact storage location of a specific data file. The storage volume of the virtual disk may be dynamically or configurably adjusted (e.g., by linking a different number of cloud-storage devices, or cloud-storage devices of different storage capacities). Each configured volume is set at volume configuration for either CIFS/NFS file access or iSCSI target block access. The local disk(s) 1404 may be located in a gateway server or locally within a client computer device within the enterprise network. To facilitate data coherency, data consistency, and failure recovery, the local cache memory 1416 comprises non-volatile memory that persists even if the host device is turned off.

Cloud virtualization software (e.g., VMware, etc.) may be used to grow a storage volume of the virtual disk. Example pseudo-code segment for growing a volume in VMware may be similar to the following:

```
Scan scsi bus
echo "- - -" > /sys/class/scsi_host/host[n]/scan
- Create new partition with fdisk /dev/sd[n] (eg. /dev/sdc)
- partx -a /dev/sd[n] (eg. /dev/sdc)
- pvcreate /dev/sd[n][x] (eg. /dev/sdc2)
- vgextend [volgroup] /dev/sd[n][x] (eg. vgextend vg_cache /dev/sdc2)
- pvscan
- lvextend /dev/[volgroup]/[lvol] /dev/sd[n][x] (eg. lvextend /dev/
vg_cache/lv_cache/dev/sdc2)
- xfs_growfs /dev/[volgroup]/[lvol] (eg. xfs_growfs /dev/vg_cache/
lv_cache)
```

In the above pseudo-code segment, a small computer system interface (SCSI) bus of a client computer system may be scanned to establish a communication link between the client computer system and the virtual host (e.g., 1303 in FIG. 13). A new partition with the virtual disk may be created. The gateway may then scan for an available remote storage device in the cloud, and extend the virtual disk by linking to the new remote storage device to grow the storage volume.

The block device layer 1403 may further include a Linux block device 1412 to process data through the mount layers for gateway storage. Specifically, the Linux block device 1412 manages the process of presenting the gateway storage to one of the client devices 1401a-e across the block device layer 1403 and the connectivity layer 1402. The block level deduplication module 1414 may remove duplicated blocks. The multi-volume support module 1415 may support and dynamically adjust the storage volume of the virtual disk (e.g., by including or excluding one or more cloud-based storage devices 1405a-c, etc.).

The block device layer 1403 may further include a snapshots module 1413 to generate a capture of the data environment of the gateway caching system 1400. The capture of the data environment may include a copy of the data content, system parameters, and/or the like, which are captured at a specific timestamp. The snapshot of a local file system on the client computer system (e.g., the client devices/systems 1401a-e in the application layer 1401) may be generated periodically, intermittently or per user request, etc. In response to detecting a snapshot request of a state of the data environment of a local file system for the client computer system (e.g., 1401a-e), a snapshot (e.g., a capture) may be synchronized throughout the virtual disk with one or more cloud-based storage devices for the client computer system. For example, when a snapshot of the local cache memory 1416 is generated, the snapshots module 1413 may send a snapshot request to the cloud-based storage devices 1405a-c to each generate a snapshot of cluster blocks stored in the cloud that are related to the local file system on the client computer system. Each of the remote storage devices 1405a-c may in turn generate a snapshot of its own data environment at the specific timestamp. Thus the snapshot of the virtual disk at a specific timestamp may include both the data capture of the local cache and the data capture of related cluster blocks in the cloud-based storage devices. In this way, when a user or an application requests to restore the state of the file system at the specific timestamp, a snapshot including both the data capture of the local cache and the data capture of related cluster blocks in the cloud-based storage devices may be provided to the user or the application.

A version number may be assigned to the snapshot indicating a data version at the specific timestamp. The snapshot is then saved as a data copy associated with version number in a data recovery folder without overwriting an earlier snapshot with an older version number generated at an earlier time. In this way, a user or an application may roll back in time to retrieve data content in the virtual disk at the specific timestamp. Further discussion on generating data captures of the storage volume may be found in connection with FIG. 24.

A transparent block device 1408 may couple the block device layer 1403 and the local disk 1404 to the remote storage capabilities of the gateway. For example, the transparent block device 1408 establishes a relationship between the physical local storage at the local cache memory 1416 and the remote storage 1405a-c. The transparent block device 1408 may also intercept data requests passed on from the client computer system via the connectivity layer 1403 and block device layer 1404, so that the requested data operation (e.g., store, read or write to a data file, etc.) may be transparently performed by the transparent block device 1408. The transparent block device 1408 may also detect snapshot events that occur at the local cache memory 1416, so that a snapshot request may be sent to the remote storage devices 1405a-c.

Operations within the transparent block device 1408 are transparent to a client device. The transparent block device 1408 may group data blocks from the block device layer 1403 into cluster blocks. As discussed above, a cluster block includes a group of data blocks that are written or transmitted together to (or retrieved or received together from) the cloud simultaneously. According to one implementation, the size of a cluster block (e.g., how many data blocks are to be grouped into a single cluster block) may be dynamically adjusted, or configured periodically, intermittently, or per user request. A cluster block may include any number of data blocks (e.g., one block, five blocks, ten blocks, or several hundred data blocks, etc.), and may have any suitable size (e.g., 2 MB, 5 MB, 10 MB, 100 MB, etc.). The size of a cluster block may also be adjusted based on the type of data, an average file size for a particular client computer system, etc. The size of the cluster block may also be adjusted based on system performance feedback, e.g., whether the existing cluster block size is too large, which leads to read/write operation latency, or whether the existing cluster block size is too small such that the frequent remote read/write operations may be burdensome to the system.

The local cache 1416 maintains a cache cleaning process to keep the local cache usage under a specified size by removing the least recently used cluster blocks from the local cache. Alternatively or additionally, cluster blocks that have not been accessed for a predefined period of time (e.g., 24 hours, 1 week, 15 days, etc.) may be cleaned from the local cache 1416. The removed cluster blocks 1417b (cache misses) are sent to be stored at one of the cloud-based storage devices, and the remaining cluster blocks 1417a may be kept at the local cache 1416 as a local copy. The cache cleaning process may be performed periodically, intermittently, on-demand, or progressively when a data file is being stored. For example, when cluster blocks are written to the local cache 1416, the local cache 1416 may progressively remove the least used cluster blocks to create more space for the data write operation and to avoid cache overflow.

Cluster blocks generated at the transparent block device 1408 are written through the cloud interface library 1409 to the cloud storage 1405. For example, cache misses 1417b may trigger a read operation from the cloud interface library to populate the missing blocks, as further discussed with respect to FIG. 21B. The cloud interface library 1409 serves as an interface between the local disk 1404 and the cloud storage 1405. Lossless compression, cryptographic parse and/or cloud object read/write operations may be performed by the cloud interface library 1409. A key manager 1411 provides an interface to store a variety of keys such as the encryption keys, splitting keys, session keys, server keys and/or other keys as described herein (e.g., on a Key Management Interoperability Protocol (KMIP) compliant key manager or a proprietary key manager).

The gateway 1400 may incorporate data security at the local cache memory 1416 and/or at the cloud interface library 1409. Any of the functions discussed for the secure parser in connection with FIG. 7 may be applied to provide data security to cluster blocks in the local cache 1416 or in the cloud-based storage devices 1405a-c. In some implementations, one type of data security may be applied to data cluster blocks stored in the local cache memory 1416, and a different type of data security may be applied to cluster blocks sent to the cloud-based storage devices 1405a-c. For example, when cluster blocks are written to a local cache 1416, the local cache 1416 may apply a first cryptographic operation to the cluster blocks by, for example, encrypting the cluster blocks using a first encryption key. When one or more of the cluster blocks are sent from the local cache to a cloud-based storage device 1405a-c, the cloud interface library 1409 may apply a second cryptographic operation on the already secured cluster blocks from the local cache memory using, for example, a second encryption key different from the first encryption key. The first encryption key and the second encryption key, as managed by the key manager 1411, may be stored at the same or different storage locations from the storage location of the respective cluster block(s). At the cloud interface library 1409, each cluster block may be distributed in a number of data shares, and the data shares 1406a-c are stored by the one or more remote storage devices 1405a-c. In some implementations, a cluster block may be shuffled into a single data share. The data shares 1406a-c that are related to a single cluster block may be sent to a same storage device, or may be distributed among different cloud-based storage devices 1405a-c.

In some implementations, the cloud interface library 1409 may split each cluster block into a plurality of secondary data units, and cause each secondary data unit to be placed into one of the number of data shares. The secondary data units may be placed into shares using a key generated, for example, based on a random or pseudo-random number. The splitting may be performed in a manner such that each cluster block may be restorable by recombining a subset less than all of the secondary data units from the number of data shares 1406a-c. The split key may be stored and/or managed by the key manager 1411.

Figure 15A:
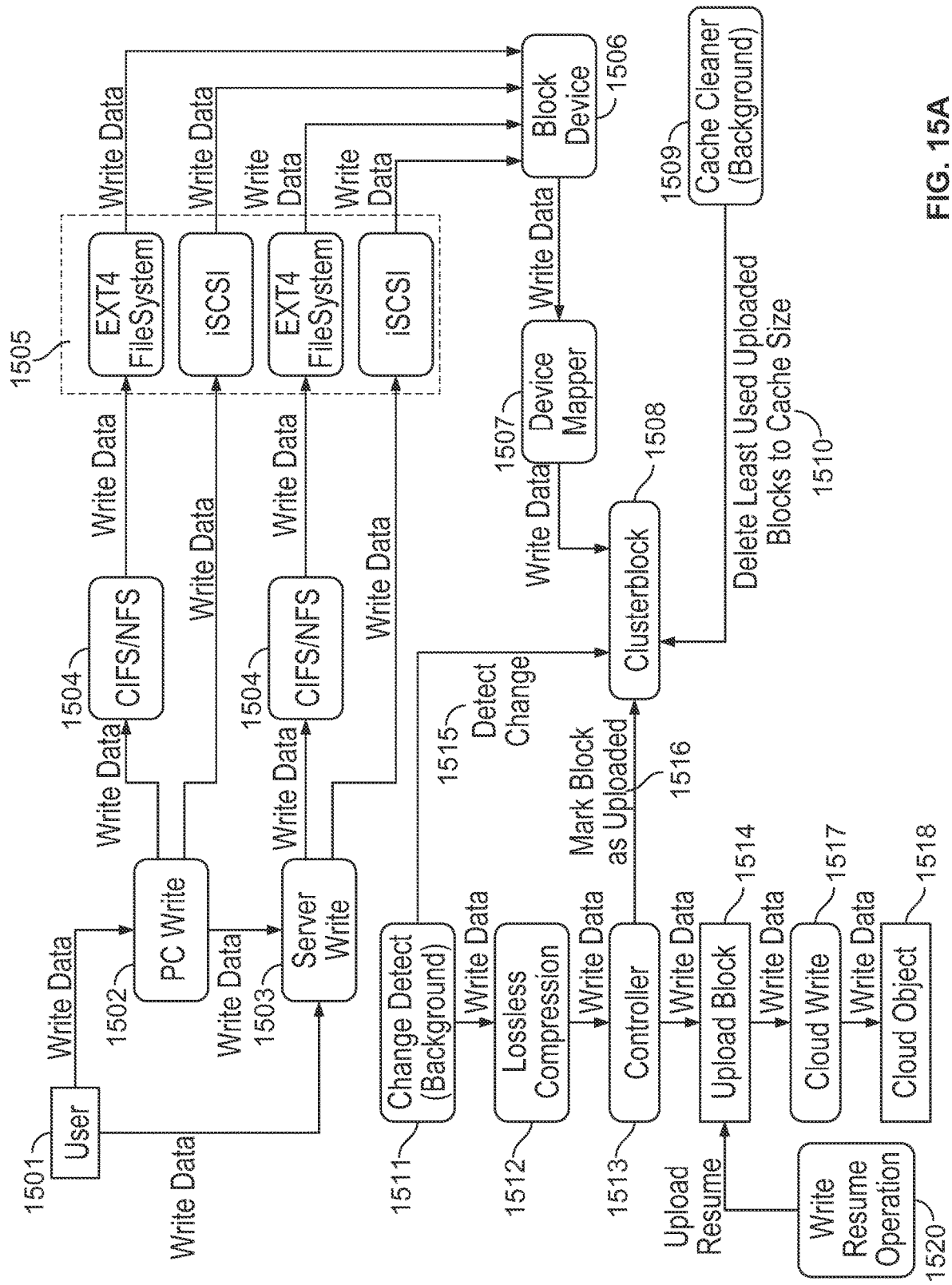
FIG. 15A provides a data flow diagrams illustrating aspects of a gateway write operation with a cloud-based virtual disk in accordance with an implementation.

FIG. 15A provides a data flow diagram illustrating aspects of a gateway write operation with a cloud-based storage volume in accordance with an implementation. In FIG. 15A, a user 1501 may request to write data (e.g., by sending a data storage/editing/updating request, etc.) to a user device such as a PC 1502, or a server 1503. The user devices are hosted at an application layer (e.g., see 2001 in FIG. 20). The user devices may then pass the write data request to the respective file system such as CIFS/NFS 1504, which turn writes data to the OS file system layer such as EXT4 file system or iSCSI 1505 (e.g., similar to the connectivity layer 2002 in FIG. 20).

The block device 1506 (e.g., similar to the block device layer 1403 in FIG. 14) may then receive the write operation request and pass the write request to a device mapper 1507 to direct the write request to the cluster block module 1508 (e.g., similar to the transparent block device 1408 in FIG. 14). The device mapper 1507 translates the block I/O into file I/O using a block map that reads and writes blocks into sequential cluster blocks. For example, the device mapper 1507 obtains a write operation request that is associated with a data file, and then may translate identifying information of the data file to identifying information (e.g., sequential identifiers, etc.) of one or more cluster blocks that represent the data file and that are stored in the storage volume. A block map may be used by the device mapper 1507, which may include mapping information between a data file and the associated cluster blocks. For instance, the block map may map one or more data files to a specific cluster block when the specific cluster block includes data blocks from the one or more data files. Or alternatively, the block map may map a data file to one or more cluster blocks when the one or more cluster blocks includes data blocks from the data file. The cluster block module 1508 may periodically, intermittently or progressively per write operation demand, perform the cache cleanup process 1509 in the background to delete the least used data blocks/clusters from the cache to maintain the cache under a specified size (e.g., at step 1510).

The gateway may implement a strict data consistency model where any read always returns the result of the most recent write. Data coherency is maintained between the gateway and the object cloud storage 1518 by ensuring that no data is removed from the gateway cache until it has been confirmed as written to the cloud storage. No data is removed from the gateway until it has been confirmed as written to disk. This may be done at two levels in the write process.

First, when a change is detected in a cluster block module 1508, at process 1511, the data block/cluster block with the change is compressed and cryptographically split at process 1512. The result of this operation is written to the upload directory as an upload block/cluster block at 1514. Upon confirmation that the upload block/cluster block has been written, the gateway controller 1513 may change the state of the data block/cluster block to an "uploaded" state at 1516. At this time the cluster block module 1508 may keep cleaning by the cache cleaner process 1509. Second, the upload blocks/cluster blocks 1514 may remain in the upload directory until they have been confirmed to have been uploaded to the target cloud object storage destination(s) 1518. Upon successful cloud write operation at 1517, the upload blocks/cluster blocks may be removed from the upload directory.

As the data blocks/cluster blocks in the cluster block module 1508 and the upload blocks/cluster blocks 1514 are consistent until the operation has been completed, resuming operation after a failure may be performed on the available blocks/cluster blocks. Specifically, resuming operation 1520 on changed data blocks/cluster blocks may overwrite any partially created upload blocks with the cluster block module 1508 information and then mark the data block/cluster block as uploaded. Alternatively or additionally, the resuming operation 1520 may be performed on partially uploaded upload blocks/cluster blocks 1514 to overwrite any partially written cloud object targets and remove the upload block/cluster block 1514.

Figure 15B:
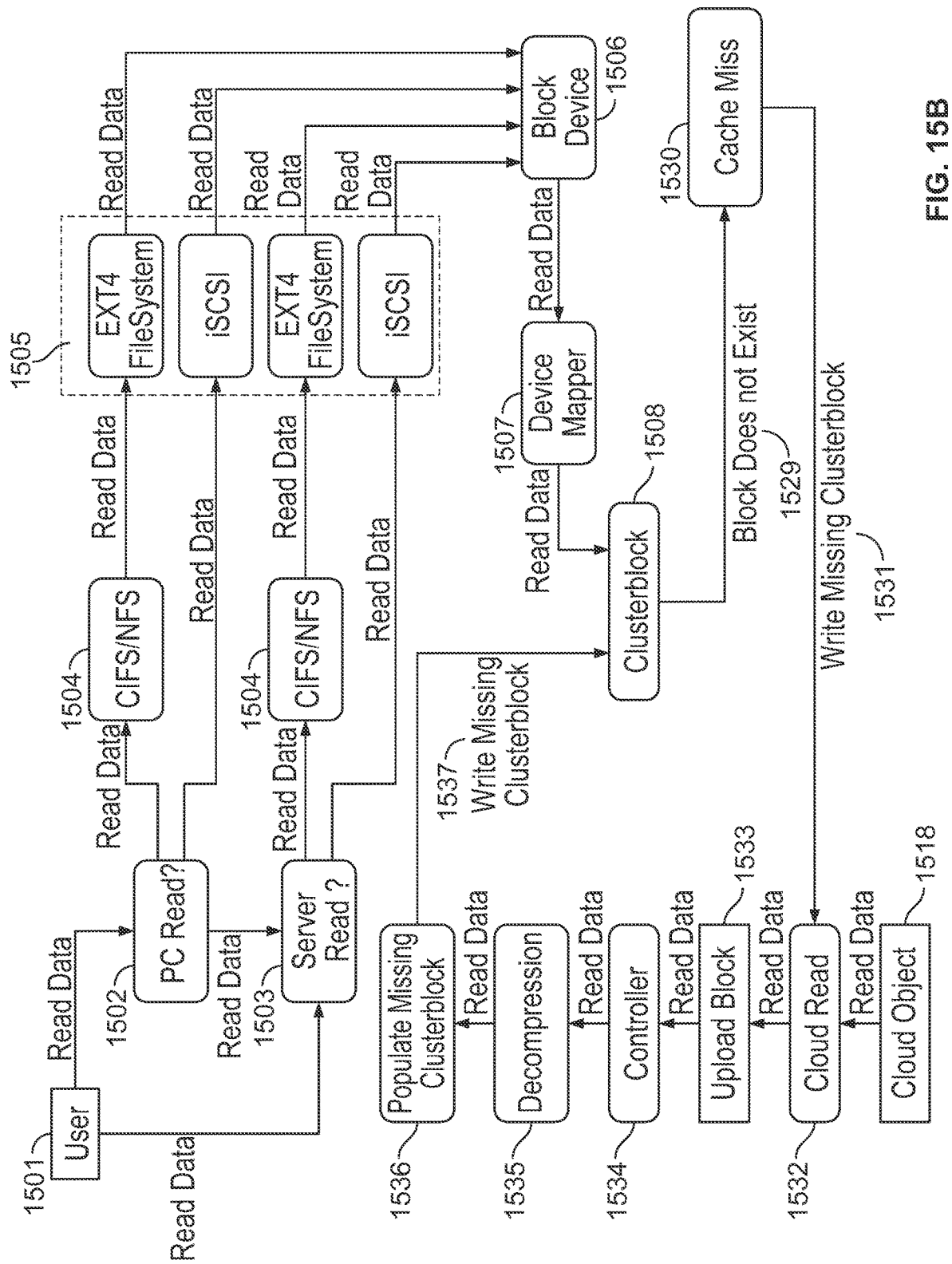
FIG. 15B provides a data flow diagrams illustrating aspects of a gateway read operation with a cloud-based virtual disk in accordance with an implementation.

FIG. 15B provides a data flow diagram illustrating aspects of a gateway read operation with a cloud-based storage volume in accordance with an implementation. For a read operation, in a similar manner, as shown in FIG. 15B, the user 1501 may send a read request to a PC 1502 or a server 1503, which may in turn pass the read request to the file system CIFS/NFC 1504, and the file system 1505 at the connectivity layer. The block device 1506 may obtain the read request, and then forward the read request to the device mapper 1507 and the cluster block module 1508. As the gateway may have stored a cached copy of a data block/cluster block at the local cache memory for fast data retrieval, the gateway may determine whether a local copy of data block/cluster block associated with the read request is available in the local cache. If the local copy is available, the gateway may retrieve the data block/cluster block from the local cache and present it to the user 1501. Otherwise, when the block/cluster block does not exist in the local cache at step 1529, a cache miss 1530 is identified. For each "cache miss," a read request may be send to the cloud read operation 1532 for the missing data block/cluster block at 1531. The cloud read operation 1532 may read the data block/cluster block from the respective cloud object storage 1518, return the read data block/cluster block to an upload block directory 1533. The gateway controller 1534 may then perform decompression of the retrieved data block/cluster block at the decompression process 1535. As the retrieved data block/cluster block at the decompression process 1535 may be in the form of data shares, the data shares may be reassembled and decrypted, and then be populated to the cluster block module 1508. For example, the gateway may optionally write the retrieved data block/cluster block 1537 into the local cache via the cluster block module 1508. Here, as the retrieved data block/cluster block is just accessed, it may be saved in the local cache as a recently used data block/cluster block, while the cluster block module 1508 may clean other less used data blocks/cluster blocks in the local cache.

Figure 16:
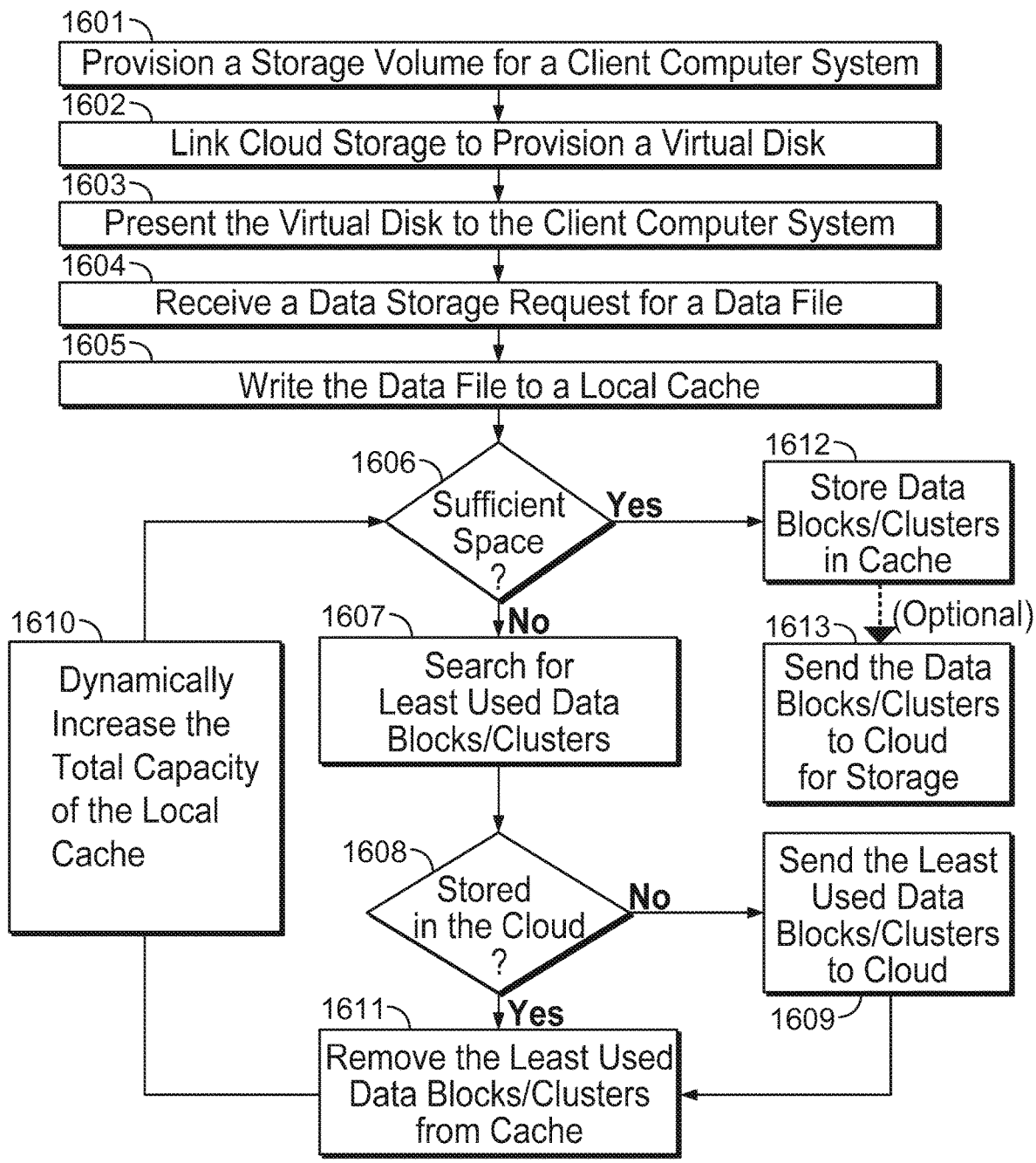
FIG. 16 provides a data flow diagram illustrating aspects of a cache cleaning process in response to a data storage request, in accordance with an implementation.

FIG. 16 provides a data flow diagram illustrating aspects of a cache cleaning process in accordance with an implementation. The cache cleaning process at a local cache may be performed in the background periodically, intermittently, or triggered by an event in order to increase available storage space at the local cache and/or to avoid storage overflow at the local cache. For example, the cache cleaning event may be triggered when a data file, or a data block/cluster block is being written to the local cache, but the local cache does not have enough free space for the data being written. Or alternatively, the cache cleaning event may be triggered when the available space at the local cache is smaller than a pre-determined threshold, e.g., the cache size may be desired to be maintained under a specified size.

At step 1601, the gateway may provision a storage volume (e.g., by the logical volume manager 1411 in FIG. 14) for a client computer system (e.g., any of the client devices 1401*a-e* in FIG. 14), or an application running on the client computer system. At step 1602, the gateway may then link one or more cloud-based storage devices with a local cache memory to provision a virtual disk (e.g., through the transparent block device 1408 and the cloud interface library 1409 in FIG. 14). For example, when the provisioned storage volume is greater than the available storage space of the local cache, incorporating cloud-based storage devices may grow the storage volume associated with the gateway. At step 1603, the gateway may then present the virtual disk to the client computer system, such that the client computer system or an application running on the client computer system (e.g., see the application layer 1402 and client devices 1401*a-e* in FIG. 14) may use the virtual disk as if the virtual disk is "local" to the client computer system. For example, an exact storage location of a data file in the remote storage devices in the cloud(s) may be hidden to a user and/or an application running on the client computer system.

At step 1604, a data storage request to store a data file is received at the gateway, e.g., the data request may be generated by an application running on the client computer system (e.g., see the application layer 1402 and client devices 1401*a-e* in FIG. 14). The data storage request at step 1604 may be received before, after, or in parallel to the storage volume provision at steps 1601-1603. At step 1605, the gateway may start writing the data file into the local cache at step 1605 (e.g., through the transparent block device 1408 in FIG. 14). For example, the gateway may write the data file to the cache in data blocks having a size of 2 KB, 4 KB, 8 KB and/or the like, or alternatively in cluster blocks of a larger size (e.g., 2 MB, 4 MB, 8 MB, 10 MB). Each cluster block may include a sequential group of data blocks that may represent a part of, an entirety of, or multiple separate data files, e.g., as discussed in connection with the transparent block device 1408 in FIG. 14.

At step 1606, while the data file is being written to the local cache in data blocks or cluster blocks, the gateway may determine whether there is sufficient storage space at the local cache (e.g., see the local cache memory 1416 in FIG. 14). For example, the local cache may or may not have enough free space for the data file, or a cluster block of the data file that is being written to the local cache. In that case, at step 1607, the local cache may initiate a cache cleanup process by searching for the least frequently or recently used cluster blocks in the local cache (e.g., see the local cache memory 1416 in FIG. 14). At step 1608, the gateway may then determine whether the least frequently or recently used cluster block has been stored in the cloud, e.g., the local cache may not clean up a cluster block if no other copy of the cluster block exists in the cloud storage. At step 1611, if the least frequently or recently used cluster block has already been stored in the cloud, the least frequently or recently used cluster block may be removed from the local cache (e.g., see the local cache memory 1416 in FIG. 14). Otherwise, at step 1609, the cluster block is sent to one or more cloud-based storage device (e.g., via the cloud interface library 1409 in FIG. 14) before being cleaned up from the local cache. The cache cleanup may be repeatedly and/or progressively performed while a cluster block is being written to the local cache until sufficient space at the local cache is found. In some implementations, when a file size is greater than a total capacity of the local cache memory (e.g., a large data file of 5 TB to be written to a local cache size of 4 TB), at step 1601, the gateway may dynamically increase the total capacity of the local cache to avoid a cache overflow. Similarly, if the allocated size of the local cache memory exceeds the needed amount of local cache storage by more than a threshold amount, the gateway may decrease the total allocated cache size, thereby freeing up storage space for other enterprise user devices or for other processes. The dynamic cache throttling that increases or decreases the total capacity may be transparent to a client computer system. In this way, the available storage space at the local cache may be dynamically increased to avoid storage over flow, or dynamically decreased to free up unused space. In addition, the gateway may monitor and control the data rate that the data file (or a cluster block of the data file) is written to the local cache (e.g., see the local cache memory 1416 in FIG. 14) in relation to the speed of transfer to the cloud libraries, such that the local cache does not have a storage overflow.

At step 1612, when enough space has been obtained at the local cache, e.g., after the cache cleanup, the gateway may write the data file (or a cluster block) to the local cache (e.g., via the transparent block device 1408 in FIG. 14). At step 1613, the data file (or the cluster block) may also be sent to one or more cloud-based cloud devices for storage (e.g., via the cloud interface library 1409). Data cluster blocks that are locally stored at the local cache or sent for remote storage in the cloud may be secured via one or more cryptographic operations, as discussed in connection with FIG. 14.

Figure 17A:
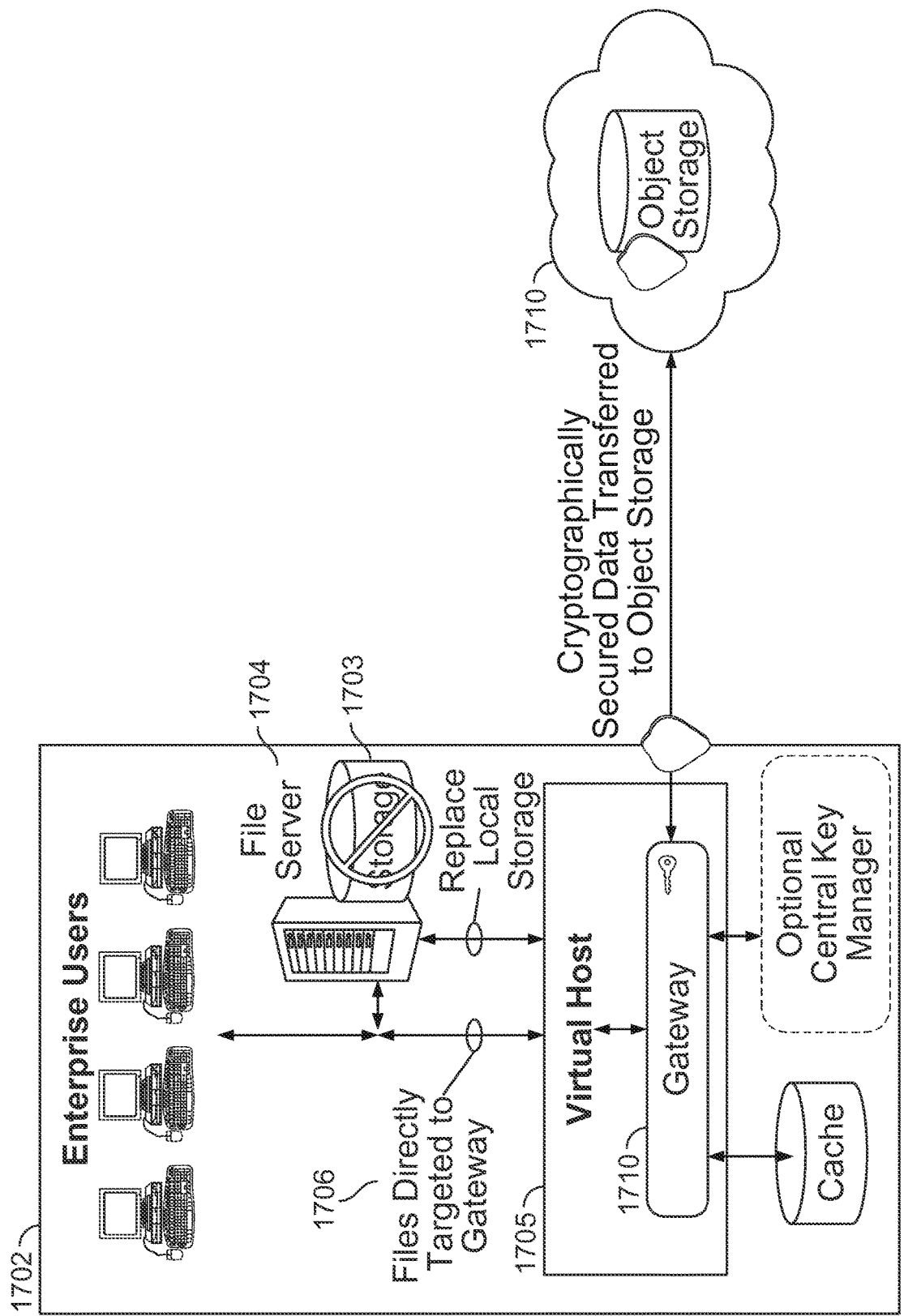
FIGS. 17A-C provide schematic diagrams illustrating example infrastructures of an enterprise network with off-premises storage set-up within a cloud-based storage environment, in accordance with an implementation.
Figure 17B:
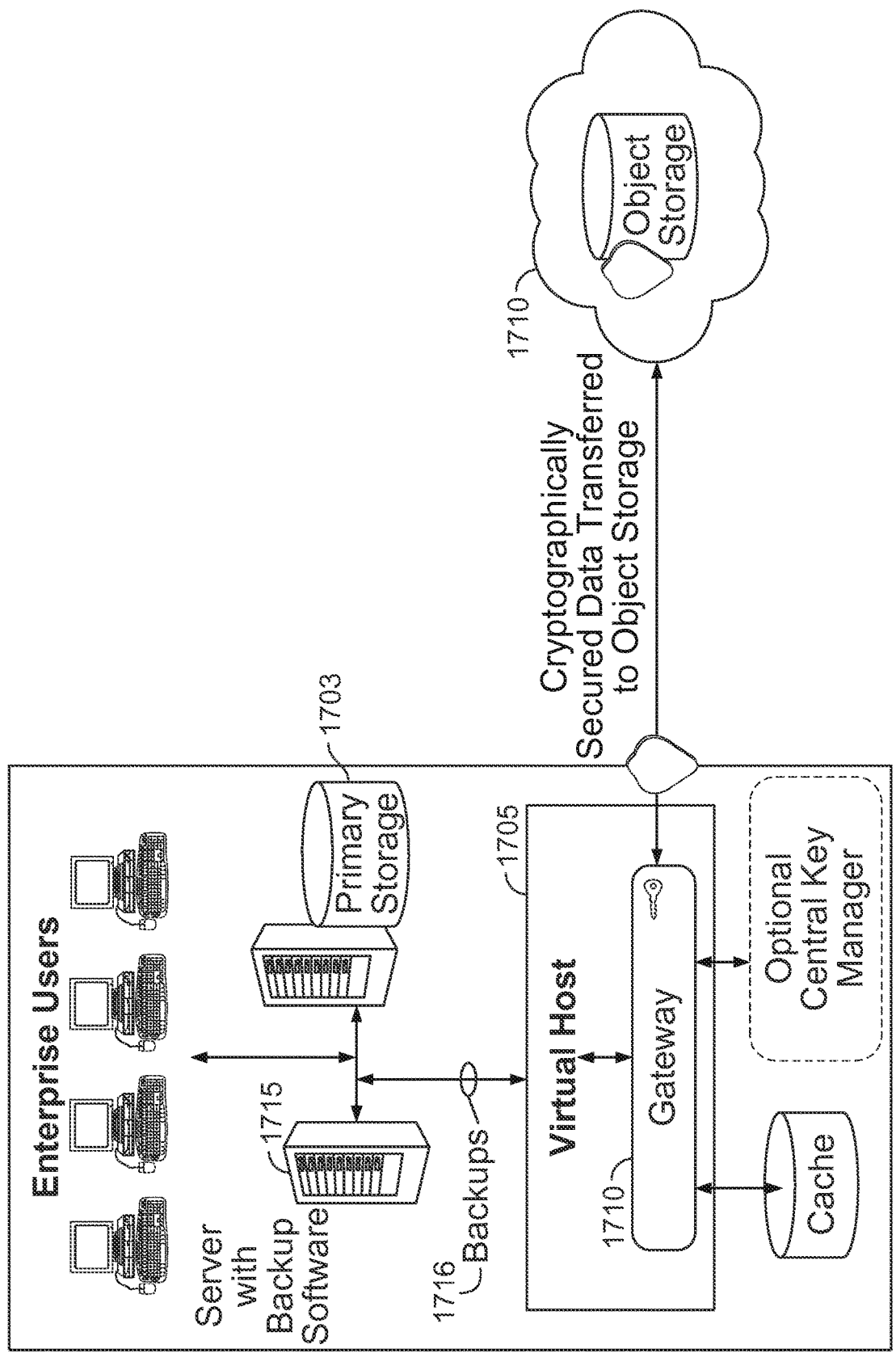
Figure 17C:
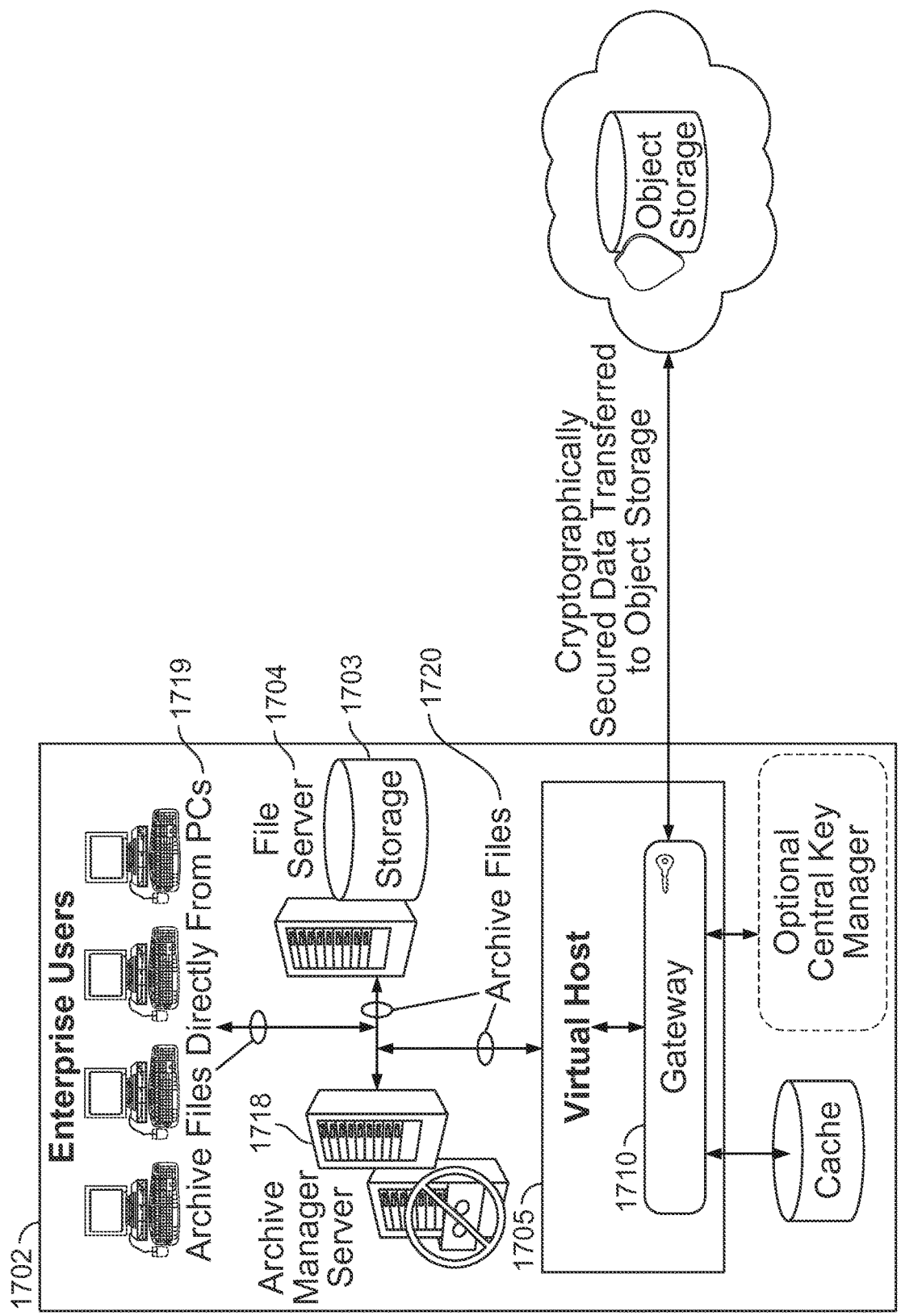

FIGS. 17A-C provide schematic diagrams illustrating example infrastructures of an enterprise network with off-premises storage set-up within a cloud-based storage environment in accordance with an implementation. In FIG. 17A, an enterprise user device 1702 may use cloud storage library 1710 as the primary storage without on-premises storage 1703 so that the enterprise does not have to build its own data center. The enterprise user device 1702 may create a cloud account for access to the object cloud-based storage 1710 (e.g., SWIFT-Open Stack) storage. For example, the enterprise user device 1702 may download and install gateway software associated with the gateway 1710 on an on-premises server (e.g., a dedicated hardware server or a virtual machine 1705). Any files from the enterprise user device 1702, or from the file server 1704 may be sent transparently to the gateway at 1706. The gateway 1710 may be configured to point to the desired cloud object storage locations. Any data sent to the on-premises gateway 1710 that replaces the local storage 1703, may be automatically cryptographically split and sent as multiple shares to multiple cloud storage locations 1710. Stored data may be metered, and billing to the enterprise user device 1702 may be added to monthly cloud invoice based on the amount of data stored.

In FIG. 17B, the enterprise user devices may maintain backup data in a separate location from the primary data in the cloud storage 1710 or on-premises primary data storage 1703. For example, the enterprise client devices may have existing storage with existing backup programs running. When the backup storage needs to grow, scaling the primary storage 1703 and having backup storage 1715 in the same location as primary storage 1703 may be challenging. In that case, the enterprise user devices may configure the virtual host 1705 with gateway software in a similar manner as discussed in FIG. 17A, and then point existing backup software at 1715 to the gateway 1710 for storage of backup data 1716. Any data backup 1716 from their on-premises server 1715 may then go to gateway backup. The data sent to the backup storage may be automatically cryptographically split and stored in multiple shares at multiple cloud storage locations 1710.

In FIG. 17C, a data archive server 1718 may be employed to avoid the capital cost and scaling overhead when the need of data storage grows. Archive files may be directly sent from the enterprise client computers 1719 (e.g., PCs) to the archive manager server 1718, which stores the archive files 1720 at the on-premises storage 1703. When the needs for archives increases, archive files 1720 may be sent to the virtual host 1705, for archiving the data files in the cloud via the gateway 1710.

Figure 18:
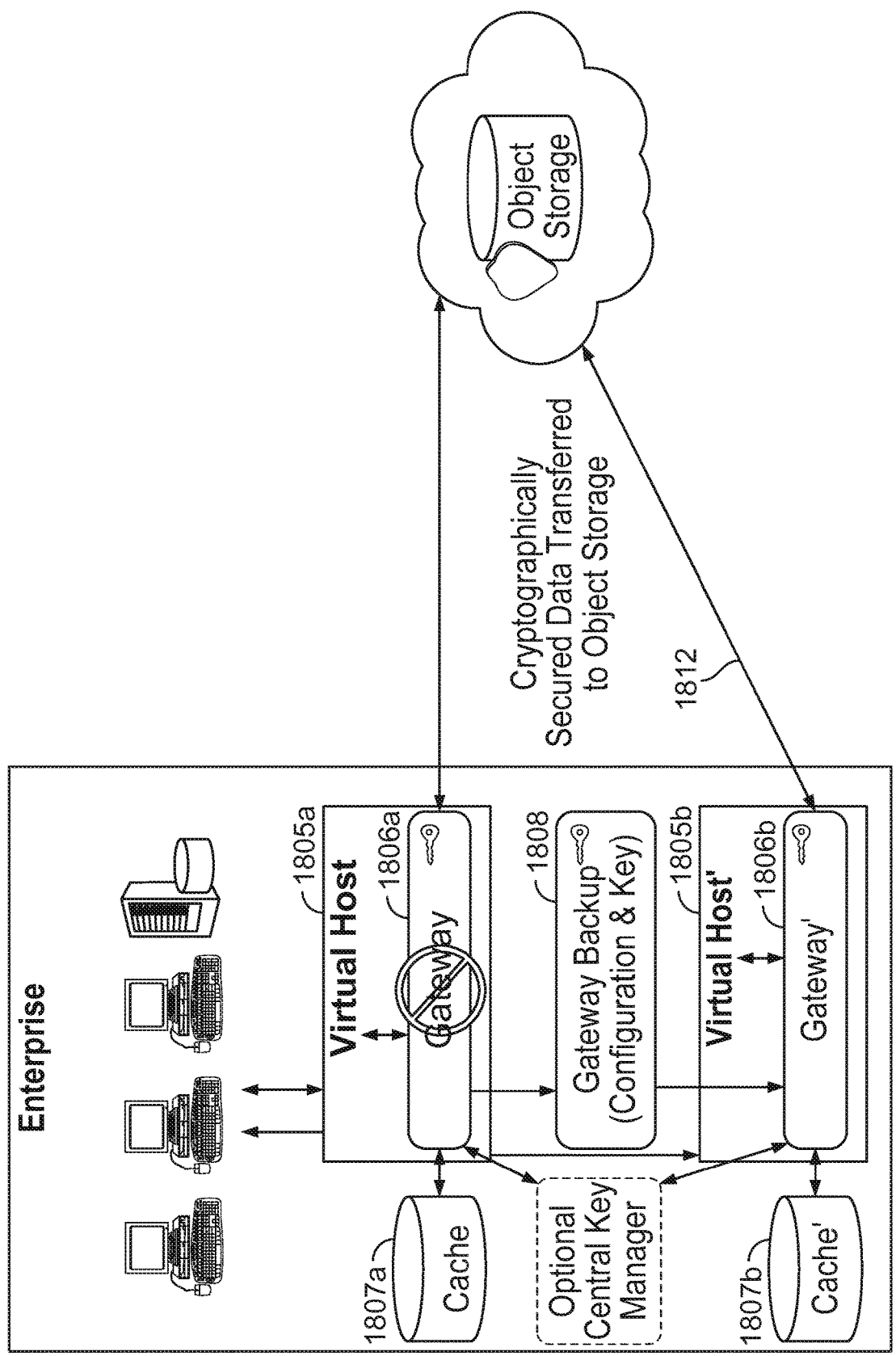
FIG. 18 provides a schematic diagram illustrating an example infrastructure of an enterprise network to handle gateway server failure, in accordance with an implementation.

FIG. 18 provides a schematic diagram illustrating an example infrastructure of an enterprise network to handle gateway server failure in accordance with an implementation. At the enterprise premise, a backup virtual host 1805*b* having a backup gateway 1806*b* and a backup cache memory 1807*b* a secure gateway backup module 1807*b* may co-exist with the primary virtual host 1805*a*. When the primary gateway 1806*b* fails, a secure gateway backup module 1808 may initiate the backup virtual host 1805*b* such that the backup gateway 1806*b* may replace the failed primary gateway 1806*a*, and the backup cache 1807*b* may replace the primary cache 1807*a*. The backup gateway 1806*b* may then send cryptographically split data shares to the cloud storage via communication link 1812.

Figure 19A:
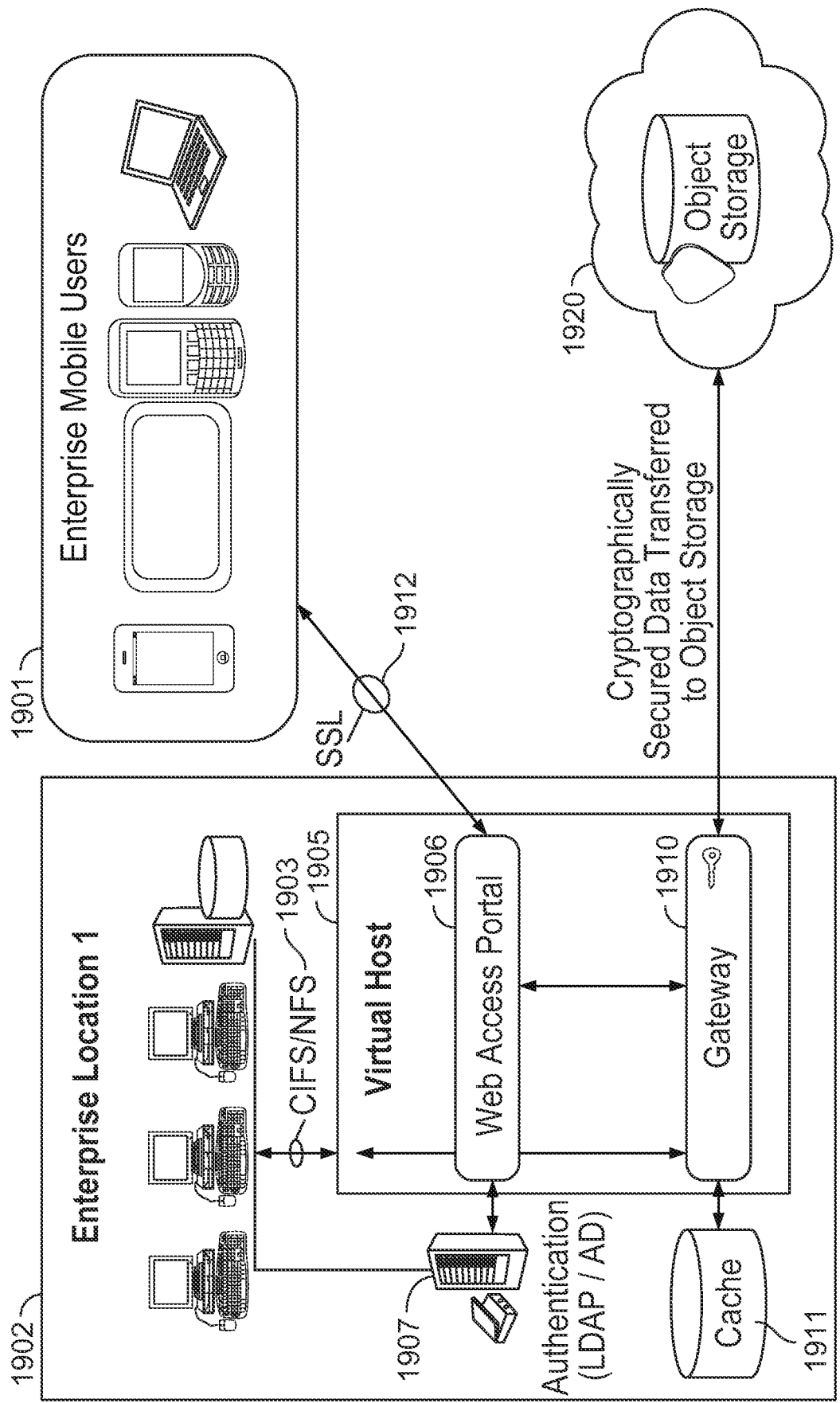
Figure 19C:
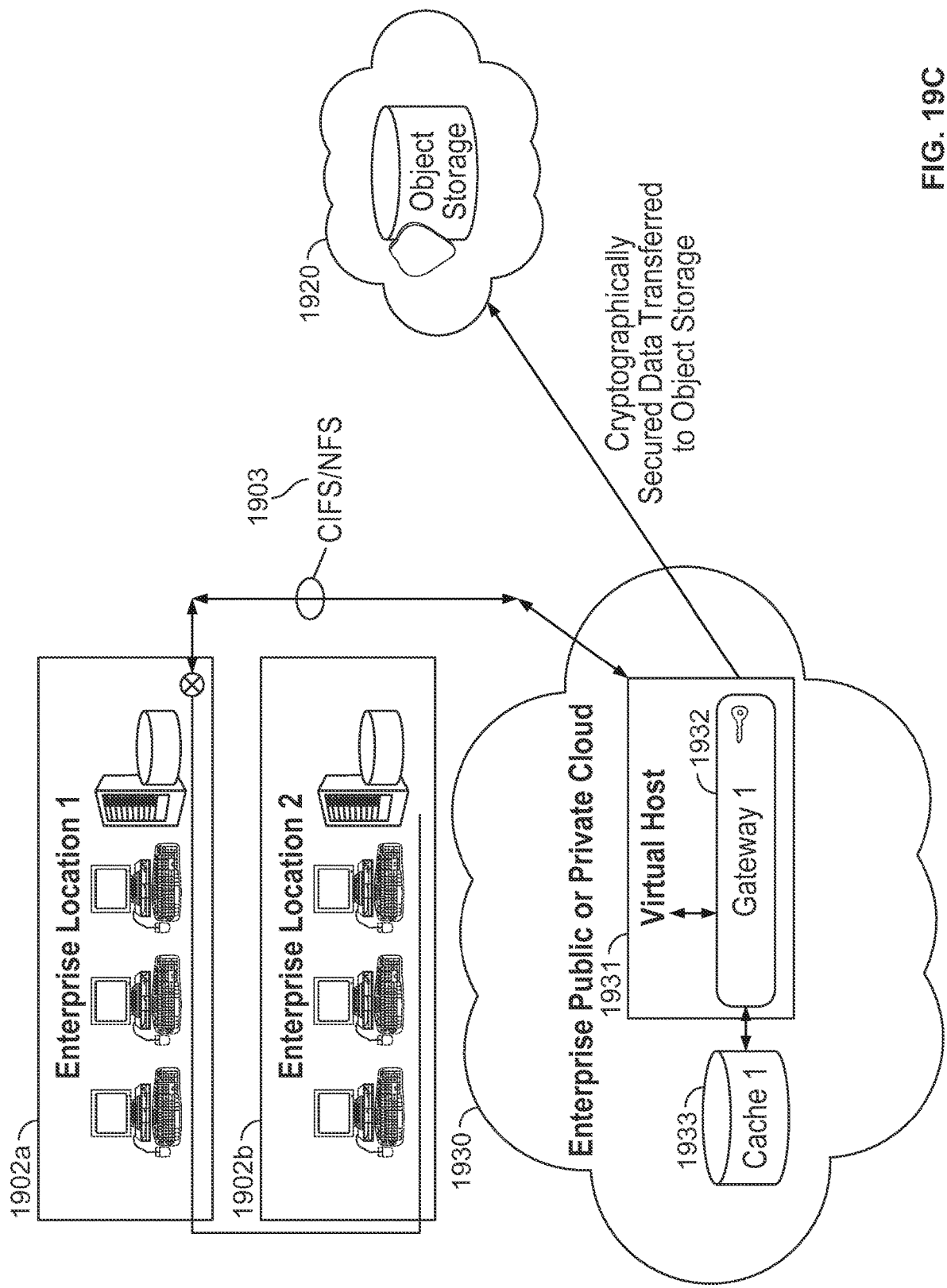

FIGS. 19A-C provide schematic diagrams illustrating example infrastructures of multiple client devices and/or multiple enterprise locations within a collaborated cloud-based storage environment in accordance with an implementation. In FIG. 19A, the enterprise local network at a first enterprise premises 1902 may host a virtual host 1905 that receive data files via CIFS/NFS file system protocols 1903 from enterprise client computers. The virtual host 1905 may also host a web access portal 1906 that allow web-based or mobile access to the gateway 1910 for the virtual disk. For example, various enterprise mobile users 1901 via a secure sockets layer 1912 (SSL) link to access the gateway 1910. For example, the portal users may be authenticated by the authentication database 1907. The mobile users 1901 may then be presented a virtual disk incorporating the local cache 1911 and the cloud storage 1920, in a similar manner as the user devices/systems 1401*a-e* as discussed in relation to FIG. 14.

In FIG. 19B, the enterprise on-premises networks may be geographically distributed at different locations 1902*a-b*. Each enterprise location may send data files via CIFS/NFS file system protocol 1903*a-b* to the virtual host 1905*a-b*. Each gateway 1906*a-b* at each location may operate a virtual disk incorporating the local cache 1911*a* or 1911*b* and cloud storage 1920. In some implementations, the enterprise network may allow cross-site sharing (e.g., virtual host 1906*a* may receive and store data from enterprise location 1902*b*, and vice versa).

In FIG. 19C, an enterprise public or private cloud 1930 may be employed for cross-site sharing between multiple enterprise locations 1902*a-b*. The enterprise public or private cloud 1930 may host the virtual host 1931 including the gateway 1932, and a local cache 1933. In this way, the enterprise public or private cloud 1930 may receive data via CIFS/NFS 1903 from different enterprise locations 1902*a-b*, and then cryptographically transfer data to remote cloud storage 1920.

Figure 20A:
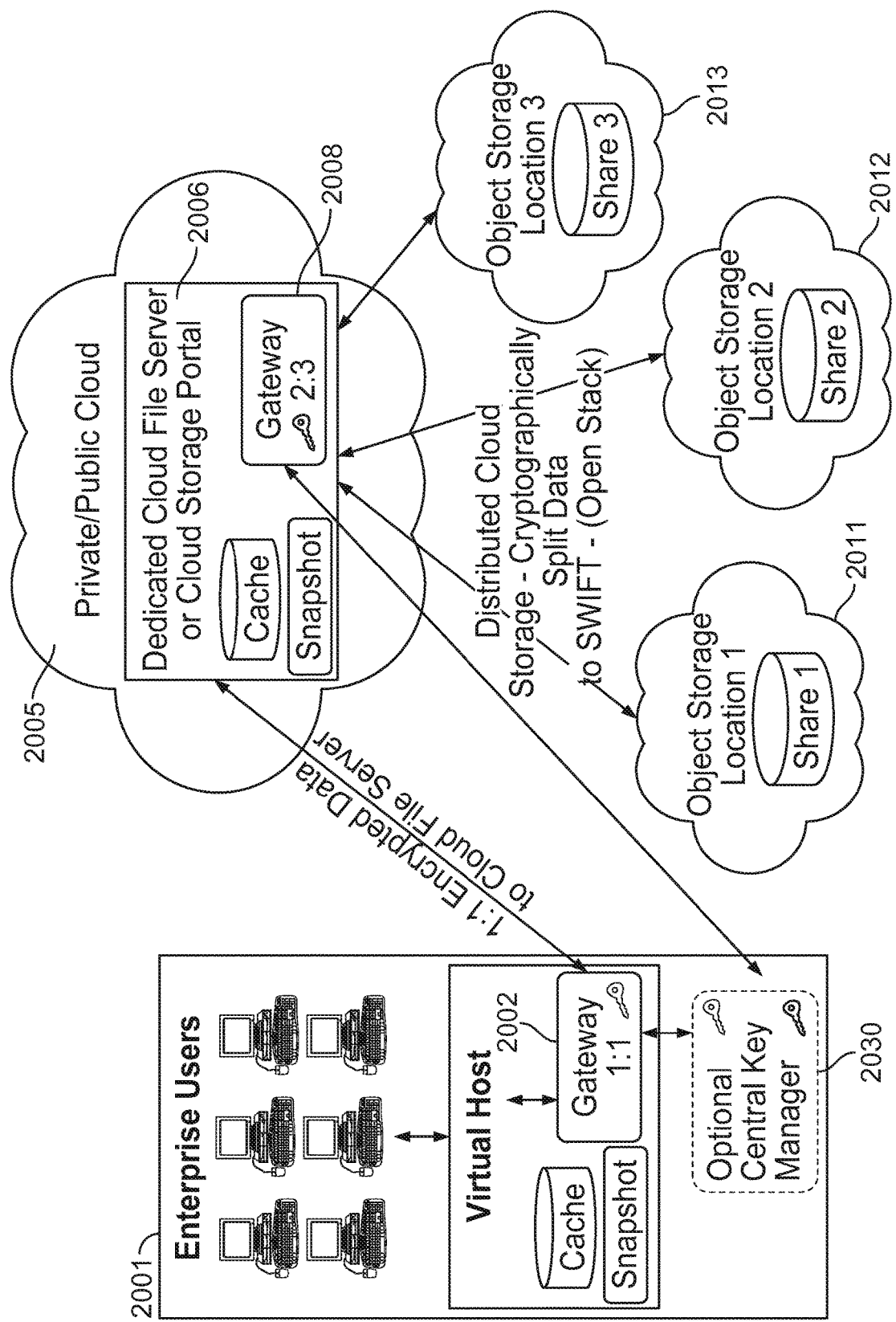
FIGS. 20A-B provide schematic diagrams illustrating example infrastructures of an enterprise network to provide bandwidth control, in accordance with an implementation.
Figure 20B:
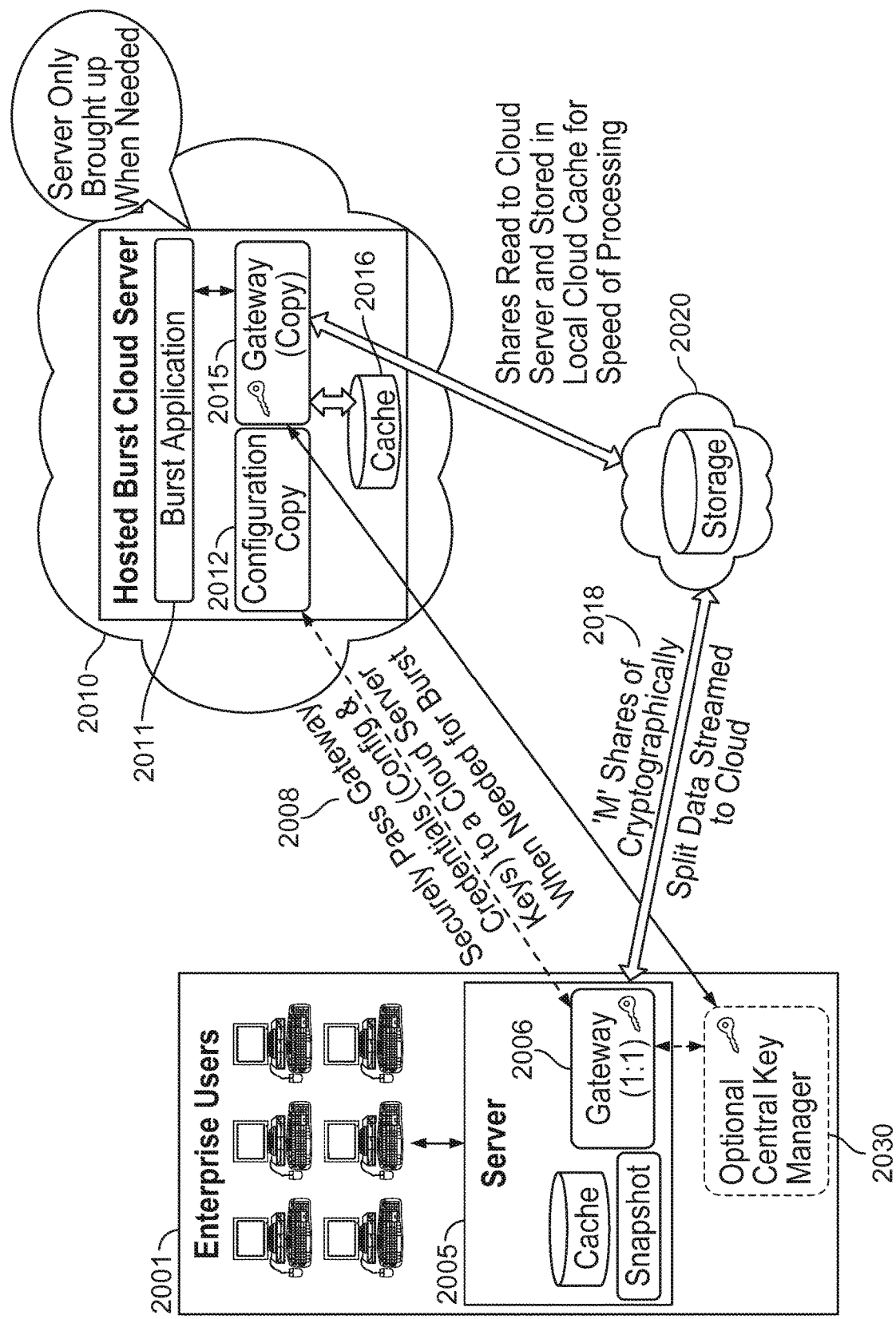

FIGS. 20A-B provide schematic diagrams illustrating example infrastructures of an enterprise network to provide bandwidth control in accordance with an implementation. In FIG. 20A, the enterprise 2001 may adopt geo-distributed cloud storage in different locations 2011-2013 to avoid brute force attack. For example, the local gateway 2002 may send encrypted data to a cloud file server 2006 in the private or public enterprise cloud 2005. The cloud gateway 2008 may in turn distribute cryptographically split data to geo-separated cloud storage locations 2011-2013. Specifically, a key manager 2030 at the enterprise premises may share an encryption key with the cloud gateway 2008 in the cloud file server 2006. In this way, a two-level encryption mechanism may be implemented, e.g., each data file and/or cluster block is locally encrypted at gateway 2002, and is subsequently cryptographically split into data shares at the cloud gateway 2008.

In FIG. 20B, a mirror gateway 2015 may be employed in a burst cloud server 2010, which resides in a private or public enterprise cloud. The local gateway 2006 residing on the on-premises server 2005, may cryptographically perform M of N cryptographic parse of data and send data shares to the cloud storage 2020 directly. When data bursts occur, the gateway 2006 may utilize the mirror gateway 2015 to help perform the cryptographic parse of data. For example, the gateway 2006 may securely pass gateway credentials (e.g., configurations and keys) to a cloud server 2010 when data bursts occur. The burst application 2011 running on the burst cloud server 2010 may keep a configuration copy 2012 of the gateway credentials, and a mirror gateway 2015 to cryptographically generate and send data shares to the cloud storage 2020. The shares may be stored in a local cloud cache 2016 for speed of processing.

Figure 21:
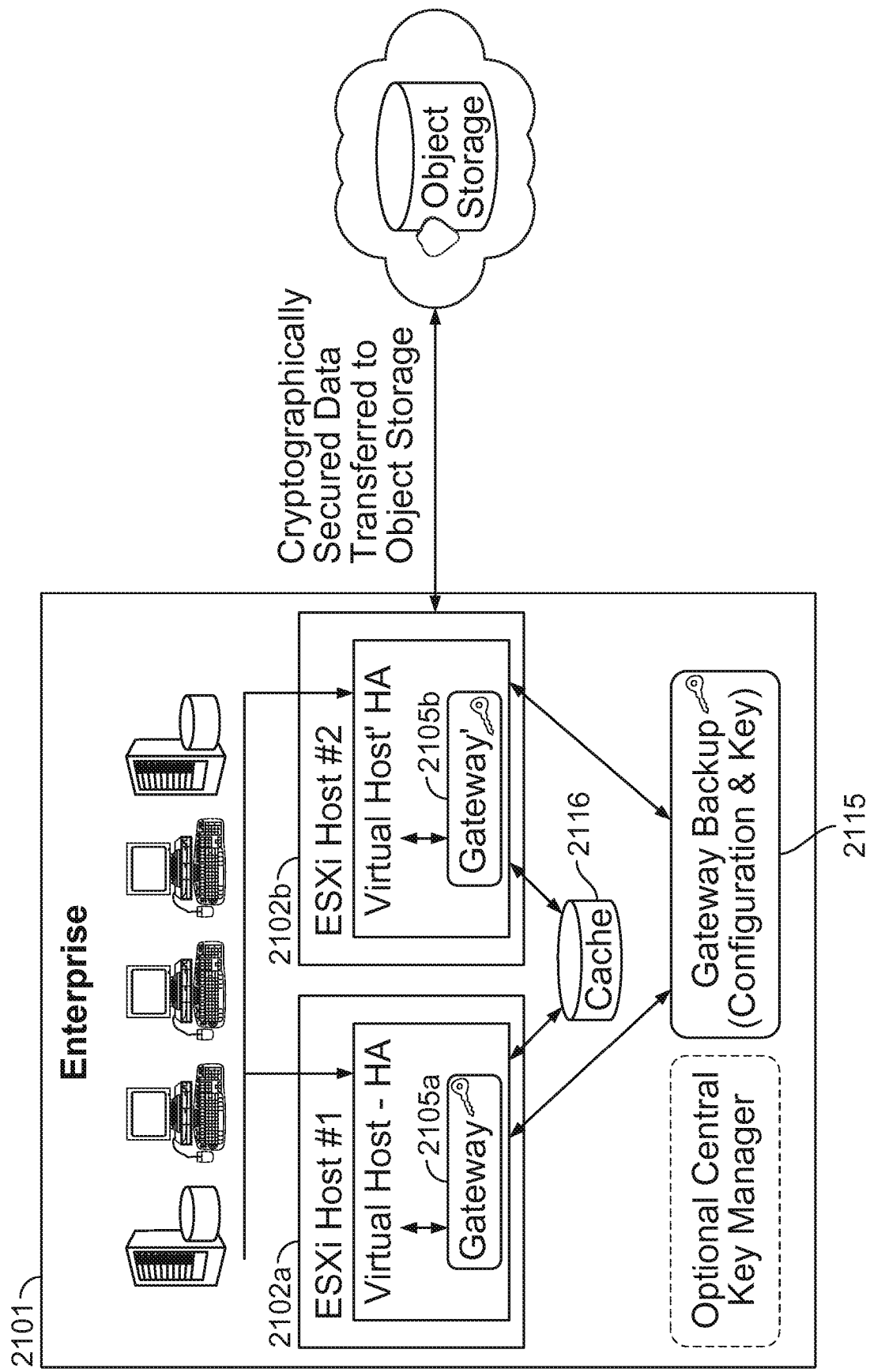
FIG. 21 provides a schematic diagram illustrating example infrastructure of an enterprise network using an operating system-independent hypervisor (e.g., an ESXi host) for extended availability, in accordance with an implementation.

FIG. 21 provides a schematic diagram illustrating example infrastructure of an enterprise network using an operating system-independent hypervisor (e.g., an ESXi host) for extended availability in accordance with an implementation. For example, multiple ESXi hosts 2102*a-b* may be installed at the enterprise premises 2101, each of which has access to the same gateway backup module 2115 and local cache 2116. When the primary gateway 2105*a* fails, the backup gateway 2105*b* may handle the data processing with the local cache 2116.

In one example, VMWare Virtual SAN clusters server hard disk and solid state drives (SSDs) may be used to create a flash optimized and highly resilient shared data store on the enterprise premise. ESXi hosts 2102*a-b* may support redundant array of independent disks (RAID) controllers to protect against disk failures within a server.

Figure 22:
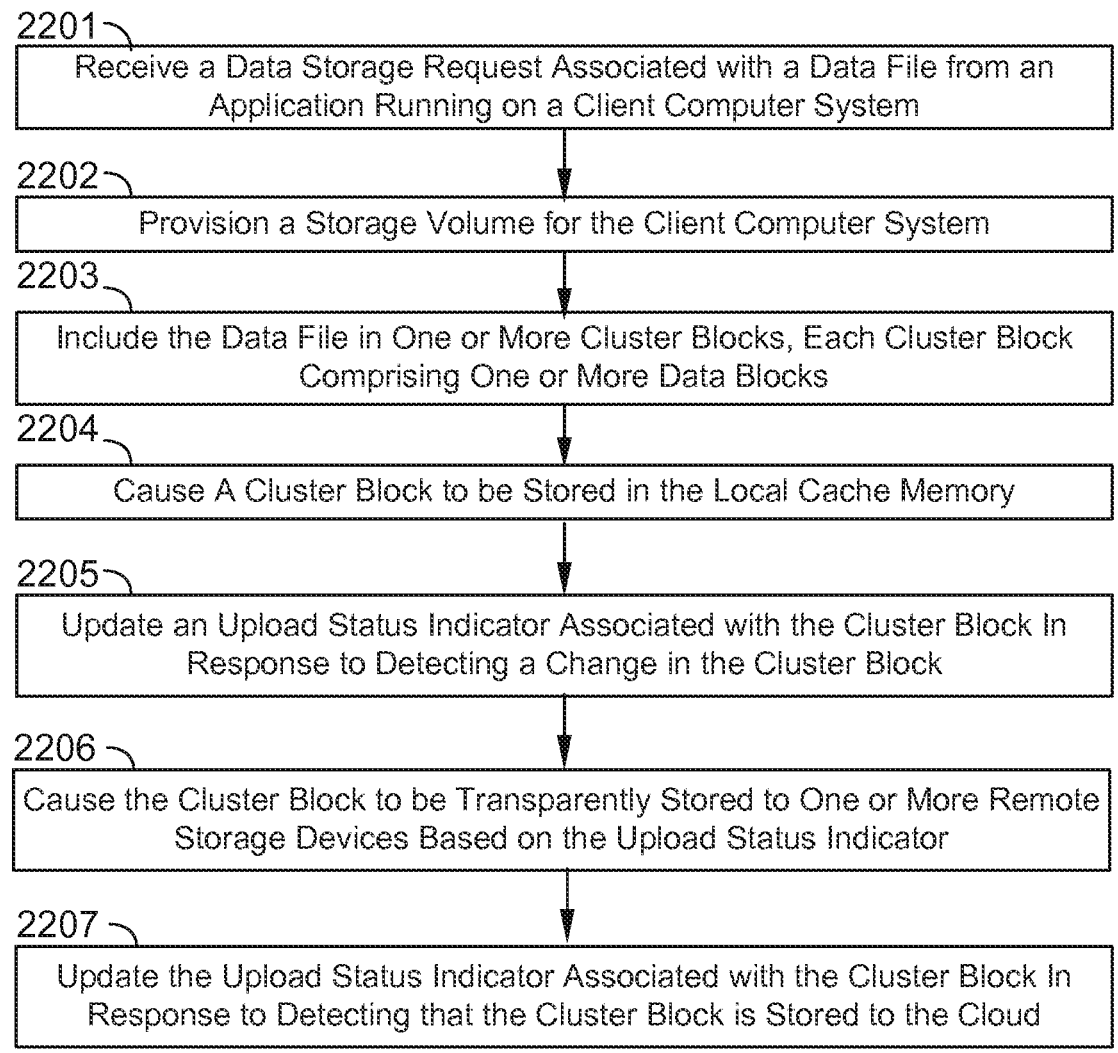
FIG. 22 provides an example logic flow diagram illustrating aspects of processing a data storage request at a gateway, in accordance with an implementation.
Figure 23:
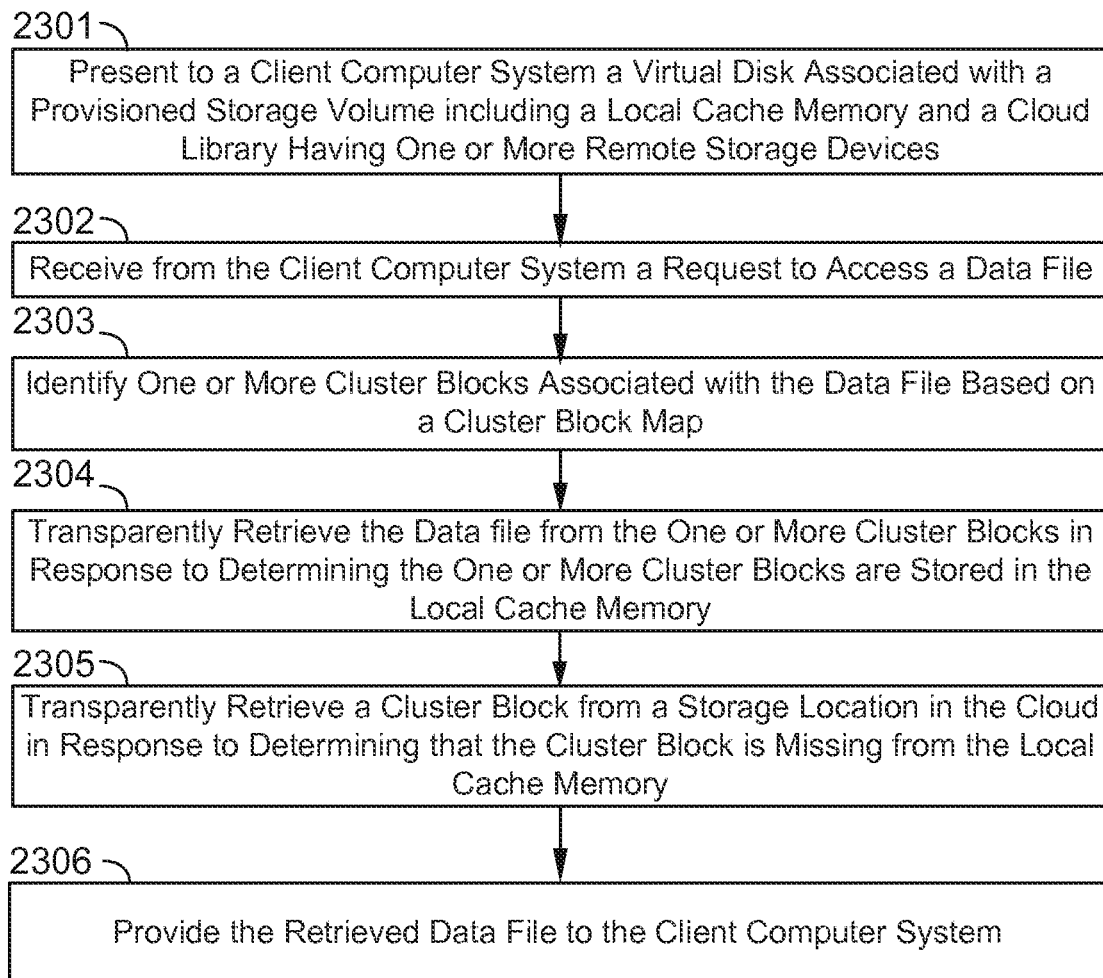
FIG. 23 provides an example logic flow diagram illustrating aspects of processing a data retrieval request at the gateway, in accordance with an implementation.
Figure 24:
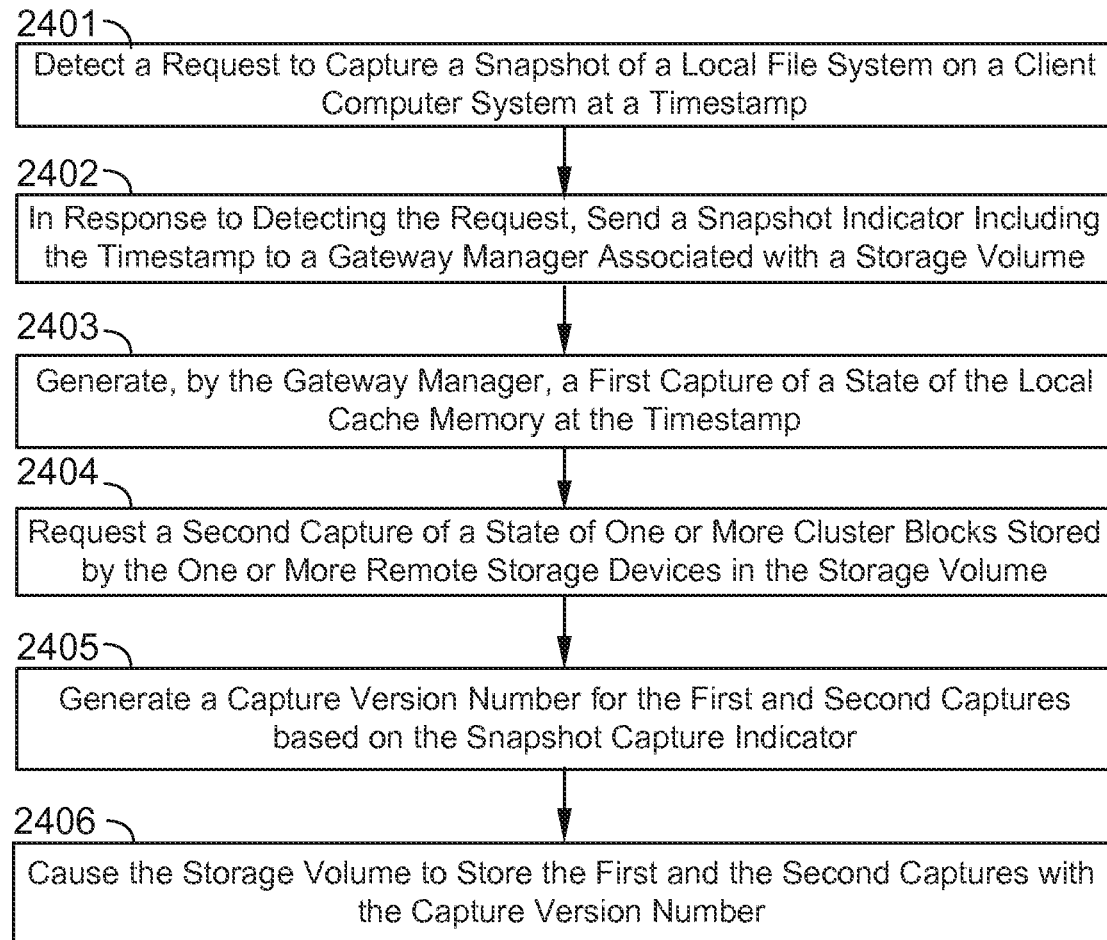
FIG. 24 provides an example logic flow diagram illustrating aspects of generating and storing a data capture of the gateway storage, in accordance with an implementation.

FIGS. 22-24 provide various logic flow diagrams illustrating operations of a gateway caching system, which may be supported by any of the example network infrastructures and/or server-side gateway architecture shown in FIGS. 13-14 and 17A-21.

FIG. 22 provides an example logic flow diagram illustrating aspects of processing a data storage request at a gateway, in accordance with an implementation. At step 2201, a data storage request associated with a data file is received at a gateway (e.g., the gateway 1305 in FIG. 13) from an application running on a client computer system (e.g., client devices/systems 1401a-e in FIG. 14). At step 2202, a storage volume for the client computer system is provisioned (e.g., by the logical volume manager 1411 in FIG. 14). The provisioned storage volume may include a local cache memory (e.g., the local cache memory 1416 in FIG. 14), which is communicatively coupled to the client computer system, and a cloud library comprising one or more remote storage devices (e.g., remote storage devices 1405a-c in FIG. 14) in one or more clouds. The storage volume may be dynamically or configurably adjusted by transparently including or excluding a subset of the one or more remote storage devices and one or more local storage devices (e.g., at the transparent block device 1408 in FIG. 14).

At step 2203, the data file may be included in one or more cluster blocks (e.g., by 1408 in FIG. 14). For example, as discussed in connection with FIG. 14, the data file may be decomposed into a number of data blocks (e.g., with a size of 2 KB, 4 KB, 6 KB, etc.). The data blocks may be grouped into cluster blocks having a larger size (e.g., 2 MB, 4 MB, 10 MB, etc.), e.g., by the transparent block device 1408 in FIG. 14. Each cluster block comprises a number of data blocks, and each cluster block may be written simultaneously to the cloud library one at a time.

At step 2204, the cluster blocks may be caused to be stored in the local cache memory (e.g., local cache 1416 in FIG. 14). At step 2205, in response to detecting a change in the one or more cluster blocks, an upload status indicator associated with the cluster blocks may be updated (e.g., at an upload directory in the local cache 1416 in FIG. 14). For example, an upload status indicator may be updated to be "to be uploaded" for a cluster block. At step 2206, the one or more cluster blocks may be transparently stored to the one or more remote storage devices (e.g., via the cloud interface library 1409 in FIG. 14) based on the upload status indicator associated with each cluster block. For example, cluster blocks that have an upload status indicator "to be uploaded" are to be transparently stored to the cloud. At step 2207, the upload status indicator associated with each of the one or more cluster blocks may be updated in response to detecting that the respective cluster block is stored to the cloud library (e.g., via the cloud interface library 1409 in FIG. 14). For example, the upload status indicator of a cluster block that has been uploaded to the cloud may be updated to be "upload completed."

FIG. 23 provides an example logic flow diagram illustrating aspects of processing a data retrieval request at the gateway, in accordance with an implementation. At step 2301, the client computer system a virtual disk (e.g., at the application layer 1401 in FIG. 14). The virtual disk may be associated with the provisioned storage volume discussed in connection with FIG. 22. At step 2302, a request to access a data file is received from the client computer system (e.g., the client devices/systems 1401a-e in FIG. 14). At step 2303, one or more cluster blocks associated with the data file may be identified (e.g., at a device mapper 1507 in FIGS. 15A-B). For example, a cluster block map may be employed to relate identifying information associated with the data file to identifying information of the cluster blocks. In this way, the request for the data file may be translated to a request for one or more previously stored cluster blocks. At step 2304, in response to determining that the identified one or more cluster blocks are stored in the local cache memory, the data file may be transparently retrieved from the one or more cluster blocks (e.g., at the transparent block device 1408 in FIG. 14). At step 2305, in response to determining that at least one of the identified one or more cluster blocks is missing from the local cache memory, the missed cluster block may be transparently retrieved from a storage location from the cloud (e.g., via the cloud interface library 1409 in FIG. 14). It is noted that although any request or operation to retrieve a cluster block from the cloud may be transparent to the client computer system, the exact storage location of the cluster block may be hidden from the client computer system. At step 2306, the retrieved data file is provided to the client computer system, or the application running on the client computer system (e.g., via the connectivity layer 1402 in FIG. 14).

FIG. 24 provides an example logic flow diagram illustrating aspects of generating and storing a data capture of the gateway storage, in accordance with an implementation. At step 2401, a request to capture a snapshot of a local file system of the client computer system may be detected (e.g., by the snapshot module 1413 in FIG. 14) at a timestamp. The client computer system may be presented with a virtual disk having a storage volume, as discussed in FIGS. 22-23. At step 2402, in response to detecting the request, a snapshot capture indicator may be sent including the timestamp to a gateway manager (e.g., the gateway 1305 in FIG. 13) associated with the storage volume. At step 2403, the gateway manager may generate a first capture of a state of the local cache memory (e.g., the local cache memory 1416 in FIG. 14) at the timestamp. At step 2404, the gateway manger may request a second capture of a state of one or more cluster blocks stored by the one or more remote storage devices at the timestamp. The one or more cluster blocks are related to one or more data files stored with the local file system. For example, the one or more cluster blocks may include a part an entirety of a data file that is currently stored, or has been previously stored associated with the local file system. At step 2405, a capture version number for the first and second capture based on the snapshot capture indicator may be generated (e.g., by the snapshot module 1413 in FIG. 14). For example, the capture version number indicates a version of the capture such that the local file system may roll back in time to recover a data version at an earlier time. At step 2046, the storage volume may be caused to store the first capture, the second capture and the capture version number. For example, the first capture and the second capture associated with the capture version number may be written to the local cache memory and the remote cloud storage in a similar manner as discussed in connection with FIG. 16.

In various implementations as discussed throughout FIGS. 13-24, the cloud-based storage may be configured to meet certain regulatory compliance requirements, including but not limited to Health Insurance Portability and Accountability Act (HIPAA), European Union Data Protection Directive (EUDPA), Sarbanes—Oxley Act (SOX), Payment Card Industry (PCI) Data Security Standard (DSS), Health Information Technology for Economic and Clinical Health Act (HITECH), Gramm-Leach-Bliley Act (GLBA), Family Educational Rights and Privacy Act (FERPA), Federal Information Security Management Act (FISMA), and/or the like.

Although some applications of the secure data parser are described above, it should be clearly understood that the present invention may be integrated with any network application in order to increase security, fault-tolerance, anonymity, or any suitable combination of the foregoing.

Additionally, other combinations, additions, substitutions and modifications will be apparent to the skilled artisan in view of the disclosure herein.

What is claimed is:

1. A method for providing improved scalable cloud-based storage to a client computer system, the method comprising:
   receiving, using a programmed hardware processor, a data storage request associated with a data file, wherein the data storage request is generated by an application running on the client computer system;
   provisioning a storage volume for the client computer system, wherein the provisioned storage volume: (1) comprises a local cache memory communicatively coupled to the client computer system and a cloud library comprising one or more remote storage devices in one or more clouds, and (2) is dynamically or configurably adjustable by transparently including or excluding a subset of the one or more remote storage devices and one or more local storage devices;
   including the data file in one or more cluster blocks, each cluster block of the one or more cluster blocks comprising a plurality of different data blocks that are written simultaneously to the cloud library over a plurality of channels;
   causing the one or more cluster blocks to be stored in the local cache memory;
   in response to detecting a change in the one or more cluster blocks, causing the one or more cluster blocks to be transparently stored to the one or more remote storage devices; and
   in response to receiving an access request to the data file, retrieving from the cloud library a subset of the plurality of different data blocks, wherein the subset of the plurality of different data blocks is retrieved simultaneously over the plurality of channels.

2. The method of claim 1, wherein the local cache memory comprises non-volatile memory located within the client computer system or in a gateway server within a local network of the client computer system.

3. The method of claim 1, wherein the including the data file in the one or more cluster blocks of the one or more cluster blocks comprises:
   generating, using a device mapper module, one or more sequential identifiers for a subset of data blocks generated from the data file; and
   updating a block map for the one or more cluster blocks to associate the one or more sequential identifiers with the data file.

4. The method of claim 1, further comprising removing a respective cluster block from the local cache memory in response to detecting that the respective cluster block is stored to the cloud library.

5. The method of claim 1, further comprising removing a selected cluster block from the local cache memory in response to detecting that an available storage space of the local cache memory is less than or equal to a predetermined threshold.

6. The method of claim 5, further comprising selecting the selected cluster block for removal in response to determining that the selected cluster block is a least recently used cluster block in the local cache memory.

7. The method of claim 5, further comprising selecting the selected cluster block for removal in response to determining that the selected cluster block is a least frequently used cluster block in the local cache memory.

8. The method of claim 1, further comprising transparently increasing a total capacity of the local cache memory in response to detecting that a file size of the data file exceeds an available storage capacity of the local cache memory.

9. The method of claim 1, further comprising controlling a data transfer rate to the local cache memory in response to detecting that a file size of the data file exceeds an available storage capacity of the local cache memory, thereby avoiding storage overflow of the local cache memory.

10. The method of claim 1, wherein each cluster block of the one or more cluster blocks has a predetermined size determined based on one or more criteria selected from the group consisting of cloud-access latency, a total size of the data file, a file type of the data file, and a total capacity of the local cache memory.

11. The method of claim 1, wherein each cluster block of the one or more cluster blocks comprises a plurality of data blocks obtained from a plurality of separate data files.

12. The method of claim 1, wherein the one or more remote storage devices are geographically separated.

13. The method of claim 1, further comprising updating an upload status indicator associated with a respective one of the one or more cluster blocks in response to detecting a change in the respective one of the one or more cluster blocks in the local cache memory.

14. The method of claim 1, further comprising updating an upload status indicator associated with a respective one of the one or more cluster blocks in response to detecting that the respective one of the one or more cluster blocks is stored to the cloud library.

15. The method of claim 1, wherein:
   the causing the one or more cluster blocks to be stored in the local cache memory further comprises applying a first cryptographic operation to the one or more cluster blocks; and
   the causing the one or more cluster blocks to be transparently stored to the one or more remote storage devices further comprises applying a second cryptographic operation to the one or more cluster blocks.

16. The method of claim 15, wherein:
   the applying the first cryptographic operation comprises encrypting the one or more cluster blocks using a first encryption key; and
   the applying the second cryptographic operation comprises encrypting the one or more cluster blocks using a second encryption key different from the first encryption key.

17. The method of claim 16, further comprising storing the first encryption key, the second encryption key, or both in a separate storage location from the one or more cluster blocks.

18. The method of claim 1, wherein the causing the one or more cluster blocks to be transparently stored to the one or more remote storage devices comprises causing the one or more cluster blocks to be distributed in a plurality of data shares located in the one or more remote storage devices, each share of the plurality of data shares comprising a portion of each cluster block in a subset of the one or more cluster blocks.

19. The method of claim 18, wherein the causing each share of the plurality of data shares to be distributed in a plurality of data shares comprises causing each cluster block to be shuffled into a single data share of the plurality of data shares.

20. The method of claim 18, wherein the causing each share to be distributed in a plurality of data shares comprises splitting each cluster block into a plurality of secondary data units and causing each secondary data unit to be placed into one of the plurality of data shares, wherein each cluster block is restorable by recombining a subset less than all of the secondary data units from the plurality of data shares.

* * * * *